US006476187B1

(12) United States Patent
Cone et al.

(10) Patent No.: US 6,476,187 B1
(45) Date of Patent: Nov. 5, 2002

(54) METHODS AND REAGENTS FOR DISCOVERING AND USING MAMMALIAN MELANOCORTIN RECEPTOR AGONISTS AND ANTAGONISTS TO MODULATE FEEDING BEHAVIOR IN ANIMALS

(75) Inventors: Roger D. Cone, Oregon City; Wei Fan, Portland; Bruce A. Boston, Lake Osewego; Robert A. Kesterton, Portland; Dongsi Lu, Beaverton; Wenbiao Chen, Portland, all of OR (US)

(73) Assignee: Oregon Health & Sciences University, Portland, OR (US)

( * ) Notice: Subject to any disclaimer, the term of this patent is extended or adjusted under 35 U.S.C. 154(b) by 0 days.

(21) Appl. No.: 09/353,099

(22) Filed: Jul. 14, 1999

Related U.S. Application Data

(60) Division of application No. 08/706,281, filed on Sep. 4, 1996, now Pat. No. 6,100,048, which is a continuation-in-part of application No. 08/466,906, filed on Jun. 6, 1995, now Pat. No. 5,849,871, which is a division of application No. 07/866,979, filed on Apr. 10, 1992, now Pat. No. 5,532,347, and a continuation-in-part of application No. 08/478,992, filed on Jun. 7, 1995, now Pat. No. 5,773,229, which is a division of application No. 08/077,673, filed on Jun. 15, 1993, now Pat. No. 5,554,729, which is a division of application No. 07/866,560, filed on Apr. 10, 1992, now Pat. No. 5,280,112, and a continuation-in-part of application No. 08/044,812, filed on Apr. 8, 1993, now Pat. No. 5,837, 521.

(51) Int. Cl.[7] .......................... A61K 38/00; C07K 5/00; C07K 7/00

(52) U.S. Cl. .......................................... 530/317; 514/9

(58) Field of Search .............................. 514/9; 530/317

(56) References Cited

U.S. PATENT DOCUMENTS

| | | | | | |
|---|---|---|---|---|---|
| 5,554,729 | A | * | 9/1996 | Cone et al. | 530/351 |
| 5,674,839 | A | * | 10/1997 | Hruley et al. | 514/9 |
| 5,773,229 | A | * | 6/1998 | Cone et al. | 435/7.21 |
| 5,837,521 | A | * | 11/1998 | Cone et al. | 435/240.1 |
| 5,849,871 | A | * | 12/1998 | Cone et al. | 530/350 |

* cited by examiner

*Primary Examiner*—Avis M. Davenport
(74) *Attorney, Agent, or Firm*—McDonnell Boehnen Hulbert & Berghoff

(57) ABSTRACT

The present invention provides recombinant expression constructs comprising nucleic acid encoding mammalian melanocortin receptors, and mammalian cells into which said recombinant expression constructs have been introduced that express functional mammalian melanocortin receptors. The invention provides a panel of such transformed mammalian cells expressing melanocortin receptors for screening compounds for receptor agonist and antagonist activity. The invention also provides methods for using such panels of melanocortin receptor-expressing mammalian cells to specifically-detect and identify agonists and antagonists for each melanocortin receptor, as well as patterns of agonist and antagonist activity of said compounds for the class of melanocortin receptors. Such screening methods provide a means for identifying compounds with patterns of melanocortin agonist and antagonist activity which is associated with the capacity to influence or modify metabolism and behavior, particularly feeding behavior.

1 Claim, 48 Drawing Sheets

Figure 1A

```
TTCCTGACAA GACT ATG TCC ACT CAG GAG CCC CAG AAG AGT CTT CTG GGT       50
                Met Ser Thr Gln Glu Pro Gln Lys Ser Leu Leu Gly
                 1               5                  10

TCT CTC AAC TCC AAT GCC ACC TCT CAC CTT GGA CTG GCC ACC AAC CAG      98
Ser Leu Asn Ser Asn Ala Thr Ser His Leu Gly Leu Ala Thr Asn Gln
        15                  20                  25

TCA GAG CCT TGG TGC CTG TAT GTG TCC ATC CCA GAT GGC CTC TTC CTC     146
Ser Glu Pro Trp Cys Leu Tyr Val Ser Ile Pro Asp Gly Leu Phe Leu
    30                  35                  40

AGC CTA GGG CTG GTG AGT CTG GTG GAG AAT GTG CTG GTT GTG ATA GCC     194
Ser Leu Gly Leu Val Ser Leu Val Glu Asn Val Leu Val Val Ile Ala
 45                 50                  55                  60

ATC ACC AAA AAC CGC AAC CTG CAC TCG CCC ATG TAT TAC TTC ATC TGC     242
Ile Thr Lys Asn Arg Asn Leu His Ser Pro Met Tyr Tyr Phe Ile Cys
                65                  70                  75

TGC CTG GCC CTG TCT GAC CTG ATG GTA AGT GTC AGC ATC GTG CTG GAG     290
Cys Leu Ala Leu Ser Asp Leu Met Val Ser Val Ser Ile Val Leu Glu
            80                  85                  90

ACT ACT ATC ATC CTG CTG CTG GAG GTG GGC ATC CTG GTG GCC AGA GTG     338
Thr Thr Ile Ile Leu Leu Leu Glu Val Gly Ile Leu Val Ala Arg Val
        95                 100                 105

GCT TTG GTG CAG CAG CTG GAC AAC CTC ATT GAC GTG CTC ATC TGT GGC     386
Ala Leu Val Gln Gln Leu Asp Asn Leu Ile Asp Val Leu Ile Cys Gly
    110                 115                 120

TCC ATG GTG TCC AGT CTC TGC TTC CTG GGC ATC ATT GCT ATA GAC CGC     434
Ser Met Val Ser Ser Leu Cys Phe Leu Gly Ile Ile Ala Ile Asp Arg
125                 130                 135                 140

TAC ATC TCC ATC TTC TAT GCG CTG CGT TAT CAC AGC ATC GTG ACG CTG     482
Tyr Ile Ser Ile Phe Tyr Ala Leu Arg Tyr His Ser Ile Val Thr Leu
                145                 150                 155

CCC AGA GCA CGA CGG GCT GTC GTG GGC ATC TGG ATG GTC AGC ATC GTC     530
Pro Arg Ala Arg Arg Ala Val Val Gly Ile Trp Met Val Ser Ile Val
            160                 165                 170

TCC AGC ACC CTC TTT ATC ACC TAC TAC AAG CAC ACA GCC GTT CTG CTC     578
Ser Ser Thr Leu Phe Ile Thr Tyr Tyr Lys His Thr Ala Val Leu Leu
        175                 180                 185

TGC CTC GTC ACT TTC TTT CTA GCC ATG CTG GCA CTC ATG GCG ATT CTG     626
Cys Leu Val Thr Phe Phe Leu Ala Met Leu Ala Leu Met Ala Ile Leu
    190                 195                 200
```

Figure 1B

```
TAT GCC CAC ATG TTC ACG AGA GCG TGC CAG CAC GTC CAG GGC ATT GCC      674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG      722
Gln Leu His Lys Arg Arg Arg Ser Ile Arg Gln Gly Phe Cys Leu Lys
                225                 230                 235

GGT GCT GCC ACC CTT ACT ATC CTT CTG GGG ATT TTC TTC CTG TGC TGG      770
Gly Ala Ala Thr Leu Thr Ile Leu Leu Gly Ile Phe Phe Leu Cys Trp
            240                 245                 250

GGC CCC TTC TTC CTG CAT CTC TTG CTC ATC GTC CTC TGC CCT CAG CAC      818
Gly Pro Phe Phe Leu His Leu Leu Leu Ile Val Leu Cys Pro Gln His
        255                 260                 265

CCC ACC TGC AGC TGC ATC TTC AAG AAC TTC AAC CTC TTC CTC CTC CTC      866
Pro Thr Cys Ser Cys Ile Phe Lys Asn Phe Asn Leu Phe Leu Leu Leu
    270                 275                 280

ATC GTC CTC AGC TCC ACT GTT GAC CCC CTC ATC TAT GCT TTC CGC AGC      914
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG          959
Gln Glu Leu Arg Met Thr Leu Lys Glu Val Leu Leu Cys Ser Trp
                305                 310                 315

TGATCAGAGG GCGCTGGGCA GAGGGTGACA GTGATATCCA GTGGCCTGCA TCTGTGAGAC   1019

CACAGGTACT CATCCCTTCC TGATCTCCAT TTGTCTAAGG GTCGACAGGA TGAGCTTTAA   1079

AATAGAAACC CAGAGTGCCT GGGGCCAGGA GAAAGGGTAA CTGTGACTGC AGGGCTCACC   1139

CAGGGCAGCT ACGGGAAGTG GAGGAGACAG GGATGGGAAC TCTAGCCCTG AGCAAGGGTC   1199

AGACCACAGG CTCCTGAAGA GCTTCACCTC TCCCCACCTA CAGGCAACTC CTGCTCAAGC   1259

C                                                                   1260
```

```
CCCGCATGTG GCCGCCCTCA ATGGAGGGCT CTGAGAACGA CTTTTAAAAC GCAGAGAAAA      60

AGCTCCATTC TTCCCAGACC TCAGCGCAGC CCTGGCCCAG GAAGGGAGGA GACAGAGGCC     120

AGGACGGTCC AGAGGTGTCG AAATGTCCTG GGAACCTGAG CAGCAGCCAC CAGGGAAGAG     180

GCAGGGAGGG AGCTGAGGAC CAGGCTTGGT TGTGAGAATC CCTGAGCCCA GGCGGTTGAT     240

GCCAGGAGGT GTCTGGACTG GCTGGGCCAT GCCTGGGCTG ACCTGTCCAG CCAGGGAGAG     300

GGTGTGAGGG CAGATCTGGG GGTGCCCAGA TGGAAGGAGG CAGGCATGGG GACACCCAAG     360

GCCCCCTGGC AGCACCATGA ACTAAGCAGG ACACCTGGAG GGGAAGAACT GTGGGGACCT     420

GGAGGCCTCC AACGACTCCT TCCTGCTTCC TGGACAGGAC T ATG GCT GTG CAG         473
                                              Met Ala Val Gln
                                                1

GGA TCC CAG AGA AGA CTT CTG GGC TCC CTC AAC TCC ACC CCC ACA GCC       521
Gly Ser Gln Arg Arg Leu Leu Gly Ser Leu Asn Ser Thr Pro Thr Ala
  5                  10                  15                  20

ATC CCC CAG CTG GGG CTG GCT GCC AAC CAG ACA GGA GCC CGG TGC CTG       569
Ile Pro Gln Leu Gly Leu Ala Ala Asn Gln Thr Gly Ala Arg Cys Leu
                 25                  30                  35

GAG GTG TCC ATC TCT GAC GGG CTC TTC CTC AGC CTG GGG CTG GTG AGC       617
Glu Val Ser Ile Ser Asp Gly Leu Phe Leu Ser Leu Gly Leu Val Ser
             40                  45                  50

TTG GTG GAG AAC GCG CTG GTG GTG GCC ACC ATC GCC AAG AAC CGG AAC       665
Leu Val Glu Asn Ala Leu Val Val Ala Thr Ile Ala Lys Asn Arg Asn
         55                  60                  65

CTG CAC TCA CCC ATG TAC TGC TTC ATC TGC TGC CTG GCC TTG TCG GAC       713
Leu His Ser Pro Met Tyr Cys Phe Ile Cys Cys Leu Ala Leu Ser Asp
     70                  75                  80

CTG CTG GTG AGC GGG ACG AAC GTG CTG GAG ACG GCC GTC ATC CTC CTG       761
Leu Leu Val Ser Gly Thr Asn Val Leu Glu Thr Ala Val Ile Leu Leu
 85                  90                  95                 100

CTG GAG GCC GGT GCA CTG GTG GCC CGG GCT GCG GTG CTG CAG CAG CTG       809
Leu Glu Ala Gly Ala Leu Val Ala Arg Ala Ala Val Leu Gln Gln Leu
                105                 110                 115

GAC AAT GTC ATT GAC GTG ATC ACC TGC AGC TCC ATG CTG TCC AGC CTC       857
Asp Asn Val Ile Asp Val Ile Thr Cys Ser Ser Met Leu Ser Ser Leu
            120                 125                 130

TGC TTC CTG GGC GCC ATC GCC GTG GAC CGC TAC ATC TCC ATC TTC TAC       905
Cys Phe Leu Gly Ala Ile Ala Val Asp Arg Tyr Ile Ser Ile Phe Tyr
        135                 140                 145
```

Figure 2B

```
GCA CTG CGC TAC CAC AGC ATC GTG ACC CTG CCG CGG GCG CCG CGA GCC       953
Ala Leu Arg Tyr His Ser Ile Val Thr Leu Pro Arg Ala Pro Arg Ala
    150                 155                 160

GTT GCG GCC ATC TGG GTG GCC AGT GTC GTC TTC AGC ACG CTC TTC ATC      1001
Val Ala Ala Ile Trp Val Ala Ser Val Val Phe Ser Thr Leu Phe Ile
165                 170                 175                 180

GCC TAC TAC GAC CAC GTG GCC GTC CTG CTG TGC CTC GTG GTC TTC TTC      1049
Ala Tyr Tyr Asp His Val Ala Val Leu Leu Cys Leu Val Val Phe Phe
                185                 190                 195

CTG GCT ATG CTG GTG CTC ATG GCC GTG CTG TAC GTC CAC ATG CTG GCC      1097
Leu Ala Met Leu Val Leu Met Ala Val Leu Tyr Val His Met Leu Ala
            200                 205                 210

CGG GCC TGC CAG CAC GCC CAG GGC ATC GCC CGG CTC CAC AAG AGG CAG      1145
Arg Ala Cys Gln His Ala Gln Gly Ile Ala Arg Leu His Lys Arg Gln
        215                 220                 225

CGC CCG GTC CAC CAG GGC TTT GGC CTT AAA GGC GCT GTC ACC CTC ACC      1193
Arg Pro Val His Gln Gly Phe Gly Leu Lys Gly Ala Val Thr Leu Thr
    230                 235                 240

ATC CTG CTG GGC ATT TTC TTC CTC TGC TGG GGC CCC TTC TTC CTG CAT      1241
Ile Leu Leu Gly Ile Phe Phe Leu Cys Trp Gly Pro Phe Phe Leu His
245                 250                 255                 260

CTC ACA CTC ATC GTC CTC TGC CCC GAG CAC CCC ACG TGC GGC TGC ATC      1289
Leu Thr Leu Ile Val Leu Cys Pro Glu His Pro Thr Cys Gly Cys Ile
                265                 270                 275

TTC AAG AAC TTC AAC CTC TTT CTC GCC CTC ATC ATC TGC AAT GCC ATC      1337
Phe Lys Asn Phe Asn Leu Phe Leu Ala Leu Ile Ile Cys Asn Ala Ile
            280                 285                 290

ATC GAC CCC CTC ATC TAC GCC TTC CAC AGC CAG GAG CTC CGC AGG ACG      1385
Ile Asp Pro Leu Ile Tyr Ala Phe His Ser Gln Glu Leu Arg Arg Thr
        295                 300                 305

CTC AAG GAG GTG CTG ACA TGC TCC TGG TGAGCGCGGT GCACGCGCTT            1432
Leu Lys Glu Val Leu Thr Cys Ser Trp
    310                 315

TAAGTGTGCT GGGCAGAGGG AGGTGGTGAT ATTGTGGTCT GGTTCCTGTG TGACCCTGGG    1492

CAGTTCCTTA CCTCCCTGGT CCCCGTTTGT CAAAGAGGAT GGACTAAATG ATCTCTGAAA    1552

GTGTTGAAGC GCGGACCCTT CTGGGCAGGG AGGGGTCCTG CAAAACTCCA GGCAGGACTT    1612

CTCACCAGCA GTCGTGGGAA C                                              1633
```

Figure 3A

```
ACAACACTTT ATATATATTT TTATAAATGT AAGGGGTACA AAGGTGCCAT TTTGTTACAT      60

GGATATACCG TGTAGTGGTG AAGCCTGGGC TTTTAGTGTA TCTGTCATCA GAATAACATA     120

CGTGTTACCC ATAGGAATTT CTCATCACCC GCCCCCTCCA CCCTTCGAGT CTCCAATGTC     180

CATTCCACAC TCTATATCCA CGTGTATGCA TATAGCTCCA CATATAAGTG AGAACATGTA     240

GTATTTGACT TCCTCTTTCT GAGTTATTTC ACTTTGATAA TGGCCTCCAC TTCCATCCAT     300

GTTGCTGCAA AAGACATGAC CTTATTCTTT TTGATAGCTG GGGAGTACTC CATTGTGTAT     360

ATGTACCACA TTTCTTTATC CATTCACCCA TTGAGAACAC TTAGTTGATT CCATATCTTT     420

GCTATTGTCA CTAGTGCTGC AATAAACATA CATGTGCAGG CTCCTTCTAA TATACTGATT     480

TATATTTTAT GGAGAGAGAT AGAGTTCTTA GCGAGTGTGC TGTTTATTTC TAGTGTACTT     540

GCAACTAATA TTCTGTATAC TCCCTTTAGG TGATTGGAGA TTTAACTTAG ATCTCCAGCA     600

AGTGCTACAA GAAGAAAAGA TCCTGAAGAA TCAATCAAGT TTCCGTGAAG TCAAGTCCAA     660

GTAACATCCC CGCCTTAACC ACAAGCAGGA GAA ATG AAG CAC ATT ATC AAC TCG      714
                                     Met Lys His Ile Ile Asn Ser
                                      1               5

TAT GAA AAC ATC AAC AAC ACA GCA AGA AAT AAT TCC GAC TGT CCT CGT       762
Tyr Glu Asn Ile Asn Asn Thr Ala Arg Asn Asn Ser Asp Cys Pro Arg
         10                  15                  20

GTG GTT TTG CCG GAG GAG ATA TTT TTC ACA ATT TCC ATT GTT GGA GTT       810
Val Val Leu Pro Glu Glu Ile Phe Phe Thr Ile Ser Ile Val Gly Val
     25                  30                  35

TTG GAG AAT CTG ATC GTC CTG CTG GCT GTG TTC AAG AAT AAG AAT CTC       858
Leu Glu Asn Leu Ile Val Leu Leu Ala Val Phe Lys Asn Lys Asn Leu
 40                  45                  50                  55

CAG GCA CCC ATG TAC TTT TTC ATC TGT AGC TTG GCC ATA TCT GAT ATG       906
Gln Ala Pro Met Tyr Phe Phe Ile Cys Ser Leu Ala Ile Ser Asp Met
                 60                  65                  70

CTG GGC AGC CTA TAT AAG ATC TTG GAA AAT ATC CTG ATC ATA TTG AGA       954
Leu Gly Ser Leu Tyr Lys Ile Leu Glu Asn Ile Leu Ile Ile Leu Arg
             75                  80                  85

AAC ATG GGC TAT CTC AAG CCA CGT GGC AGT TTT GAA ACC ACA GCC GAT      1002
Asn Met Gly Tyr Leu Lys Pro Arg Gly Ser Phe Glu Thr Thr Ala Asp
         90                  95                 100
```

Figure 3B

GAC ATC ATC GAC TCC CTG TTT GTC CTC TCC CTG CTT GGC TCC ATC TTC 1050
Asp Ile Ile Asp Ser Leu Phe Val Leu Ser Leu Leu Gly Ser Ile Phe
105 110 115

AGC CTG TCT GTG ATT GCT GCG GAC CGC TAC ATC ACC ATC TTC CAC GCA 1098
Ser Leu Ser Val Ile Ala Ala Asp Arg Tyr Ile Thr Ile Phe His Ala
120 125 130 135

CTG CGG TAC CAC AGC ATC GTG ACC ATG CGC CGC ACT GTG GTG GTG CTT 1146
Leu Arg Tyr His Ser Ile Val Thr Met Arg Arg Thr Val Val Val Leu
140 145 150

ACG GTC ATC TGG ACG TTC TGC ACG GGG ACT GGC ATC ACC ATG GTG ATC 1194
Thr Val Ile Trp Thr Phe Cys Thr Gly Thr Gly Ile Thr Met Val Ile
155 160 165

TTC TCC CAT CAT GTG CCC ACA GTG ATC ACC TTC ACG TCG CTG TTC CCG 1242
Phe Ser His His Val Pro Thr Val Ile Thr Phe Thr Ser Leu Phe Pro
170 175 180

CTG ATG CTG GTC TTC ATC CTG TGC CTC TAT GTG CAC ATG TTC CTG CTG 1290
Leu Met Leu Val Phe Ile Leu Cys Leu Tyr Val His Met Phe Leu Leu
185 190 195

GCT CGA TCC CAC ACC AGG AAG ATC TCC ACC CTC CCC AGA GCC AAC ATG 1338
Ala Arg Ser His Thr Arg Lys Ile Ser Thr Leu Pro Arg Ala Asn Met
200 205 210 215

AAA GGG GCC ATC ACA CTG ACC ATC CTG CTC GGG GTC TTC ATC TTC TGC 1386
Lys Gly Ala Ile Thr Leu Thr Ile Leu Leu Gly Val Phe Ile Phe Cys
220 225 230

TGG GCC CCC TTT GTG CTT CAT GTC CTC TTG ATG ACA TTC TGC CCA AGT 1434
Trp Ala Pro Phe Val Leu His Val Leu Leu Met Thr Phe Cys Pro Ser
235 240 245

AAC CCC TAC TGC GCC TGC TAC ATG TCT CTC TTC CAG GTG AAC GGC ATG 1482
Asn Pro Tyr Cys Ala Cys Tyr Met Ser Leu Phe Gln Val Asn Gly Met
250 255 260

TTG ATC ATG TGC AAT GCC GTC ATT GAC CCC TTC ATA TAT GCC TTC CGG 1530
Leu Ile Met Cys Asn Ala Val Ile Asp Pro Phe Ile Tyr Ala Phe Arg
265 270 275

AGC CCA GAG CTC AGG GAC GCA TTC AAA AAG ATG ATC TTC TGC AGC AGG 1578
Ser Pro Glu Leu Arg Asp Ala Phe Lys Lys Met Ile Phe Cys Ser Arg
280 285 290 295

TAC TGG TAGAATGGCT GATCCCTGGT TTTAGAATCC ATGGGAATAA CGTTGCCAAG 1634
Tyr Trp

Figure 3C

```
TGCCAGAATA GTGTAACATT CCAACAAATG CCAGTGCTCC TCACTGGCCT TCCTTCCCTA    1694
ATGGATGCAA GGATGACCCA CCAGCTAGTG TTTCTGAATA CTATGGCCAG GAACAGTCTA    1754
TTGTAGGGGC AACTCTATTT GTGACTGGAC AGATAAAACG TGTAGTAAAA GAAGGATAGA    1814
ATACAAAGTA TTAGGTACAA AAGTAATTAG GTTTGCATTA CTTATGACAA ATGCATTACT    1874
TTTGCACCAA TCTAGTAAAA CAGCAATAAA AATTCAAGGG CTTTGGGCTA AGGCAAAGAC    1934
TTGCTTTCCT GTGGACATTA ACAAGCCAGT TCTGAGGCGG CCTTTCCAGG TGGAGGCCAT    1994
TGCAGCCAAT TTCAGAGT                                                  2012
```

Figure 4A

```
GGGGCCAGAA AGTTCCTGCT TCAGAGCAGA AGATCTTCAG CAAGAACTAC AAAGAAGAAA      60

AGATTCTGGA GAATCAATCA AGTTTCCTGT CAAGTTCCAG TAACGTTTCT GTCTTAACTG     120

CACACAGGAA AG ATG AAA CAC ATT CTC AAT CTG TAT GAA AAC ATC AAC         168
              Met Lys His Ile Leu Asn Leu Tyr Glu Asn Ile Asn
               1               5                  10

AGT ACA GCA AGA AAT AAC TCA GAC TGT CCT GCT GTG ATT TTG CCA GAA       216
Ser Thr Ala Arg Asn Asn Ser Asp Cys Pro Ala Val Ile Leu Pro Glu
        15                  20                  25

GAG ATA TTT TTC ACA GTA TCC ATT GTT GGG GTT TTG GAG AAC CTG ATG       264
Glu Ile Phe Phe Thr Val Ser Ile Val Gly Val Leu Glu Asn Leu Met
    30                  35                  40

GTC CTT CTG GCT GTG GCC AAG AAT AAG AGT CTT CAG TCG CCC ATG TAC       312
Val Leu Leu Ala Val Ala Lys Asn Lys Ser Leu Gln Ser Pro Met Tyr
45                  50                  55                  60

TTT TTC ATC TGC AGC TTG GCT ATT TCC GAT ATG CTG GGG AGC CTG TAC       360
Phe Phe Ile Cys Ser Leu Ala Ile Ser Asp Met Leu Gly Ser Leu Tyr
                65                  70                  75

AAG ATT TTG GAA AAC GTT CTG ATC ATG TTC AAA AAC ATG GGT TAC CTC       408
Lys Ile Leu Glu Asn Val Leu Ile Met Phe Lys Asn Met Gly Tyr Leu
            80                  85                  90

GAG CCT CGA GGC AGT TTT GAA AGC ACA GCA GAT GAT GTG GTG GAC TCC       456
Glu Pro Arg Gly Ser Phe Glu Ser Thr Ala Asp Asp Val Val Asp Ser
        95                 100                 105

CTG TTC ATC CTC TCC CTT CTC GGC TCC ATC TGC AGC CTG TCT GTG ATT       504
Leu Phe Ile Leu Ser Leu Leu Gly Ser Ile Cys Ser Leu Ser Val Ile
    110                 115                 120

GCC GCT GAC CGC TAC ATC ACA ATC TTC CAC GCT CTG CAG TAC CAC CGC       552
Ala Ala Asp Arg Tyr Ile Thr Ile Phe His Ala Leu Gln Tyr His Arg
125                 130                 135                 140

ATC ATG ACC CCC GCA CCG TGC CCT CGT CAT CTG ACG GTC CTC TGG GCA       600
Ile Met Thr Pro Ala Pro Cys Pro Arg His Leu Thr Val Leu Trp Ala
                145                 150                 155

GGC TGC ACA GGC AGT GGC ATT ACC ATC GTG ACC TTC TCC CAT CAC GTC       648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC       696
Pro Thr Val Ile Ala Phe Thr Ala Leu Phe Pro Leu Met Leu Ala Phe
        175                 180                 185
```

Figure 4B

```
ATC CTG TGC CTC TAC GTG CAC ATG TTC CTG CTG GCC CGC TCC CAC ACC        744
Ile Leu Cys Leu Tyr Val His Met Phe Leu Leu Ala Arg Ser His Thr
    190                 195                 200

AGG AGG ACC CCC TCC CTT CCC AAA GCC AAC ATG AGA GGG GCC GTC ACA        792
Arg Arg Thr Pro Ser Leu Pro Lys Ala Asn Met Arg Gly Ala Val Thr
205                 210                 215                 220

CTG ACT GTC CTG CTC GGG GTC TTC ATT TTC TGT TGG GCA CCC TTT GTC        840
Leu Thr Val Leu Leu Gly Val Phe Ile Phe Cys Trp Ala Pro Phe Val
                225                 230                 235

CTT CAT GTC CTC TTG ATG ACA TTC TGC CCA GCT GAC CCC TAC TGT GCC        888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT        936
Cys Tyr Met Ser Leu Phe Gln Val Asn Gly Val Leu Ile Met Cys Asn
        255                 260                 265

GCC ATC ATC GAC CCC TTC ATA TAT GCC TTT CGG AGC CCA GAG CTC AGG        984
Ala Ile Ile Asp Pro Phe Ile Tyr Ala Phe Arg Ser Pro Glu Leu Arg
    270                 275                 280

GTC GCA TTC AAA AAG ATG GTT ATC TGC AAC TGT TAC CAG TAGAATGATT        1033
Val Ala Phe Lys Lys Met Val Ile Cys Asn Cys Tyr Gln
285                 290                 295

GGTCCCTGAT TTTAGGAGCC ACAGGGATAT ACTGTCAGGG ACAGAGTAGC GTGACAGACC   1093

AACAACACTA GGACT                                                    1108
```

Figure 5A

```
GGCTGTAACT GTAGCAACCG GTGTTGGGTG GGGATGAGAA GAGACCAGAG AGAGAGAGGG      60

TCAGAGCGAC AGGGGATGAG ACAGGCTGGT CAGAGTCTGC ACTGATTGTT GGAGACGCAA     120

AGGAAAGTTT TTTCTATGTC TCCAACCTCC CCCTCCTCCC CCGTTTCTCT CTGGAGAAAC     180

TAAAATCTAG ACTGGACAGC ATCCACAAGA GAAGCACCTA GAAGAAGATT TTTTTTTCCC     240

AGCAGCTTGC TCAGGACCCT GCAGGAGCTG CAGCCGGAAC TGGTCCCGCC GATAACC        297

ATG AAC TCT TCC TGC TGC CCG TCC TCC TCT TAT CCG ACG CTG CCT AAC       345
Met Asn Ser Ser Cys Cys Pro Ser Ser Ser Tyr Pro Thr Leu Pro Asn
 1               5                  10                  15

CTC TCC CAG CAC CCT GCA GCC CCC TCT GCC AGC AAC CGG AGT GGC AGT       393
Leu Ser Gln His Pro Ala Ala Pro Ser Ala Ser Asn Arg Ser Gly Ser
            20                  25                  30

GGG TTC TGC GAG CAG GTT TTC ATC AAG CCA GAG GTC TTC CTG GCA CTG       441
Gly Phe Cys Glu Gln Val Phe Ile Lys Pro Glu Val Phe Leu Ala Leu
        35                  40                  45

GGC ATC GTC AGT CTG ATG GAA AAC ATC CTG GTG ATC CTG GCT GTG GTG       489
Gly Ile Val Ser Leu Met Glu Asn Ile Leu Val Ile Leu Ala Val Val
    50                  55                  60

AGG AAC GGC AAC CTG CAC TCC CCC ATG TAC TTC TTC CTG CTG AGC CTG       537
Arg Asn Gly Asn Leu His Ser Pro Met Tyr Phe Phe Leu Leu Ser Leu
 65                 70                  75                  80

CTG CAG GCC GAC ATG CTG GTG AGC CTG TCC AAC TCC CTG GAG ACC ATC       585
Leu Gln Ala Asp Met Leu Val Ser Leu Ser Asn Ser Leu Glu Thr Ile
                85                  90                  95

ATG ATC GTG GTT ATC AAC AGC GAC TCC CTG ACC TTG GAG GAC CAA TTC       633
Met Ile Val Val Ile Asn Ser Asp Ser Leu Thr Leu Glu Asp Gln Phe
            100                 105                 110

ATC CAG CAC ATG GAC AAC ATC TTC GAC TCT ATG ATC TGC ATC TCC CTG       681
Ile Gln His Met Asp Asn Ile Phe Asp Ser Met Ile Cys Ile Ser Leu
        115                 120                 125

GTG GCC TCC ATC TGC AAC CTC CTG GCC ATC GCC GTG GAC AGG TAC GTC       729
Val Ala Ser Ile Cys Asn Leu Leu Ala Ile Ala Val Asp Arg Tyr Val
    130                 135                 140

ACC ATC TTC TAT GCC CTC CGT TAC CAC AGC ATC ATG ACG GTT AGG AAA       777
Thr Ile Phe Tyr Ala Leu Arg Tyr His Ser Ile Met Thr Val Arg Lys
145                 150                 155                 160
```

Figure 5B

```
GCC CTC TCC TTG ATC GTG GCC ATC TGG GTC TGC TGT GGC ATC TGC GGC        825
Ala Leu Ser Leu Ile Val Ala Ile Trp Val Cys Cys Gly Ile Cys Gly
                165                 170                 175

GTG ATG TTC ATC GTC TAC TCC GAG AGC AAG ATG GTC ATC GTG TGC CTC        873
Val Met Phe Ile Val Tyr Ser Glu Ser Lys Met Val Ile Val Cys Leu
            180                 185                 190

ATC ACC ATG TTC TTC GCC ATG GTG CTC CTC ATG GGC ACC CTG TAC ATC        921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG        969
His Met Phe Leu Phe Ala Arg Leu His Val Gln Arg Ile Ala Ala Leu
    210                 215                 220

CCA CCT GCT GAC GGG GTA GCC CCG CAG CAG CAC TCG TGC ATG AAG GGG       1017
Pro Pro Ala Asp Gly Val Ala Pro Gln Gln His Ser Cys Met Lys Gly
225                 230                 235                 240

GCC GTC ACC ATC ACC ATC CTG CTG GGG GTT TTC ATC TTC TGC TGG GCG       1065
Ala Val Thr Ile Thr Ile Leu Leu Gly Val Phe Ile Phe Cys Trp Ala
                245                 250                 255

CCT TTC TTC CTC CAC CTG GTC CTC ATC ATC ACC TGC CCC ACC AAC CCC       1113
Pro Phe Phe Leu His Leu Val Leu Ile Ile Thr Cys Pro Thr Asn Pro
            260                 265                 270

TAC TGC ATC TGC TAC ACG GCG CAC TTC AAC ACC TAC CTG GTT CTC ATC       1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG       1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG       1257
Glu Leu Arg Asn Thr Phe Lys Glu Ile Leu Cys Gly Cys Asn Gly Met
305                 310                 315                 320

AAC GTG GGC TAGGAACCCC CGAGGAGGTG TTCCACGGCT AGCCAAGAGA               1306
Asn Val Gly

GAAAAGCAAT GCTCAGGTGA GACACAGAAG GG                                   1338
```

Figure 6A

```
AGCTTCCGAG AGGCAGCCGA TGTGAGCATG TGCGCACAGA TTCGTCTCCC AATGGCATGG      60

CAGCTTCAAG GAAAATTATT TTGAACAGAC TTGAATGCAT AAGATTAAAG TTAAAGCAGA     120

AGTGAGAACA AGAAAGCAAA GAGCAGACTC TTTCAACTGA GAATGAATAT TTTGAAGCCC     180

AAGATTTTAA AGTGATGATG ATTAGAGTCG TACCTAAAAG AGACTAAAAA CTCCATGTCA     240

AGCTCTGGAC TTGTGACATT TACTCACAGC AGGCATGGCA ATTTTAGCCT CACAACTTTC     300

AGACAGATAA AGACTTGGAG GAAATAACTG AGACGACTCC CTGACCCAGG AGGTTAAATC     360

AATTCAGGGG GACACTGGAA TTCTCCTGCC AGC ATG GTG AAC TCC ACC CAC CGT      414
                                     Met Val Asn Ser Thr His Arg
                                      1               5

GGG ATG CAC ACT TCT CTG CAC CTC TGG AAC CGC AGC AGT TAC AGA CTG       462
Gly Met His Thr Ser Leu His Leu Trp Asn Arg Ser Ser Tyr Arg Leu
        10                  15                  20

CAC AGC AAT GCC AGT GAG TCC CTT GGA AAA GGC TAC TCT GAT GGA GGG       510
His Ser Asn Ala Ser Glu Ser Leu Gly Lys Gly Tyr Ser Asp Gly Gly
    25                  30                  35

TGC TAC GAG CAA CTT TTT GTC TCT CCT GAG GTG TTT GTG ACT CTG GGT       558
Cys Tyr Glu Gln Leu Phe Val Ser Pro Glu Val Phe Val Thr Leu Gly
 40                 45                  50                  55

GTG ATC AGC TTG TTG GAG AAT ATC TTA GTG ATT GTG GCA ATA GCC AAG       606
Val Ile Ser Leu Leu Glu Asn Ile Leu Val Ile Val Ala Ile Ala Lys
                60                  65                  70

AAC AAG AAT CTG CAT TCA CCC ATG TAC TTT TTC ATC TGC AGC TTG GCT       654
Asn Lys Asn Leu His Ser Pro Met Tyr Phe Phe Ile Cys Ser Leu Ala
            75                  80                  85

GTG GCT GAT ATG CTG GTG AGC GTT TCA AAT GGA TCA GAA ACC ATT ATC       702
Val Ala Asp Met Leu Val Ser Val Ser Asn Gly Ser Glu Thr Ile Ile
        90                  95                  100

ATC ACC CTA TTA AAC AGT ACA GAT ACG GAT GCA CAG AGT TTC ACA GTG       750
Ile Thr Leu Leu Asn Ser Thr Asp Thr Asp Ala Gln Ser Phe Thr Val
    105                 110                 115

AAT ATT GAT AAT GTC ATT GAC TCG GTG ATC TGT AGC TCC TTG CTT GCA       798
Asn Ile Asp Asn Val Ile Asp Ser Val Ile Cys Ser Ser Leu Leu Ala
120                 125                 130                 135

TCC ATT TGC AGC CTG CTT TCA ATT GCA GTG GAC AGG TAC TTT ACT ATC       846
Ser Ile Cys Ser Leu Leu Ser Ile Ala Val Asp Arg Tyr Phe Thr Ile
                140                 145                 150
```

Figure 6B

```
TTC TAT GCT CTC CAG TAC CAT AAC ATT ATG ACA GTT AAG CGG GTT GGG      894
Phe Tyr Ala Leu Gln Tyr His Asn Ile Met Thr Val Lys Arg Val Gly
            155                 160                 165

ATC AGC ATA AGT TGT ATC TGG GCA GCT TGC ACG GTT TCA GGC ATT TTG      942
Ile Ser Ile Ser Cys Ile Trp Ala Ala Cys Thr Val Ser Gly Ile Leu
        170                 175                 180

TTC ATC ATT TAC TCA GAT AGT AGT GCT GTC ATC ATC TGC CTC ATC ACC      990
Phe Ile Ile Tyr Ser Asp Ser Ser Ala Val Ile Ile Cys Leu Ile Thr
    185                 190                 195

ATG TTC TTC ACC ATG CTG GCT CTC ATG GCT TCT CTC TAT GTC CAC CTG     1038
Met Phe Phe Thr Met Leu Ala Leu Met Ala Ser Leu Tyr Val His Leu
200                 205                 210                 215

TTC CTG ATG GCC AGG CTT CAC ATT AAG AGG ATT GCT GTC CTC CCC GGC     1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG     1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC     1182
Thr Ile Leu Ile Gly Val Phe Val Val Cys Trp Ala Pro Phe Phe Leu
        250                 255                 260

CAC TTA ATA TTC TAC ATC TCT TGT CCT CAG AAT CCA TAT TGT GTG TGC     1230
His Leu Ile Phe Tyr Ile Ser Cys Pro Gln Asn Pro Tyr Cys Val Cys
    265                 270                 275

TTC ATG TCT CAC TTT AAC TTG TAT CTC ATA CTG ATC ATG TGT AAT TCA     1278
Phe Met Ser His Phe Asn Leu Tyr Leu Ile Leu Ile Met Cys Asn Ser
280                 285                 290                 295

ATC ATC GAT CCT CTG ATT TAT GCA CTC CGG AGT CAA GAA CTG AGG AAA     1326
Ile Ile Asp Pro Leu Ile Tyr Ala Leu Arg Ser Gln Glu Leu Arg Lys
                300                 305                 310

ACC TTC AAA GAG ATC ATC TCT TCC TAT CCC CTG GGA GGC CTT TGT GAC     1374
Thr Phe Lys Glu Ile Ile Ser Ser Tyr Pro Leu Gly Gly Leu Cys Asp
            315                 320                 325

TTG TCT AGC AGA TAT TAAATGGGGA CAGAGCACGC AATATAGGAA CATCCATAAG     1429
Leu Ser Ser Arg Tyr
        330

AGACTTTTTC ACTCTTACCC TACCTGAATA TTCTACTTCT GCAACAGCTT TCTCTTCCGT   1489

GTAGGGTACT GGTTGAGATA TCCATTGTGT AAATTTAAGC CTATGATTTT TAATGAGAAA   1549
```

Figure 6C

AAATGCCCAG TCTCTGTATT ATTTCCAATC TCATGCTACT TTTTTGGCCA TAAAATATGA 1609

ATCTATGTTA TAGGTTGTAG GCACTGTGGA TTTACAAAAA GAAAAGTCCT TATTAAAAGC 1669

```
ATG AAC TCC TCC TCC ACC CTG ACT GTA TTG AAT CTT ACC CTG AAC GCC      48
Met Asn Ser Ser Ser Thr Leu Thr Val Leu Asn Leu Thr Leu Asn Ala
 1               5                  10                  15

TCA GAG GAT GGC ATT TTA GGA TCA AAT GTC AAG AAC AAG TCT TTG GCC      96
Ser Glu Asp Gly Ile Leu Gly Ser Asn Val Lys Asn Lys Ser Leu Ala
             20                  25                  30

TGT GAA GAA ATG GGC ATT GCC GTG GAG GTG TTC CTG ACC CTG GGT CTC     144
Cys Glu Glu Met Gly Ile Ala Val Glu Val Phe Leu Thr Leu Gly Leu
         35                  40                  45

GTC AGC CTC TTA GAG AAC ATC CTG GTC ATT GGG GCC ATA GTA AAG AAC     192
Val Ser Leu Leu Glu Asn Ile Leu Val Ile Gly Ala Ile Val Lys Asn
     50                  55                  60

AAA AAC CTG CAC TCA CCC ATG TAC TTC TTT GTG GGC AGC TTA GCC GTG     240
Lys Asn Leu His Ser Pro Met Tyr Phe Phe Val Gly Ser Leu Ala Val
 65                  70                  75                  80

GCC GAC ATG CTG GTG AGC ATG TCC AAT GCC TGG GAG ACT GTC ACC ATA     288
Ala Asp Met Leu Val Ser Met Ser Asn Ala Trp Glu Thr Val Thr Ile
                 85                  90                  95

TAC TTG CTA AAT AAT AAA CAC CTG GTG ATA GCC GAC ACC TTT GTG CGA     336
Tyr Leu Leu Asn Asn Lys His Leu Val Ile Ala Asp Thr Phe Val Arg
             100                 105                 110

CAC ATC GAC AAC GTG TTC GAC TCC ATG ATC TGC ATC TCT GTG GTG GCC     384
His Ile Asp Asn Val Phe Asp Ser Met Ile Cys Ile Ser Val Val Ala
         115                 120                 125

TCG ATG TGC AGT TTG CTG GCC ATT GCG GTG GAT AGG TAC ATC ACC ATC     432
Ser Met Cys Ser Leu Leu Ala Ile Ala Val Asp Arg Tyr Ile Thr Ile
     130                 135                 140

TTC TAT GCC TTG CGC TAC CAC CAC ATC ATG ACC GCG AGG CGC TCG GGG     480
Phe Tyr Ala Leu Arg Tyr His His Ile Met Thr Ala Arg Arg Ser Gly
145                 150                 155                 160

GTG ATC ATC GCC TGC ATT TGG ACC TTC TGC ATA AGC TGC GGC ATT GTT     528
Val Ile Ile Ala Cys Ile Trp Thr Phe Cys Ile Ser Cys Gly Ile Val
                165                 170                 175

TTC ATC ATC TAC TAT GAG TCC AAG TAT GTG ATC ATT TGC CTC ATC TCC     576
Phe Ile Ile Tyr Tyr Glu Ser Lys Tyr Val Ile Ile Cys Leu Ile Ser
            180                 185                 190

ATG TTC TTC ACC ATG CTG TTC TTC ATG GTG TCT CTG TAT ATA CAC ATG     624
Met Phe Phe Thr Met Leu Phe Phe Met Val Ser Leu Tyr Ile His Met
        195                 200                 205
```

Figure 7B

```
TTC CTC CTG GCC CGG AAC CAT GTC AAG CGG ATA GCA GCT TCC CCC AGA     672
Phe Leu Leu Ala Arg Asn His Val Lys Arg Ile Ala Ala Ser Pro Arg
    210                 215                 220

TAC AAC TCC GTG AGG CAA AGG ACC AGC ATG AAG GGG GCT ATT ACC CTC     720
Tyr Asn Ser Val Arg Gln Arg Thr Ser Met Lys Gly Ala Ile Thr Leu
225                 230                 235                 240

ACC ATG CTA CTG GGG ATT TTC ATT GTC TGC TGG TCT CCC TTC TTT CTT     768
Thr Met Leu Leu Gly Ile Phe Ile Val Cys Trp Ser Pro Phe Phe Leu
                245                 250                 255

CAC CTT ATC TTA ATG ATC TCC TGC CCT CAG AAC GTC TAC TGC TCT TGC     816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC     864
Phe Met Ser Tyr Phe Asn Met Tyr Leu Ile Leu Ile Met Cys Asn Ser
        275                 280                 285

GTG ATC GAT CCT CTC ATC TAC GCC CTC CGC AGC CAA GAG ATG CGG AGG     912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG     960
Thr Phe Lys Glu Ile Val Cys Cys His Gly Phe Arg Arg Pro Cys Arg
305                 310                 315                 320

CTC CTT GGC GGG TAT TAA                                             978
Leu Leu Gly Gly Tyr
                325
```

hMC4-R hMC3-R hMC4-R

METHODS AND REAGENTS FOR DISCOVERING AND USING MAMMALIAN MELANOCORTIN RECEPTOR AGONISTS AND ANTAGONISTS TO MODULATE FEEDING BEHAVIOR IN ANIMALS

This application is a divisional of U.S. patent application, Ser. No. 08/706,281, filed Sep. 4, 1996 now U.S. Pat. No. 6,100,048, which is a CIP of Ser. No. 08/466,906, filed Jun. 6, 1993 (now U.S. Pat. No. 5,849,871); which is a divisional of Ser. No. 07/866,979 filed Apr. 10, 1992 (now U.S. Pat. No. 5,537,347) and which is a C-I-P of Ser. No. 08/478,992 filed Jun. 7, 1995 (now U.S. Pat. No. 5,773,229) which is a divisional of Ser. No. 08/077,675 filed Jun. 15, 1993 (now U.S. Pat. No. 5,554,729) which is a divisional of Ser. No. 07/866,560 filed Apr. 10, 1992 (now U.S. Pat. No. 5,280, 112) and which is a C-I-P of Ser. No. 08/044,812 filed Apr. 8, 1993 (now U.S. Pat. No. 5,837,521).

This invention was made with government support under R29DK41921, R01DK43859, P01DK44239, AR42415 and HD30236 by the National Institutes of Health. The government has certain rights in the invention.

BACKGROUND OF THE INVENTION

1. Field of the Invention

The present invention relates to the cloning, expression and functional characterization of mammalian melanocortin receptor genes. The invention provides nucleic acid encoding mammalian melanocortin receptors, recombinant expression constructs comprising said nucleic acid, and mammalian cells into which said recombinant expression constructs have been introduced, and that express functional mammalian melanocortin receptors. The invention also provides a panel of such transformed mammalian cells expressing melanocortin receptors for screening compounds for receptor agonist and antagonist activity. The invention provides methods, for using such panels of melanocortin receptor-expressing mammalian cells to specifically detect and identify agonists and antagonists for each melanocortin receptor, as well as patterns of agonist and antagonist activity of said compounds for the class of melanocortin receptors. Such screening methods provide a means for identifying compounds with patterns of melanocortin agonist and antagonist activity which is associated with the capacity to influence or modify physiological function and behavior, particularly metabolism and feeding behavior.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well understood roles in control of melanocyte and adrenocortical function, respectively. Both of these hormones are also found in a variety of forms with unknown functions, for example, γ-melanocyte stimulating hormone (γMSH), which has little or no ability to stimulate pigmentation (Ling et al., 1979, *Life Sci.* 25: 1773–1780; Slominski et al., 1992, *Life Sci.* 50: 1103–1108). A melanocortin receptor gene specific for each of the αMSH, ACTH and γMSH hormones has been discovered by some of the present inventors (see U.S. Pat. Nos. 5,280,112, 5,532,347 and U.S. application Ser. No. 08/044,812, incorporated by reference herein). In addition, two other melanocortin receptor genes have been discovered by some of the present inventors (see Lu et al, 1994, *Nature* 371: 799–802; Mountjoy et al, 1994, *Molec. Endocrinol.* 8: 1298–1308) and others (see Gantz et al., 1993, *J. Biol. Chem.* 268: 15174–15179 and Labbe et al., 1994, *Biochem.* 33: 4543–4549).

Along with the well-recognized activities of αMSH in melanocytes and ACTH in adrenal and pituitary glands, the melanocortin peptides also have a diverse array of biological activities in other tissues, including the brain and immune system, and bind to specific receptors in these tissues with a distinct pharmacology (see, Hanneman et al., in *Peptide Hormone as Prohormones*, G. Martinez, ed. (Ellis Horwood Ltd.: Chichester, UK) pp. 53–82; DeWied & Jolles, 1982, *Physiol. Rev.* 62: 976–1059 for reviews). A complete understanding of these peptides and their diverse biological activities requires the isolation and characterization of their corresponding receptors. Some biochemical studies have been reported in the prior art.

Shimuze, 1985, *Yale J. Biol. Med.* 58: 561–570 discusses the physiology of melanocyte stimulating hormone.

Tatro & Reichlin, 1987, *Endocrinology* 121: 1900–1907 disclose that MSH receptors are widely distributed in rodent tissues.

Sola et al., 1989, *J. Biol. Chem.* 264: 14277–14280 disclose the molecular weight characterization of mouse and human MSH receptors linked to radioactively and photoaffinity labeled MSH analogues.

Siegrist et al., 1991, *J. Receptor Res.* 11: 323–331 disclose the quantification of receptors on mouse melanoma tissue by receptor autoradiography.

Cone & Mountjoy, U.S. patent application Ser. No. 07/866,979, filed Apr. 10, 1992, disclose the isolation of human and mouse α-MSH receptor genes and uses thereof (incorporated herein by reference).

Cone & Mountjoy, U.S. patent application Ser. No. 07/866,560, filed Apr. 10, 1992, disclose the isolation of human and bovine ACTH receptor genes and uses thereof (incorporated herein by reference).

Mountjoy et al., 1992, *Science* 257: 1248–1251 disclose the isolation of cDNAs encoding mammalian ACTH and MSH receptor proteins.

POMC neurons are present in only two regions of the brain, the arcuate nucleus of the hypothalamus, and the nucleus of the solitary tract of the brain stem. Neurons from both sites project to a number of hypothalamic nuclei known to be important in feeding behavior, including the paraventricular nucleus, lateral hypothalamic area, and ventromedial hypothalamic nucleus. While previous reports have claimed both stimulatory and inhibitory effects of α-MSH on feeding behavior (see Shimizu et al., 1989, *Life Sci.* 45: 543–552; Tsujii et al., 1989, *Brian Res. Bull.* 23: 165–169), knowledge of specific melanocortin receptors, their location within the central nervous system and the necessary pharmacological tools were not sufficiently developed at that time to allow the resolution of this issue. The present inventors have shown herein that a novel antagonist of the MC-3 and MC-4 melanocortin receptors can substantially increase food consumption in animals engaged in normal or fast-induced feeding behavior. This is consistent with expression of both MC-3 and MC-4 receptor mRNAs at these sites in in situ hybridization studies (Roselli-Rehfuss et al., 1993, *Proc. Natl. Acad. Sci. USA* 90: 8856–8860; Mountjoy et al., 1994, *Molec. Endocrinol.* 8: 1298–1308). Moreover, the regulation of arcuate nucleus POMC gene expression is consistent with an inhibitory role for POMC in feeding behavior. POMC mRNA levels are decreased following a fast (Bergendahl et al., 1992, *Neuroendocrinol.* 56: 913–920; Brady et al., 1990, *Neuroendocrinol.* 52: 441–447), and a significant diurnal variation in POMC mRNA levels in the arcuate nucleus is seen in rat, with the nadir occurring around the onset of nighttime feeding at 1800 hrs (Steiner et al., 1994, *FASEB J.* 8: 479–488).

Thus, the experimental evidence indicates that POMC neurons play an important role in tonic inhibition of feeding behavior, wherein obesity results from a chronic disruption of this inhibitory tone by antagonism of central melanocortin receptors in at least one animal model (agouti).

These results reveal for the first time a need in the art for a means for characterizing mammalian melanocortin receptor agonists and antagonists in vitro for the development of compounds that affect feeding behavior in animals.

SUMMARY OF THE INVENTION

The present invention provides a biological screening system for identifying and characterizing compounds that are agonists or antagonists of mammalian melanocortin receptors. The biological screening system of the invention comprises a panel of transformed mammalian cells comprising a recombinant expression construct encoding a mammalian melanocortin receptor, and expressing said receptor thereby. The invention provides such a panel of transformed mammalian cells wherein the panel comprises cells expressing each of type of mammalian melanocortin receptor. Thus, the invention also provides nucleic acid encoding mammalian melanocortin receptors, recombinant expression constructs comprising said nucleic acid, and mammalian cells into which said recombinant expression constructs have been introduced, and that express functional mammalian melanocortin receptors. Methods for using such panels of melanocortin receptor-expressing mammalian cells to specifically detect and identify agonists and antagonists for each melanocortin receptor, as well as patterns of agonist and antagonist activity of said compounds for the class of melanocortin receptors, are also provided. Such screening methods provide a means for identifying compounds with patterns of melanocortin agonist and antagonist activity which is associated with the capacity to influence or modify metabolism and behavior in an animal, particularly feeding behavior.

Thus, the invention provides in a first aspect a biological screening panel for determining the melanocortin receptor agonist/antagonist profile of a test compound. The panel comprises a first mammalian cell comprising a recombinant expression construct encoding a mammalian melanocortin receptor that is the α-MSH (MC-1) receptor. The panel also comprises a second mammalian cell comprising a recombinant expression construct encoding a mammalian melanocortin receptor that is the ACTH (MC-2) receptor. The panel also comprises a third mammalian cell comprising a recombinant expression construct encoding a mammalian melanocortin receptor that is the MC-3 receptor. The panel also comprises a fourth mammalian cell comprising a recombinant expression construct encoding a mammalian melanocortin receptor that is the MC-4 receptor. The panel also comprises a fifth mammalian cell comprising a recombinant expression construct encoding a mammalian melanocortin receptor that is the MC-5 receptor. As provided by the invention, each mammalian cell expresses the melanocortin receptor encoded by the recombinant expression construct comprising said cell.

In preferred embodiments, the melanocortin receptors encoded by the recombinant expression constructs comprising the transformed mammalian cells comprising the panel are mouse MC-1 receptor (SEQ ID Nos.:3 and 4); human MC-I receptor (SEQ ID Nos.:5 and 6), human MC-2 (ACTH) receptor (SEQ ID Nos.:7 and 8), bovine MC-2 receptor (SEQ ID Nos.:9 and 10), rat MC-3 receptor (SEQ ID Nos.:11 and 12), human MC-4 receptor (SEQ ID Nos.:15 and 16) and human MC-5 receptor (SEQ ID Nos.:17 and 18).

In a second aspect, the invention provides a method for using the melanocortin receptor panel to identify and characterize test compounds as melanocortin receptor agonists and/or antagonists. In this embodiment, the method provided by the invention identifies a melanocortin receptor agonist, and comprises the steps of contacting each of the cells of the panel with a test compound to be characterized as an agonist of a mammalian melanocortin receptor and detecting binding of the test compound to each of the mammalian melanocortin receptors by assaying for a metabolite produced in the cells that bind the compound. In a preferred embodiment, the detected metabolite is cAMP.

In a preferred embodiment of this method, each of the cells of the panel of mammalian cells expressing mammalian melanocortin receptors further comprises a recombinant expression construct encoding a cyclic AMP responsive element (CRE) transcription factor binding site that is operatively linked to a nucleic acid sequence encoding a protein capable of producing a detectable metabolite. In preferred embodiments, said protein is β-galactosidase, most preferably encoded by a nucleic acid comprising the recombinant expression construct identified as pCRE/β-galactosidase (as disclosed in Chen et al., 1994, *Analyt. Biochem.* 226: 349–354). As provided by the invention, expression of the protein that produces the detectable metabolite is dependent on binding of the test compound to the melanocortin receptor expressed by each cell in the panel and the intracellular production of cAMP as a result. In this embodiment, cAMP production results in expression of a protein capable of producing a detectable metabolite, the protein most preferably being β-galactosidase. In preferred embodiments, the detectable metabolite absorbs light to produce a colored product. Thus, this embodiment of the invention provides a panel of melanocortin receptor-expressing cells whereby melanocortin hormone binding results in the production of a colored product in proportion to the extent of cAMP production in the cell as a result of hormone receptor binding.

In another embodiment of this aspect of the invention is provided a method for characterizing a compound as an antagonist of a mammalian melanocortin receptor. In this embodiment, the method comprises the steps of contacting each of the cells of the panel with an agonist of the mammalian melanocortin receptor in an amount sufficient to produce a detectable amount of a metabolite produced in the cells that bind the agonist, in the presence or absence of a test compound to be characterized as an antagonist of a mammalian melanocortin receptor, and detecting the amount of the metabolite produced in each cell in the panel in the presence of the test compound with the amount of the metabolite produced in each cell in the panel in the absence. As provided by the assay, inhibition of the production of the detectable metabolite is used as an indication that the tested compound is a melanocortin receptor antagonist, which is further characterized quantitatively by the extent of said inhibition.

In a preferred embodiment of this method, each of the cells of the panel of mammalian cells expressing mammalian melanocortin receptors further comprises a recombinant expression construct encoding a cyclic AMP responsive element (CRE) transcription factor binding site that is operatively linked to a nucleic acid sequence encoding a protein capable of producing a detectable metabolite. In preferred embodiments, said protein is β-galactosidase, most preferably encoded by a nucleic acid comprising the recombinant expression construct identified as pCRE/β-galactosidase. As provided by the invention, expression of the protein that produces the detectable, metabolite is dependent on binding of the test compound to the melanocortin receptor expressed by each cell in the panel. In preferred embodiments, the detectable metabolite absorbs light to produce a colored product. Thus, this embodiment of the invention provides a panel of melanocortin receptor-expressing cells whereby melanocortin hormone binding results in the production of a colored product in proportion to the extent of cAMP production in the cell as a result of hormone receptor binding.

The invention also provides melanocortin receptor agonists identified by the methods and using the screening panel of the invention. In preferred embodiments, the agonist is an agonist of the MC-3 mammalian melanocortin receptor. In preferred embodiments, the agonist is an agonist of the MC-4 mammalian melanocortin receptor.

The invention provides melanocortin receptor antagonists identified by the methods and using the screening panel of the invention. In preferred embodiments, the antagonist is an antagonist of the MC-3 mammalian melanocortin receptor. In preferred embodiments, the antagonist is an antagonist of the MC-4 mammalian melanocortin receptor.

The invention also provides methods for characterizing mammalian melanocortin receptor agonists for the capacity to modify or influence metabolism and feeding behavior in an animal. In a first aspect, the invention provides a method for characterizing melanocortin receptor MC-3 or MC-4 agonists as inhibitors of feeding behavior in an animal, the method comprising the steps of providing food to an animal that has been deprived of food for at least 12 hours, with or without administering to the animal an MC-3 or MC-4 receptor agonist of the invention, and comparing the amount of food eaten by the animal after administration of the MC-3 or MC-4 receptor agonist with the amount of food eaten by the animal without administration of the MC-3 or MC-4 receptor agonist.

In another aspect, the invention provides a method for characterizing a melanocortin MC-3 or MC-4 receptor antagonist as a stimulator of feeding behavior in an animal. In this embodiment, the method comprises the steps of providing food to an animal not deprived of food for at least 12 hours, with or without administering to the animal an MC-3 or MC-4 receptor antagonist, immediately prior to the onset of darkness or nighttime, and comparing the amount of food eaten by the animal after administration of the MC-3 or MC-4 receptor antagonist with the amount of food eaten by the animal without administration of the MC-3 or MC-4 receptor antagonist.

Thus, the invention also provides methods for using certain of the melanocortin receptor agonists and antagonists for modifying feeding behavior in an animal. In a first aspect, the invention provides a method for stimulating feeding in an animal, the method comprising administering to the animal an MC-3 or MC-4 receptor antagonist. In a preferred embodiment, the antagonists are administered systemically. In additional embodiments, the antagonists are administered intracerebroventricularly.

In another aspect, the invention provides a method for inhibiting feeding in an animal, the method comprising administering to the animal an MC-3 or MC-4 receptor agonist. In a preferred embodiment, the agonists are administered systemically. In additional embodiments, the agonists are administered intracerebroventricularly. In yet another aspect, the invention provides mammalian melanocortin receptor agonists having the general formula:

A-B-C-D-E-F-G-amide wherein A is an aliphatic amino acid residue, including for example Leu, Ile, Nle and Met, as well as analogues and substituted derivatives thereof; B is an acidic amino acid residue, including for example Asp and Glu; C is a basic amino acid residue, such as His; D is an aromatic amino acid residue having a D-conformation, including D-Phe, D-Tyr and substituted derivatives thereof; E is. a basic amino acid residue, for. example Arg, Lys, homoArg, homoLys, and analogues or substituted derivatives thereof; F is Trp or substituted derivatives thereof; and G is Lys, homoLys or a substituted derivative thereof. In the peptide embodiments of the melanocortin receptor agonists of the invention, the peptide is cyclized by the formation of an amide bond between the side chain carboxyl group of the Asp or Glu residue at position B in the peptide, and the side chain amino group of the Lys or homoLys residue at position G. In preferred embodiments, the melanocortin receptor agonists of the invention are agonists of the MC-3 or MC-4 receptor.

The invention also provides mammalian melanocortin receptor antagonists having the general formula:

A-B-C-D-E-F-G-amide wherein A is an aliphatic amino acid residue, including for example Leu, Ile, Nle and Met, as well as analogues and substituted derivatives thereof; B is an acidic amino acid residue, including for example Asp and Glu; C is a basic amino acid residue, such as His; D is an aromatic amino acid residue having D-conformation, including D-Nal and substituted derivatives thereof; E is a basic amino acid residue, for example Arg, Lys, homoArg, homoLys, and analogues or substituted derivatives thereof; F is Trp or substituted derivatives thereof; and G is Lys, homoLys or a substituted derivative thereof. In the peptide embodiments of the melanocortin receptor antagonists of the invention, the peptide is cyclized by the formation of an amide bond between the side chain carboxyl group of the Asp or Glu residue at position B in the peptide, and the side chain amino group of the Lys or homoLys residue at position G. In preferred embodiments, the melanocortin receptor antagonists of the invention are agonists of the MC-3 or MC-4 receptor.

It is an advantage of the present invention that it provides an in vitro screening method for characterizing compounds having melanocortin receptor activities that relate to feeding behavior in animals. Specifically, the invention advantageously provides means and methods for identifying compounds having melanocortin receptor agonist and/or antagonist activity that have been associated with either stimulating or inhibiting feeding behavior when administered to an animal. The invention thus provides an economical first step in screening compounds for the capacity to affect feeding behavior, including synthetic, peptidomimetic or organomimetic derivatives of melanocortin receptor agonists or antagonists as disclosed herein or elsewhere.

Specific preferred embodiments of the present invention will become evident from the following more detailed description of certain preferred embodiments and the claims.

DESCRIPTION OF THE DRAWINGS

FIGS. 1A and 1B illustrate the nucleotide (SEQ ID No.:3) and amino acid (SEQ ID No.:4) sequence of the mouse melanocyte stimulating hormone receptor gene.

FIGS. 2A and 2B illustrate the nucleotide (SEQ ID No.:5) and amino acid (SEQ ID No.:6) sequence of the human melanocyte stimulating hormone receptor gene.

FIGS. 3A through 3C illustrate the nucleotide (SEQ ID No.:7) and amino acid (SEQ ID No.:8) sequence of the human adrenocorticotropic hormone receptor gene.

FIGS. 4A and 4B illustrate the nucleotide (SEQ ID No.:9) and amino acid (SEQ ID No.:10) sequence of the bovine adrenocorticotropic hormone receptor gene.

FIGS. 5A and 5B illustrate the nucleotide (SEQ ID No.:11) and amino acid (SEQ ID No.:12) sequences of the rat melanocortin-3 receptor.

FIGS. 6A through 6C illustrate the nucleotide (SEQ ID No.:15) and amino acid (SEQ ID No.:16) sequence of the human melanocortin 4 receptor gene.

FIGS. 7A and 7B illustrate the nucleotide (SEQ ID No.:17) and amino acid (SEQ ID No.:18) sequences of the rat melanocortin-5 receptor gene.

DETAILED DESCRIPTION OF THE PREFERRED EMBODIMENTS

Figure 8:
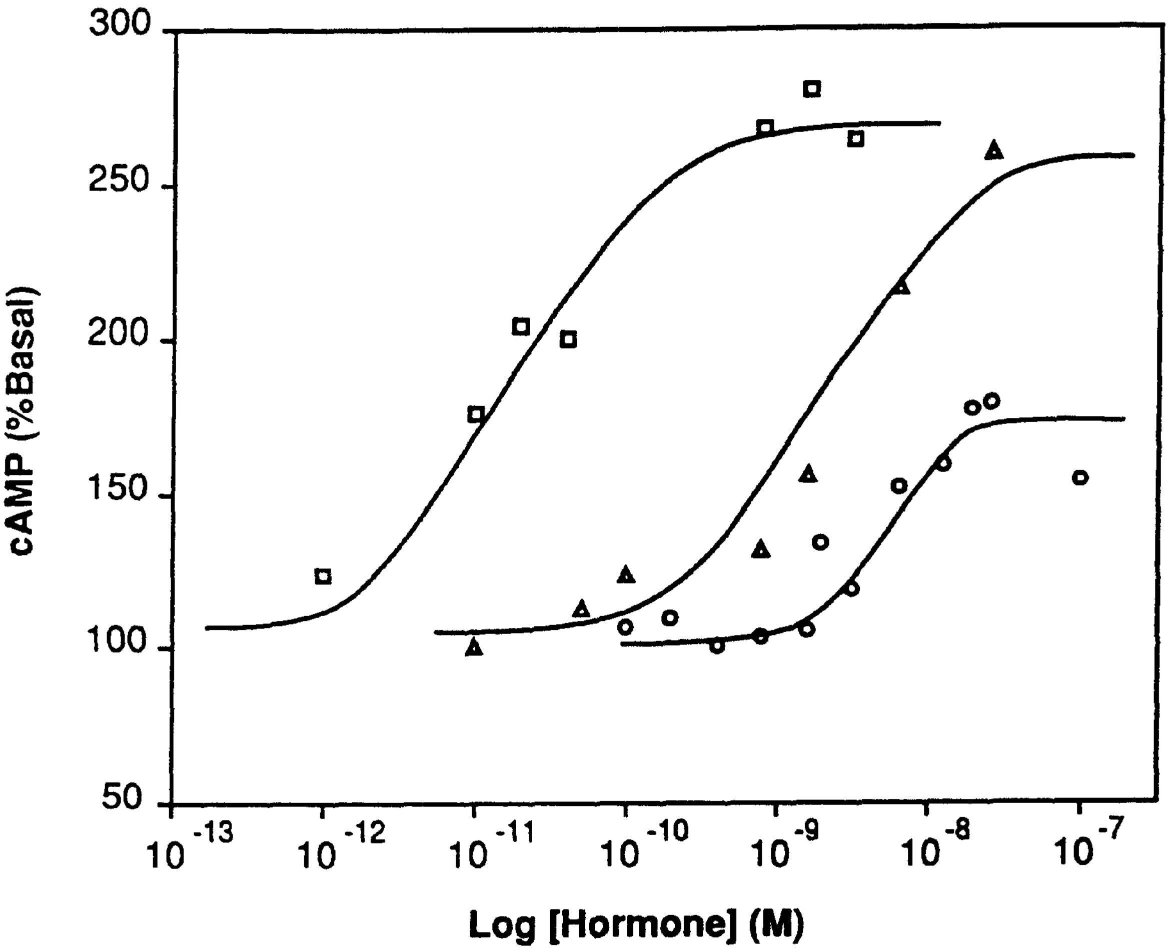
FIG. 8 shows a graph of intracellular cAMP accumulation resulting from melanocyte stimulating hormone receptor agonist binding in human 293 cells transfected with a MSH receptor-encoding recombinant expression construct.

The term "melanocortin receptor" as used herein reference to proteins having the biological activity of any of the disclosed melanocortin receptors, including the MC-1 (SEQ ID Nos.:3, 4, 5 and 6), MC-2 (ACTH; SEQ ID Nos.:7, 8, 9 and 10), MC-3 (SEQ ID Nos.:11 and 12), MC-4 (SEQ ID Nos.:15 and 16) or MC-5 (SEQ ID Nos.:17 and 18) receptors, as well as naturally-occurring and genetically-engineered allelic variations in these sequences.

Cloned nucleic acid provided by the present invention may encode MC receptor protein of any species of origin, including, for example, mouse, rat, rabbit, cat, and human, but preferably the nucleic acid provided by the invention encodes MC receptors of mammalian, most preferably rodent and human, origin.

The production of proteins such as the MC receptors from cloned genes by genetic engineering means is well known in this art. The discussion which follows is accordingly intended as an overview of this field, and is not intended to reflect the full state of the art.

DNA which encodes MC receptors may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MC receptor gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, MC receptor gene sequences may be obtained by use of the polymerase chain reaction (PCR) procedure, with the PCR oligonucleotide primers being produced from the MC receptor gene sequences provided herein. See U.S. Pat. No. 4,683,195 to Mullis et al. and U.S. Pat. No. 4,683,202 to Mullis.

MC receptor proteins may be synthesized in host cells transformed with a recombinant expression construct comprising a nucleic acid encoding each of the receptors disclosed herein. Such a recombinant expression construct can also be comprised of a vector that is a replicable DNA construct. Vectors are used herein either to amplify DNA encoding an MC receptor and/or to express DNA which encodes an MC receptor. For the purposes of this invention, a recombinant expression construct is a replicable DNA construct in which a DNA sequence encoding an MC receptor is operably linked to suitable control sequences capable of effecting the expression of the receptor in a suitable host cell. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Also specifically provided by the invention are reporter expression constructs comprising a nucleic acid encoding a protein capable of expressing a detectable phenotype, such as the production of a detectable reporter molecule, in a cell expressing the construct. Such constructs can be used for producing recombinant mammalian cell lines in which the reporter construct is stably expressed.

Most preferably, however, the reporter construct is provided and used to induce transient expression over an experimental period of from about 18 to 96 hrs in which detection of the reporter protein-produced detectable metabolite comprises an assay. Such reporter expression constructs are also provided wherein induction of expression of the reporter construct is controlled by a responsive element operatively linked to the coding sequence of the reporter protein, so that expression is induced only upon proper stimulation of the responsive element. Exemplary of such a responsive element is a cAMP responsive element (CRE), which induces expression of the reporter protein as a result of an increase in intracellular cAMP concentration. In the context of the present invention, such a stimulus is associated with melanocortin receptor binding, so that a reporter construct comprising one or more CREs is induced to express the reporter protein upon binding of a receptor agonist to a MC receptor in a recombinantly transformed mammalian cell. Production and use of such a reporter construct is illustrated below in Example 5.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNA/neo I. Transformed host cells are cells which have been transformed or transfected with recombinant expression constructs made using recombinant DNA techniques and comprising mammalian MC receptor-encoding sequences. Preferred host cells are human 293 cells. Preferred host cells for the MC-2 (ACTH) receptor are Y1 cells (subclone OS3 or Y6). Transformed host cells are chosen that ordinarily express functional MC receptor protein introduced using the recombinant expression construct. When expressed, the mammalian MC receptor protein will typically be located in the host cell membrane. See, Sambrook et al., ibid.

Cultures of cells derived from multicellular organisms are a desirable host for recombinant MC receptor protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, mouse Y1 (subclone OS3), and WI138, BHK, COS-7, CV, and MDCK cell lines. Human 293 cells are preferred.

Cells expressing mammalian MC receptor proteins made from cloned genes in accordance with the present invention may be used for screening agonist and antagonist compounds for MC receptor activity. Competitive binding assays are well known in the art and are described in the Examples below. Such assays are useful for drug screening of MC receptor agonist and antagonist compounds, as detected in receptor binding assays as described below.

One particular use of such screening assays are for developing drugs and other compounds useful in modifying or changing feeding behavior in mammals. The invention provides an assay system, comprising a panel of recombinant mammalian cells, heterologously expressing each of the MC receptors disclosed herein, wherein the panel is constructed of at least one cell line expressing an MC receptor. The invention provides such panels also comprising a detection means for detecting receptor agonist or antagonist binding, such as the reporter expression constructs described herein, using direct binding and competition binding assays as described in the Examples below. In the use of this panel, each MC receptor is assayed for agonist or antagonist patterns of binding a test compound, and a characteristic pattern of binding for all MC receptors is thereby determined for each test compound. This pattern is then compared with known MC receptor agonists and antagonists to identify new compounds having a pattern of receptor binding activity associated with a particular behavioral or physiological effect.

For example, provided herein is experimental evidence that MC-3 or MC-4 receptor antagonists are capable of stimulating feeding in hungry animals, and that MC-3 or MC-4 agonists are capable of inhibiting feeding in animals otherwise stimulated to eat. The invention provides an in vitro assay to characterize MC-3 and MC-4 agonists/antagonists as a preliminary and economical step towards developing feeding behavior-modulating drugs for use in vivo.

These results on feeding behavior in vivo have been obtained with certain MC receptor binding analogues, SHU9119 and MTII. These compounds have the following chemical structure:

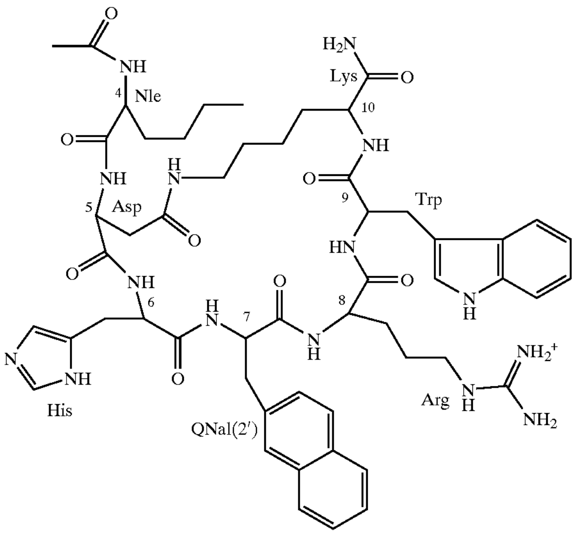

Ac-Nle$^4$-Asp$^5$-His$^6$-QNal(2')$^7$-Arg$^8$-Trp$^9$-Lys$^{10}$-NH$_2$

SHU-9119

-continued

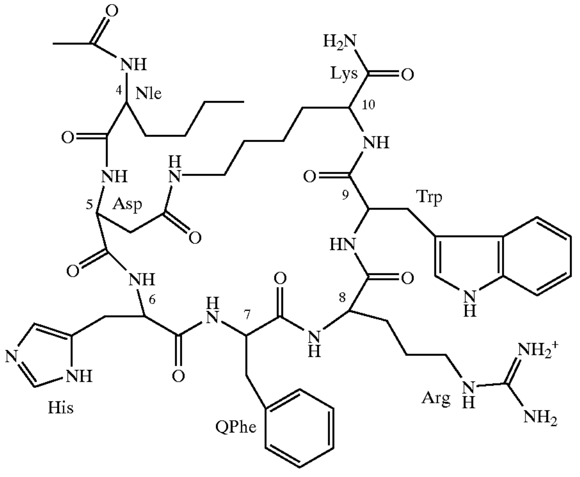

Ac-Nle$^4$-Asp$^5$-His$^6$-QPhe$^7$-Arg$^8$-Trp$^9$-Lys$^{10}$-NH$_2$

MT-II (An additional analogue, SHU8914, has been tested in in vitro receptor binding assays; this compound is identical in structure to SHU9119, except that the amino acid analogue at position 7 is para-iodo-D-phenylalanine.)

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_{16}$ ester, or converted to an amide of formula $NR_1R_2$ wherein $R_1$ and $R_2$ are each independently H or $C_1$–$C_{16}$ alkyl, or combined to form a heterocyclic ring, such as 5- or 6-membered. Amino groups of the peptide, whether aminoterniinal or sidechain, may be in the form of a phannaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted. to an amide. Hydroxyl groups of the peptide side chain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organonimetics mimic the three-dimensional arrangement of the peptide backbone and component amino acid sidechains in the peptide, resulting in such peptido- and organomimetics of the peptides of this invention having substantial biological activity. It is implied that a pharmacophore exists for the receptor agonist and antagonist properties of these and related MC receptor binding analogues. A pharmacophore is an idealized, three-dimensional definition of the structural requirements for biological activity. Peptido- and organomimetics can be designed to fit each pharmacophore with current computer modeling software (computer aided drug design). MC receptor binding analogues derived using such software and comprising peptido- and organomimetics of SHU9119 and MTII and related analogues are within the scope of the claimed invention.

The MC receptor binding analogues, in particular those analogues that are MC-3 or MC-4 receptor agonists or antagonists are provided to be used in methods of influencing, modifying or changing feeding behavior in mammals in vivo. Specific examples of uses for the MC receptor binding analogues of the invention include but are not limited to treatment of eating disorders such as anorexia and obesity, and other pathological weight and eating-related disorders. Other examples are failure to thrive disorders and disease-related cachexia, such as occurs in cancer patients. Also within the scope of the analogues of the invention is use for enhancing appearance, athletic ability, or adjuvant to other therapies to treat disorders such as high blood pressure, high serum cholesterol, vascular and heart disease, stroke, kidney disease, diabetes and other metabolic disorders.

The Examples which follow are illustrative of specific embodiments of the invention, and various uses thereof. They set forth for explanatory purposes only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, cDNA prepared from RNA from human melanoma cells was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, *Science* 244: 569–72; Zhou et al., 1990, *Nature* 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, *Biochemistry* 18: 5294–5299). Double-stranded cDNA was synthesized from total RNA with murine reverse transcriptase (BRL, Gaithersburg, Md.) by oligo-dT priming (Sambrook et al., ibid.). The melanoma cDNA mixture was then subjected to 45 cycles of PCR amplification using 500 picomoles of degenerate oligonucleotide primers having the following sequence:

Primer III (sense):

GAGTCGACCTGTG(CIT)G(C/T)(C/G)AT(C/T)(A/G)
CIIT(G/T)GAC(C/A)G(C/G)TAC (SEQ ID NO:1)

and

Primer VI (antisense):

CAGAATTCAG(T/A)AGGGCAICCAGCAGAI(G/C)(G/A)(T/C)GAA (SEQ ID NO:2)

in 100 μl of a solution containing 50 mM Tris-HCl (pH 8.3), 2.5 MM $MgCl_2$, 0.01% gelatin, 200 μM each DNTP, and 2.5 units of Taq polymerase (Saiki et al., 1988, *Science* 239: 487–491). These primers were commercially synthesized by Research Genetics Inc. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and the insert was then cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, *Proc. Natl. Acad Sci. USA* 74: 5463–5467). Two types of sequences homologous to other G-protein coupled receptors were identified.

EXAMPLE 2A

Isolation of a Mouse αMSH (MC-1) Receptor cDNA

Probes isolated in Example 1 was used to screen a Cloudman melanoma cDNA library in order to isolate a full-length cDNA corresponding to the cloned probe. One clone was isolated from a library of $5\times10^6$ clones screened as described below. This clone contained an insert of 2.6 kilobases (kb). The nucleotide sequence of the complete coding region was determined (see co-owned U.S. Pat. No. 5,532,347, incorporated by reference); a portion of this cDNA comprising the coding region was sequenced and is shown in FIGS. 1A and 1B (SEQ ID Nos:3 & 4).

EXAMPLE 2B

Isolation of a Human αMSH (MC-1) Receptor cDNA

In order to isolate a human counterpart of the murine melanocyte αMSH receptor gene disclosed in Example 2A and co-owned U.S. Pat. No. 5,532,347, a human genomic library was screened at high stringency (50% formamide, 42° C.) using the human PCR fragments isolated as described in Example 1. A genomic clone was determined to encode an human MSH receptor (SEQ ID NO:5.; FIGS. 2A and 2B). The human MSH receptor has a predicted amino acid sequence (SEQ ID NO:6) that is 75% identical and colinear with the mouse αMSH receptor cDNA sequence. The predicted molecular weight of the human $MSH^R$ is 34.7 kD.

EXAMPLE 2C

Isolation of a Human ACTH (MC-2) Receptor cDNA

For cloning the ACTH receptor (MC-2), a human genomic library was screened at high stringency (50% formamide, 1M NaCl, 50 nM Tris-HCl, pH 7.5, 0.1% sodium pyrophosphate, 0.2% sodium dodecyl sulfate, 100 μg/ml salmon sperm DNA, 10×Denhardt's solution, 42° C.), using the human PCR fragments isolated as described in Example 1 herein and U.S. Pat. No. 5,280,112, incorporated by reference. A genomic clone was isolated that encodes a highly related G-coupled receptor protein (SEQ ID No:7 and FIGS. 3A and 3B). The predicted amino acid sequence (SEQ ID NO:8) of this clone is 39% identical and also colinear, excluding the third intracellular loop and carboxy-terminal tail, with the human MSH receptor gene product. The predicted molecular weight of this putative ACTHR is 33.9 kilodaltons (kD). This clone was identified as encoding an MC-2 receptor based on its high degree of homology to the murine and human MSH receptors, and the pattern of expression in different tissue types, as described in Example 3 in U.S. Pat. No. 5,280,112, incorporated by reference herein.

EXAMPLE 2D

Isolation of a Bovine ACTH (MC-2) Receptor cDNA

A bovine genomic DNA clone encoding the bovine counterpart of the MC-2 (ACTH) receptor was isolated from a bovine genomic library, essentially as described in Example 2C above, and its nucleotide sequence determined (as shown in FIGS. 4A and 4B; SEQ ID Nos:9 & 10).

EXAMPLE 2E

Isolation of a Rat γ-MSH (MC-3) Receptor cDNA

The mouse αMSH receptor cDNA isolated as described in Example 2A and co-owned U.S. Pat. No. 5,532,347 was used to screen a rat hypothalamus cDNA library at low stringency (30% formnamide, 5×SSC, 0.1% sodium pyrophosphate, 0.2% sodium dodecyl sulfate, 100 μg/ml salmon sperm DNA, and 10% Denhardt's solution) at 42° C. for 18 h. A 1 kb cDNA clone was isolated and sequenced as described in co-owned U.S. Pat. No. 5,532,347, and this clone used to re-screen the rat hypothalamus cDNA library at high stringency (same conditions as above except that formamide was present at 45%). A cDNA clone approximately 2.0 kb in length was isolated and analyzed as described in co-pending U.S. application Ser. No. 08/044,812, incorporated by reference; a portion of this cDNA comprising the coding region was sequenced and is shown in FIGS. 5A and 5B (SEQ ID Nos:11 & 12).

EXAMPLE 2F

Isolation of a Human MC-4 Receptor DNA

For cloning the MC-4 receptor, a human genomic library was screened at moderate stringency (40% formamide, 1M NaCl, 50 mM Tris-HCl, pH 7.5, 0.1% sodium pyrophosphate, 0.2% sodium dodecyl sulfate, 100 μg/ml salmon sperm DNA, 10×Denhardt's solution, 42° C.), using rat PCR fragments isolated as described in Example 1 herein, with the exception that the following primers were used for PCR:

Primer II (sense):

GAGTCGACC(A/G)CCCATGTA(C/T)T(AGT)(C/T)TTCATCTG (SEQ ID NO:13)

and

Primer VII (antisense):

CAGAATTCGGAA(A/G)GC(A/G)TA(G/T)ATGA(A/G)GGGGTC (SEQ ID NO:14)

A genomic clone was isolated that encodes a highly related G-coupled receptor protein (SEQ ID NO:15 and FIGS. 6A and 6B) on a 1.9 kb HindIII fragment. The predicted amino acid sequence (SEQ ID NO:16) of this clone shares 55–61% sequence identity with human MC-3 and MC-5 receptors, and 46–47% sequence identity with the human MC-1 and MC-2 (ACTH) receptor.

EXAMPLE 2G

Isolation of a Mouse MC-5 Receptor DNA

One million clones from a mouse 129SVJ genomic library comprising 5,000,000 clones in the λFixII vector (Stratagene) were screened at low stringency (hybridization in 40% formamide at 42° C., washing performed in 0.5×SSC at 60° C., as described above in Example 2E) using radiolabeled probes from the rat MC-3 and MC-4 receptors, as described in Examples 2E and 2F). Positively-hybridizing clones were isolated and sequenced, and the sequences obtained were compared to previously-isolated melanocortin receptor clones. One clone, comprising a previously-unknown sequence, was determined to encode the MC-5 melanocortin receptor. The nucleotide and amino acid sequences of this receptor are shown in FIGS. 7A and 7B (SEQ ID No.:17 & 18).

EXAMPLE 3

Construction of a Recombinant Expression Construct, DNA Transfection and Functional Expression of the MCR Gene Products In order to produce recombinant mammalian cells expressing each of the melanocortin receptors of Example 2, cDNA or the coding exons from genomic. DNA from each receptor was cloned into a mammalian expression construct, the resulting recombinant expression construct transfected into human 293 cells, and cell lines generated that expressed the melanocortin receptor proteins in cellular membranes at the cell surface.

The mouse αMSH receptor was cloned by excising the entire coding region of the $\alpha MSH^R$ (MC-1) cDNA insert comprising a 2.1 kb fragment and subcloning this fragment into the BamHI/XhoI sites of pcDNAI/neo expression vector (Invitrogen, San Diego, Calif.). The resulting plasmid was prepared in large-scale through one cycle of CsCl gradient ultracentrifugation, and 20 μg of the plasmid transfected into each 100 mm dish of 293 cells using the calcium phosphate method (see Chen & Okayama, 1987*, Mol. Cell. Biol.* 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 μg/mL; selection was started 72 hr after transfection and continued for 3 weeks.

The $\alpha MSH^R$ is known to couple to G-proteins and thereby activate adenyl cyclase, increasing intracellular levels of cAMP (see Buckley & Ramachandran, 1981*, Proc. Natl. Acad. Sci. USA* 78: 7431–7435; Grahame-Smith et al., 1967*, J. Biol. Chem* 242: 5535–5541; Mertz & Catt, 1991*, Proc. Natl. Acad. Sci. USA* 88: 8525–8529; Pawalek et al., 1976, Invest. Dermatol. 66: 200–209). This property of cells expressing the αMSH receptor was used analyze expression of the αMSH receptor in cell colonies transfected with the expression vectors described herein as follows. Cells (~$1\times10^6$) were plated in 6-well dishes, washed once with DMEM containing 1% bovine serum albumin (BSA) and 0.5 mM IBMX (a phosphodiesterase inhibitor), then incubated for 45 minutes at 37° C. with varying concentrations of the melanotropic peptides αMSH, βMSH, γMSH, the MSH peptide analogues $Nle^4$, $D\text{-}Phe^7$-αMSH (NDP-MSH), and ACTH. Following hormone treatment, the cells were washed twice with phosphate buffered saline and intracellular cAMP extracted by lysing the cells with 1 mL of 60% ethanol. Intracellular cAMP concentrations were determined using an assay (Amersham) which measures the ability of cAMP to displace [8-$^3$H] cAMP from a high affinity cAMP binding protein (see Gilman, 1970*, Proc. Natl. Acad. Sci. USA* 67: 305–312).

The results of these experiments are shown in FIG. 8. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing the murine αMSH receptor responded to melanotropic peptides with a 2–3 fold elevation of intracellular cAMP, similar to levels of cAMP induced by these peptides in the Cloudman cell line (see Pawalek, 1985*, Yale J. Biol. Med.* 58: 571–578). The $EC_{50}$ values determined for αMSH ($2.0\times10^{-9}$M), ACTH ($8.0\times10^{-9}$M) and the superpotent MSH analogue NDP-MSH ($2.8\times10^{-11}$M) correspond closely to reported values (see Tatro et al., 1990*, Cancer Res.* 50: 1237–1242). As expected, the βMSH peptide had an $EC_{50}$ value comparable to αMSH, while γMSH had little or no activity (see Slominski et al., 1992*, Life Sci.* 50: 1103–1108), confirming the identity of this receptor as a melanocyte αMSH receptor.

Figure 9:
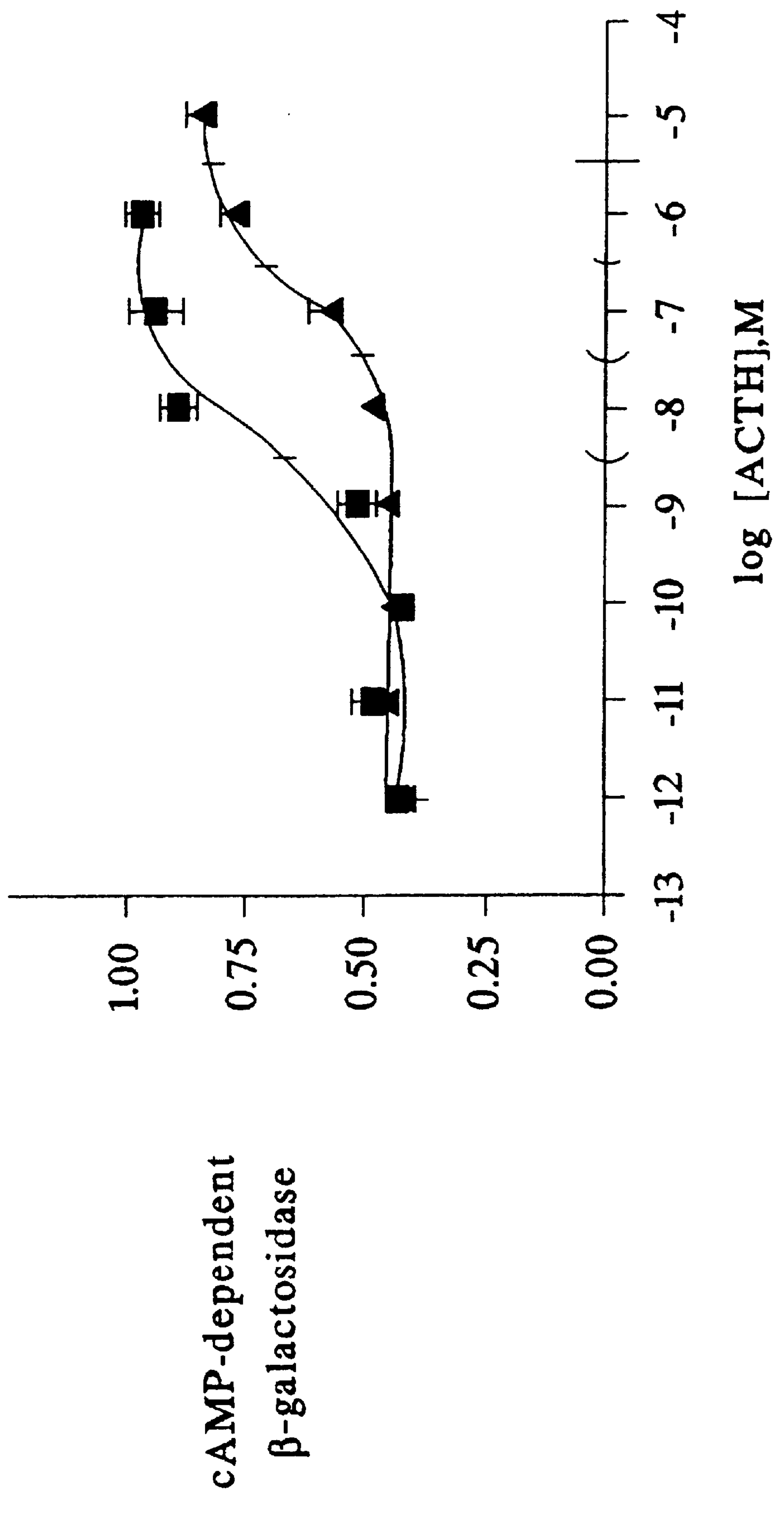
FIG. 9 illustrates the cAMP response of mouse Y1 cells to binding of melanocortin peptides to human melanocortin-2 (ACTH) receptor, as measured using the β-galactosidase assay described in Example 4.

A similar series of experiments were performed using mouse Y1 cells (subclone OS3; Schimmer et al., 1995*, J. Cell. Physiol.* 163: 164–171) expressing the human and bovine MC-2 (ACTH) receptor clones of Examples 2C and 2D. These results are shown in FIG. 9, where the extent of cAMP responsive element-linked β-galactosidase activity (see Example 4, below) is shown with increasing concentrations of ACTH.

The entire coding region of the MC-3 receptor cDNA insert, obtained as described above in the co-pending U.S. Ser. No. 08/044,812, was contained in a 2.0 kb restriction enzyme digestion fragment and was cloned into the BamHI/IXhoI sites of pcDNA/neo I expression vector (Invitrogen, San Diego, Calif.). The resulting plasmid was prepared in large-scale through one cycle of CsCl gradient ultracentrifugation and 20 μg pcDNA/MC-3 receptor DNA were transfected into each 100 mm dish of 293 cells using the calcium phosphate method (see Chen & Okayama, 1987*, Mol. Cell. Biol.* 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 μg/mL; selection was started 72 h after transfection and continued for 3 weeks.

Specific binding of melanocortin peptides to cells expressing the MC-3 receptor was demonstrated by competition experiments using $^{125}$I-labeled $Nle^4$-$D\text{-}Phe^7$-α-MSH (NDP-MSH, as described in Tatro et al., 1990*, Cancer Res.* 50: 1237–1242). Suspended cells ($2\times10^5$) were incubated at 37° C. with 500,000 cpm of labeled peptide for 10 min in binding buffer (Ham's F10 media plus 10 mM HEPES, pH 7.2, 0.25% bovine serum albumin, 500K IU/mL aprotinin, 100 μg/mL bacitracin and 1 mM 1,10-phenanthroline) in the presence or absence of the indicated concentrations of peptides. Maximum labeling was achieved within 10 min.

Figure 10:
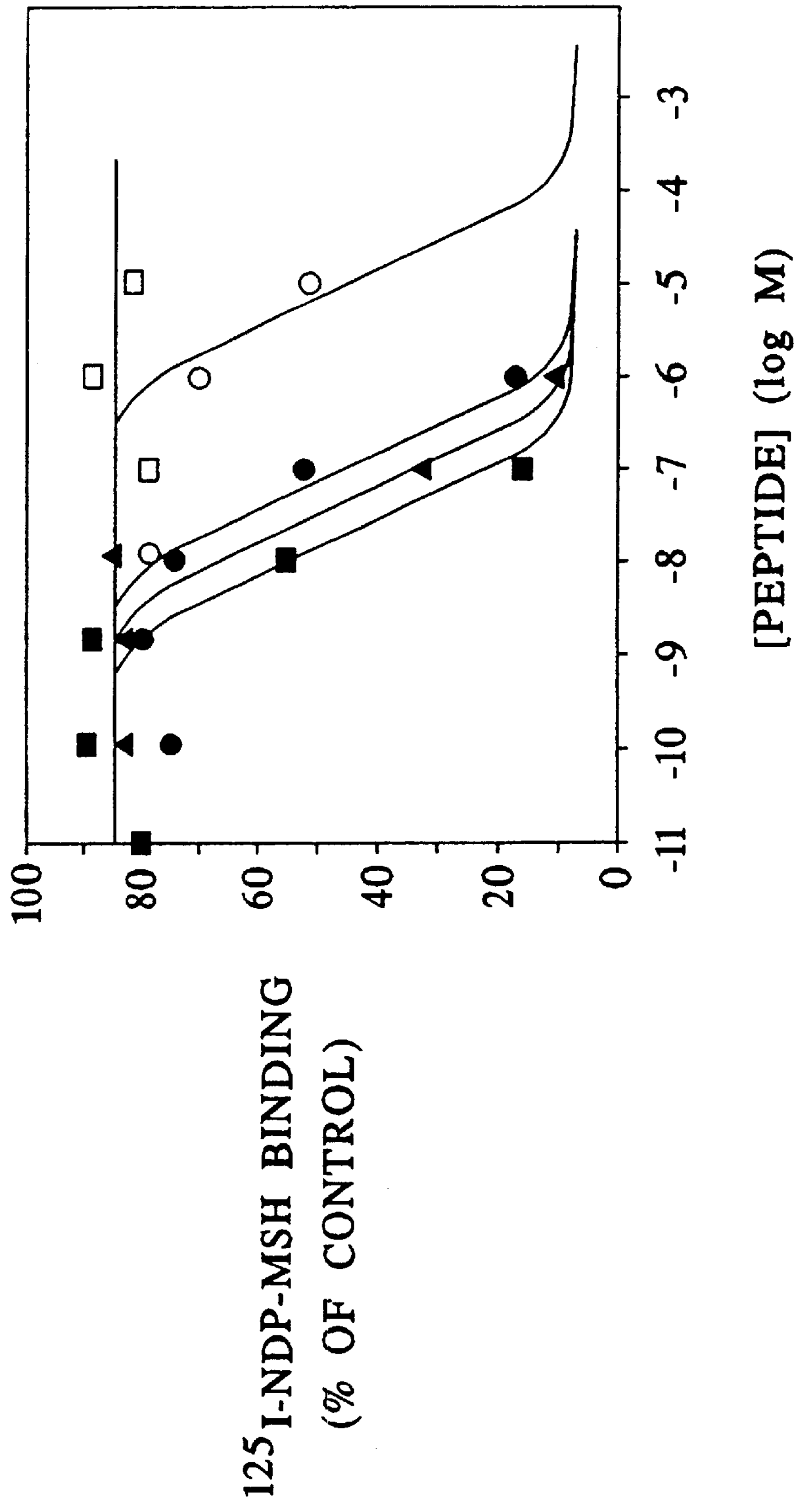
FIG. 10 illustrates the results of competition binding experiments of melanocortin pepfides to cells expressing a recombinant expression construct encoding the rat melanocortin-3 receptor.

The results of these experiments are shown in FIG. 10. Labeled NDP-MSH binding to cells expressing the MC-3 receptor, produced as described above, is inhibited by competition with unlabeled peptides known to be melanocortin receptor agonists, having a relative order of potency as follows:

NDP-MSH>γ-MSH>α-MSH>$ACTH_{4-10}$>>>ORG2766.

Approximate $K_1$ values derived from this experiment are as shown in Table I:

TABLE I

| Agonist | $K_i$ (approx) |
|---|---|
| NDP-MSH | $2 \times 10^{-8}$ |
| γ-MSH | $5 \times 10^{-8}$ |
| α-MSH | $1 \times 10^{-7}$ |
| $ACTH_{4-10}$ | $8 \times 10^{-5}$ |

cAMP production assays as described above were also used to analyze expression of MC3-R in cells transfected with the expression vectors described herein as follows. Cells (~$5\times10^6$) were plated in 6-well dishes, washed once with DMEM containing 1% bovine serum albumin (BSA) and 0.5 mM IBMX (a phosphodiesterase inhibitor), then incubated for 1 h at 37° C. with varying concentrations of the melanotropic peptides αMSH, $\gamma_3$MSH, γMSH, the MSH peptide analogues $Nle^4$-D-$Phe^7$-αMSH (NDP-MSH), $ACTH_{4-10}$ and $ACTH_{1-39}$. Following hormone treatment, the cells were washed twice with phosphate buffered saline and intracellular cAMP extracted by lysing the cells with 1 mL of 60% ethanol. Intracellular cAMP concentrations were determined using an assay which measures the ability of cAMP to displace [8-$^3$H] cAMP from a high affinity cAMP binding protein (see Gilman, 1979*, Proc. Natl. Acad. Sci. USA* 67: 305–312).

Figure 11:
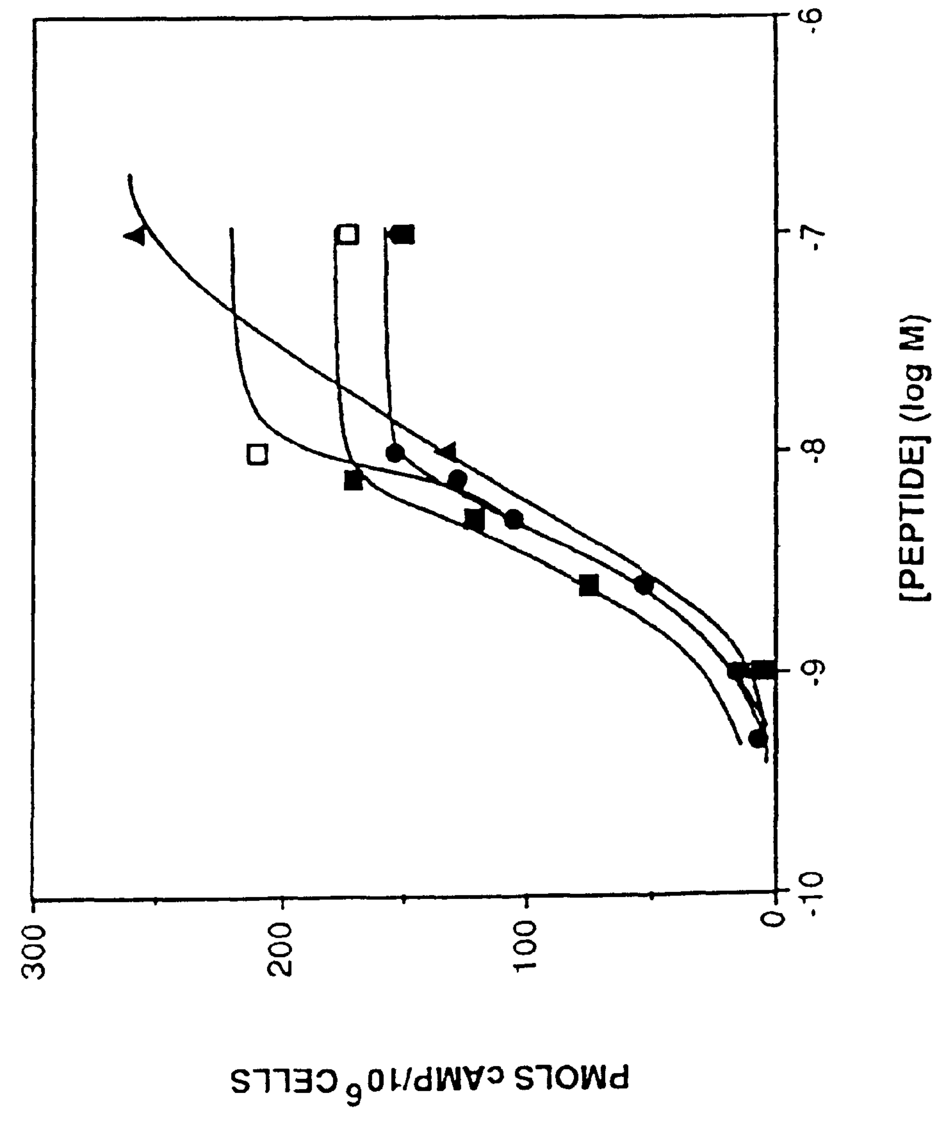
FIGS. 11A through 11C illustrate the results of experiment showing intracellular cAMP accumulation caused by receptor-ligand binding in human 293 cells expressing the MC-3 receptor.
Figure 11:
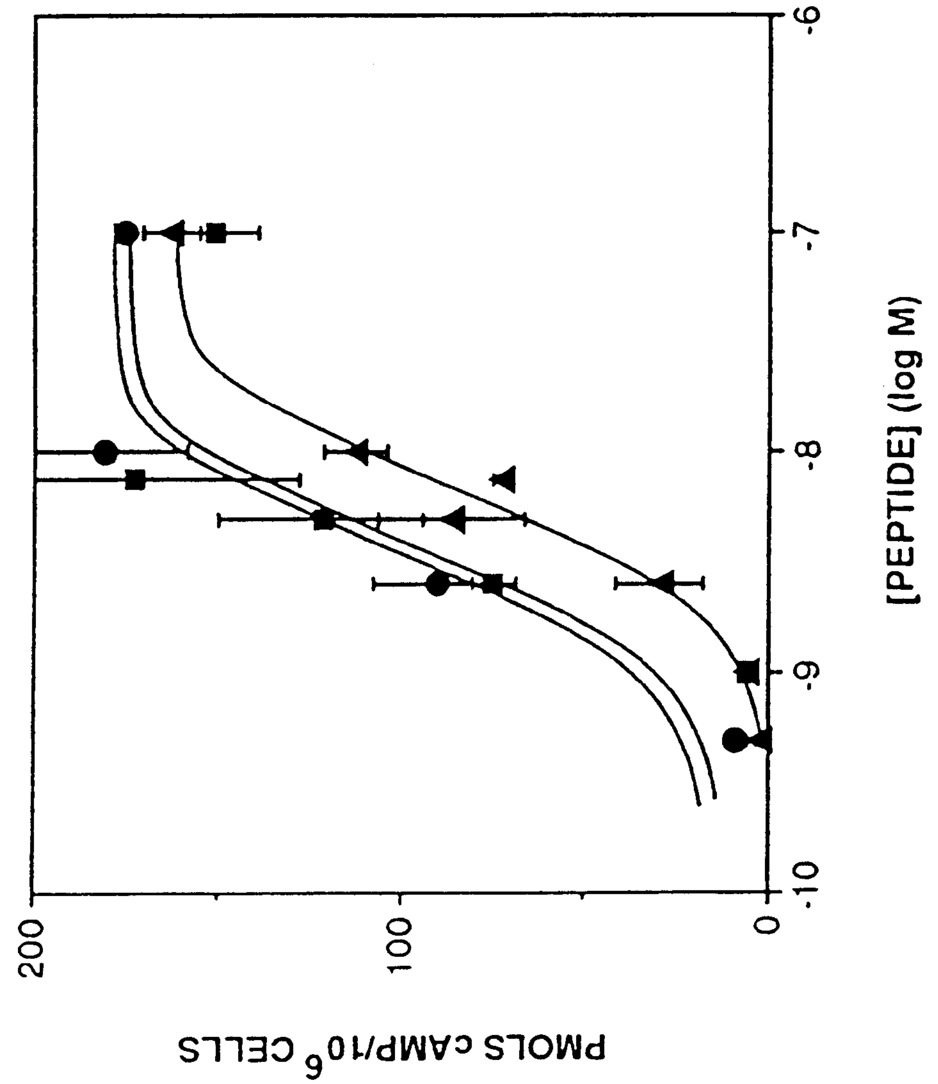
Figure 11:
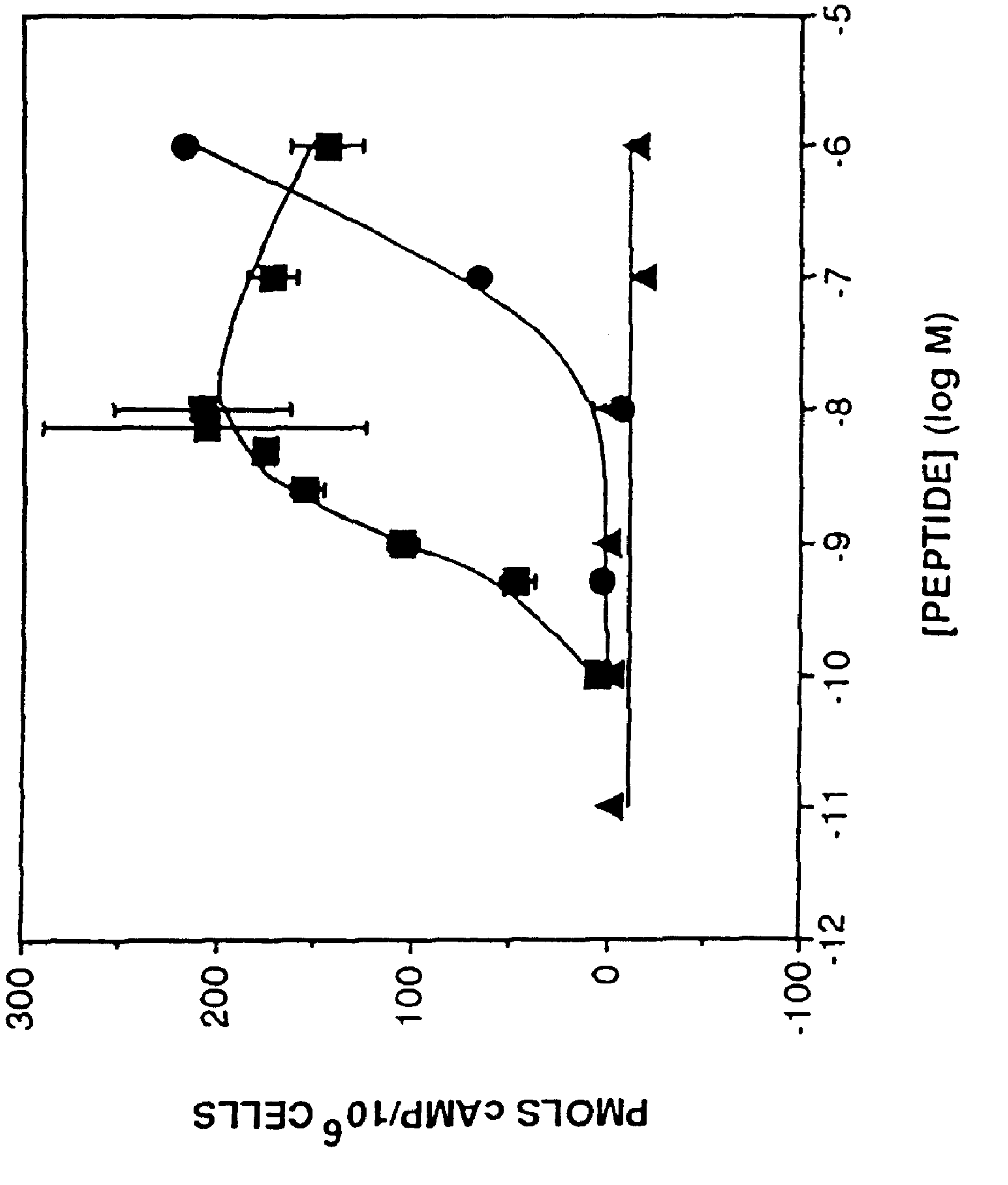

The results of these experiments are shown in FIGS. 11A through 11C. The abscissa indicates the concentration of each hormone and the ordinate indicates the percentage of basal intracellular cAMP concentration achieved by each treatment. Points indicate the mean of duplicate incubations; the standard error did not exceed 15% for any data point. Panel A depicts the results of experiments using peptides found in vivo; Panel B depicts results found with γ-MSH variants; and Panel C shows results of synthetic melanocortin analogues. None of the peptides tested induced any change in intracellular cAMP in cells containing the vector alone. Cells expressing rat MC3-R responded strongly to every melanotropic peptide containing the MSH code sequence His-Phe-Arg-Trp, with up to a 60-fold elevation of intracellular cAMP levels. $EC_{50}$ values ranged from 1–50 nM. The most potent ligand and the one having the lowest $EC_{50}$ was found to be γMSH. The order of potency for the naturally occurring melanocortins was found to be:

$\gamma_2$-MSH=γMSH>αMSH=$ACTH_{1-39}$>$\gamma_3$-MSH>des-acetyl-αMSH>$ACTH_{4-10}$.

$Ec_{50}$ values for these compounds are shown in Table II:

TABLE II

| Agonist | $Ec_{50}$ |
|---|---|
| NDP-MSH | $1 \times 10^{-9}$ |
| $\gamma_1$-MSH | $3 \times 10^{-9}$ |
| $\gamma_2$-MSH | $3 \times 10^{-9}$ |
| α-MSH | $4 \times 10^{-9}$ |
| $ACTH_{1-39}$ | $4 \times 10^{-9}$ |
| $\gamma_3$-MSH | $6 \times 10^{-9}$ |
| desacetyl-αMSH | $8 \times 10^{-9}$ |
| $ACTH_{4-10}$ | $1 \times 10^{-7}$ |

Additionally, a synthetic melanocortin peptide (ORG2766), known to have the greatest activity in vivo in stimulation of retention of learned behavior and in stimulation of neural regeneration, was unable to stimulate MC3-R-mediated cAMP production, and was also inactive as an antagonist. The results strongly indicate that this peptide does not bind to MC3-R protein.

Figure 12:
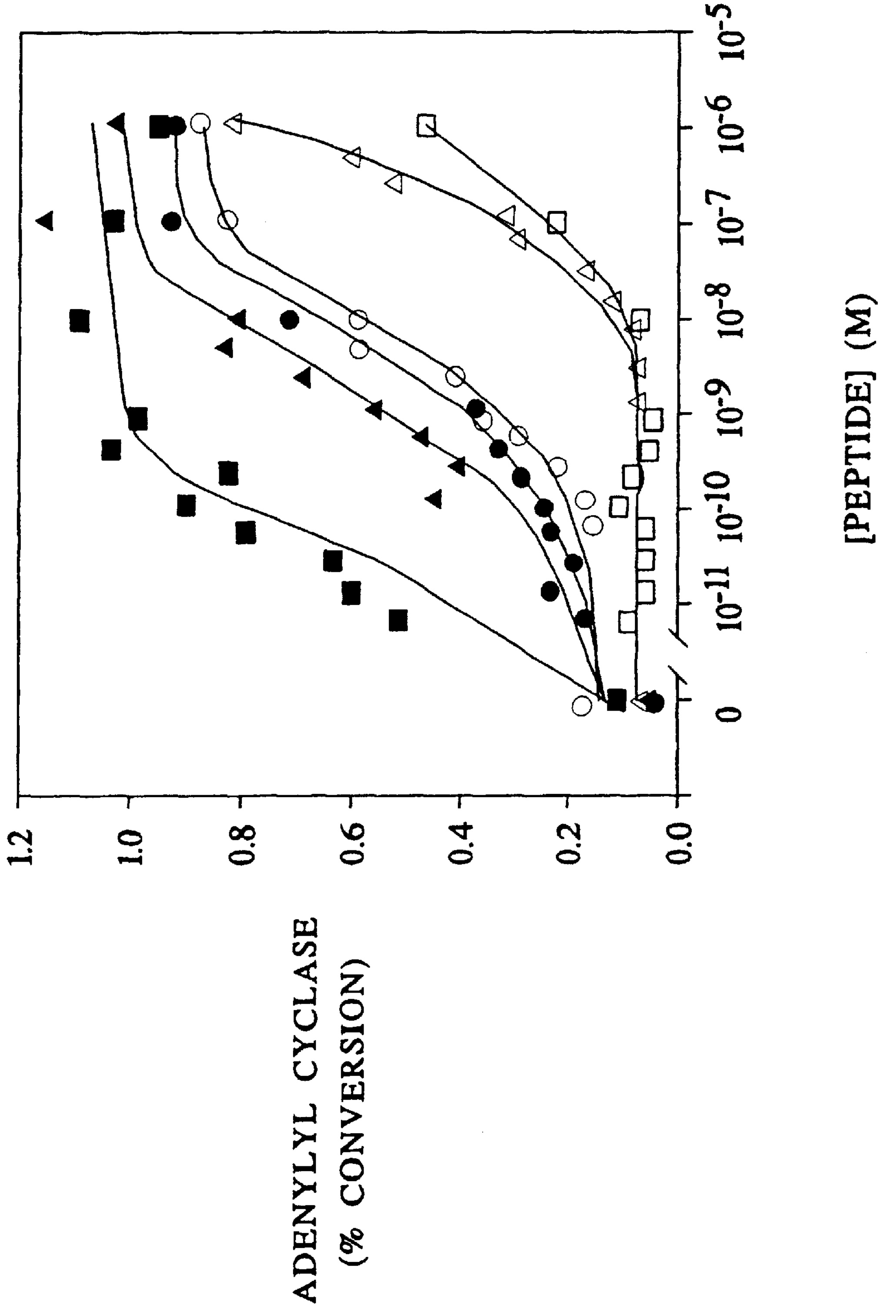
FIG. 12 shows a graph of intracellular cAMP accumulation resulting from peptides to human melanocortin-4 receptor agonist binding in human 293 cells transfected with a MC-4 receptor-encoding recombinant expression construct.

The MC-4 receptor was cloned in a 1.9 kb HindIII genomic DNA fragment after PCR amplification of a lambda phage clone into pcDNAI/Neo (Invitrogen). This plasmid was stably introduced into human 293 cells by calcium phosphate co-precipitation using standard techniques, and plasmid-containing cells selected in G418 containing media. Specificity of receptor-hormone binding was assayed using adenylate cylcase activity as described above. The MC-4 receptor was found to couple to adenylate cyclase activity having the following pattern of agonist affinity:

NDP-MSH>des-acetyl-α-MSH>/=$ACTH_{1-39}$>/=α-MSH>>$\gamma_2$-MSH=$ACTH_{4-10}$ whereas the synthetic $ACTH_{4-9}$ analogue ORG2766 showed no detectable binding to the MC-4 receptor. The results of adenylate cyclase activity assays are shown in FIG. 12. $EC_{50}$ values for each of the tested MC-4 receptor agonists are as shown in Table III:

TABLE III

| Agonist | $Ec_{50}$ |
|---|---|
| NDP-MSH | $1.1 \times 10^{-11}$M |
| desacetyl-αMSH | $4.9 \times 10^{-10}$M |
| $ACTH_{1-39}$ | $6.8 \times 10^{-10}$M |
| α-MSH | $1.5 \times 10^{-9}$M |
| $\gamma_2$-MSH | $>10^{-7}$M |
| $ACTH_{4-10}$ | $>10^{-7}$M |

Figure 13:
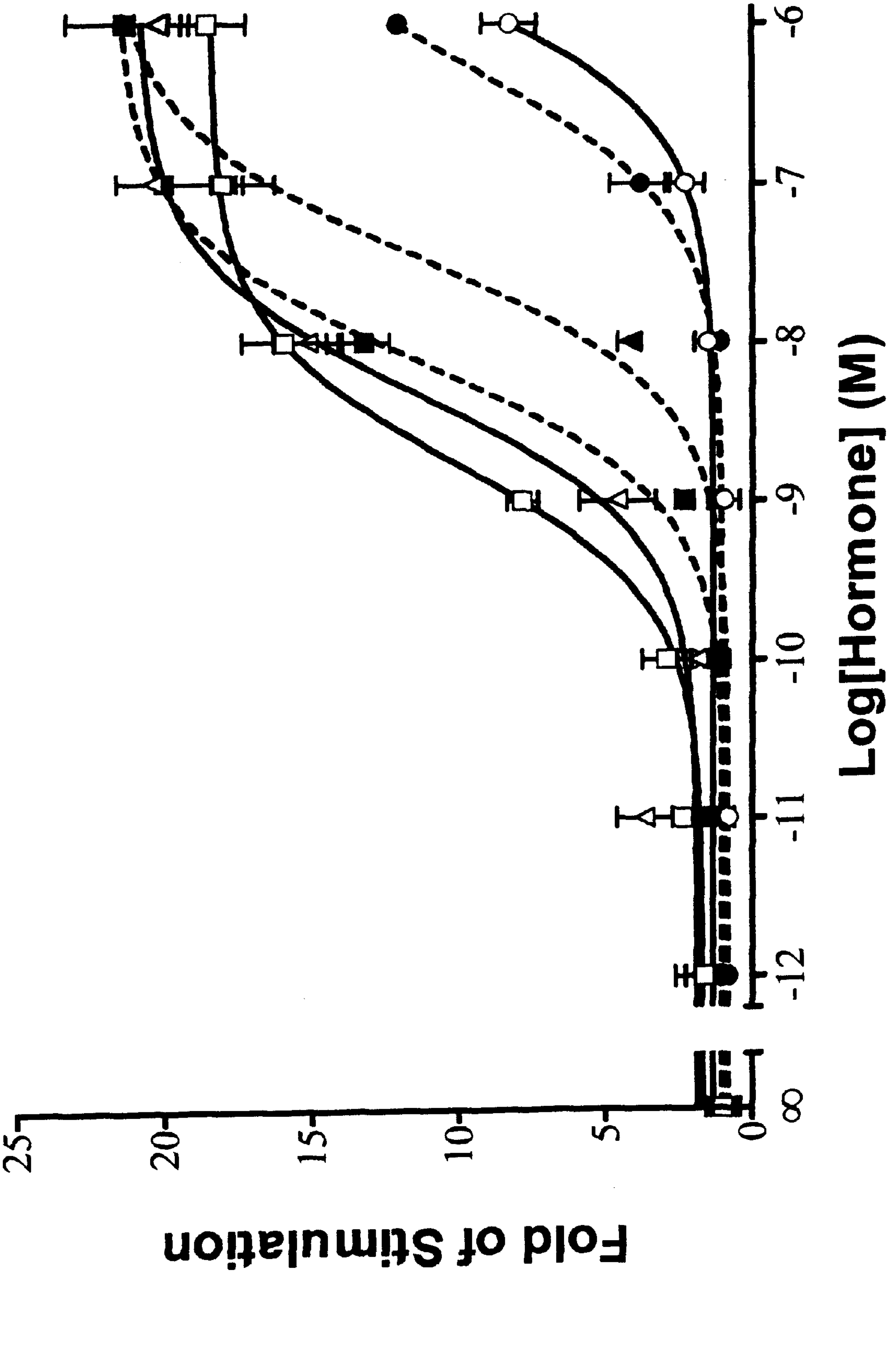
FIG. 13 illustrates the results of cAMP accumulation (AC) and cAMP-dependent β-galactosidase (β-gal) assays of melanocortin peptide binding to a rat melanocortin-5 receptor.

A 1.6 kb ApaI-HindIII fragment comprising the entire coding sequence of the mouse MC-5 melanocortin receptor disclosed in Example 2G above was cloned into the pcDNA/neo expression vector (Invitrogen) after PCR amplification of the lambda phage clone. This plasmid was stably introduced into human 293 cells by calcium phosphate co-precipitation using standard techniques, and plasmid-containing cells selected in G418 containing media. Specificity of receptor-hormone binding was assayed using adenylate cylcase activity as described above. The MC-5 receptor was found to couple to adenylate cyclase activity having the following pattern of agonist affinity:

α-MSH>PMSH>>γ-MSH The results of adenylate cyclase activity assays (AC) and cAMP-dependent β-galactosidase (β-gal) assay are shown in FIG. 13. $EC_{50}$ values for each of the tested MC-5 receptor agonists are: α-MSH=$1.7\times10^{-9}$M; and βMSH=$5\times10^{-9}$M.

EXAMPLE 4

Melanocortin Analogue Binding to Mammalian Melanocortin Receptors

Recombinant cells prepared as described above in Example 3 were used to characterize receptor binding of two melanocortin analogues comprising cyclic lactarn heptapeptides.

The melanocortin receptor analogue SHU9119 has the following chemical structure:

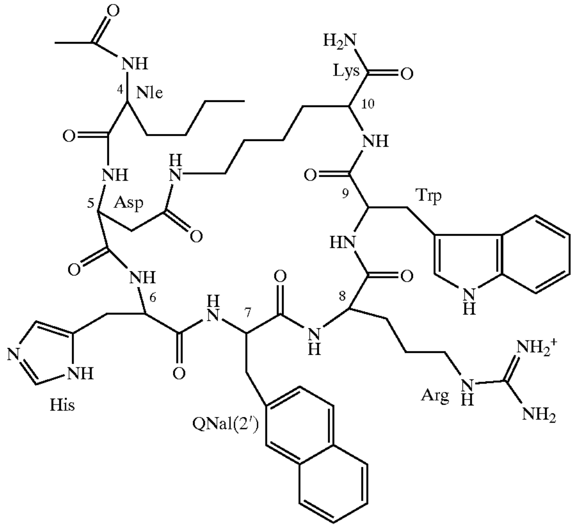

Ac-Nle$^4$-cyclo(Asp$^5$, D-Nal(2)$^7$, Lys$^{10}$) αMSH-(4-10)-amide The melanocortin receptor analogue MTII has the following chemical structure:

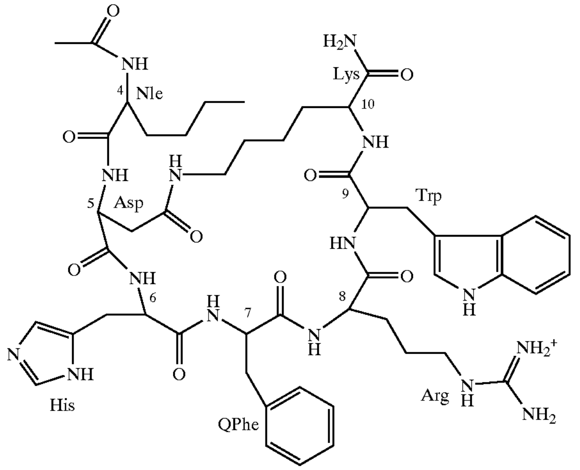

These analogues were prepared as described in Hruby et al. (1995, *J. Med. Chem.* 38: 3454–3461).

Figure 14:
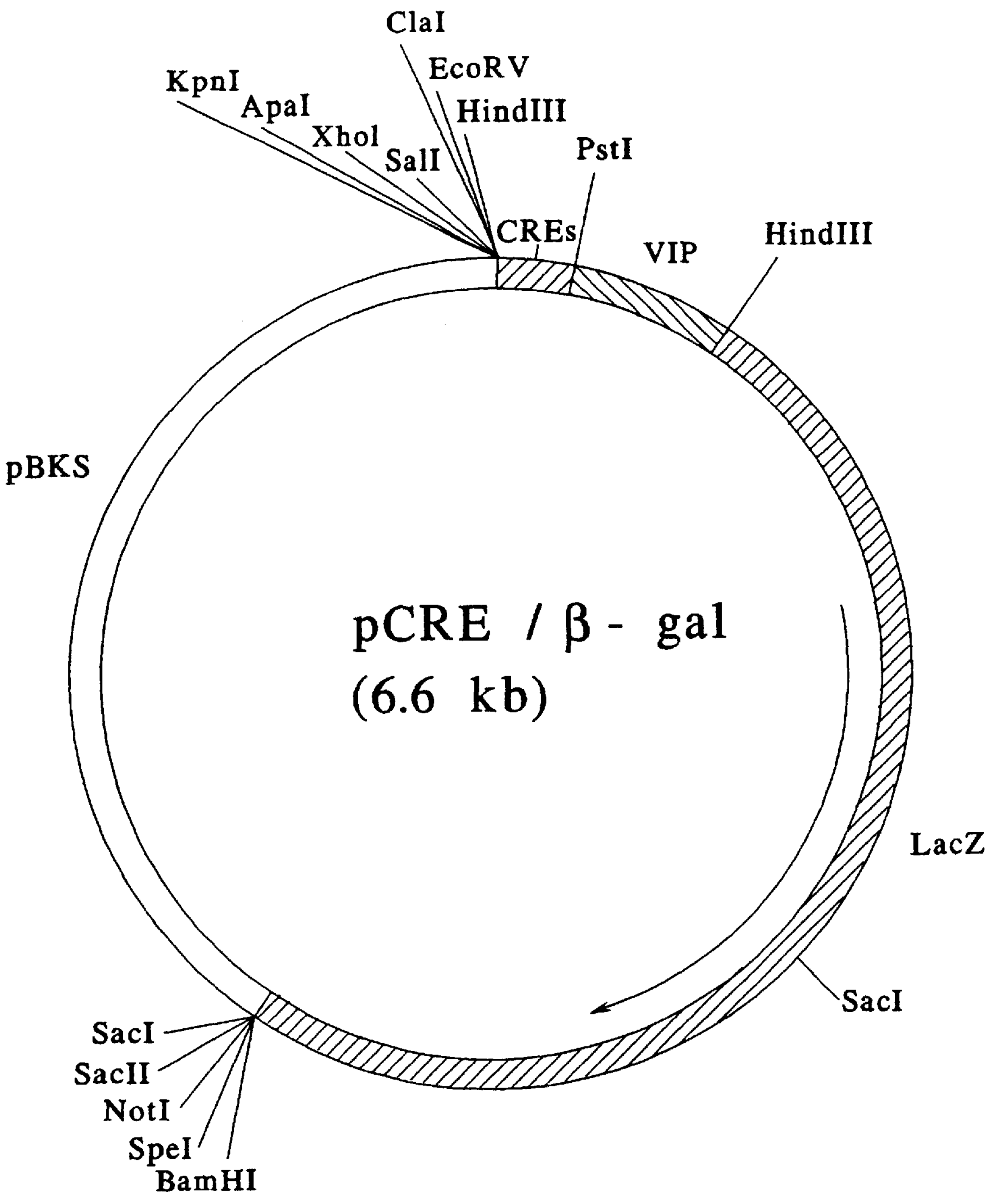
FIG. 14 illustrates the structure of the pCRE/β-gal plasmid.
Figure 15A:
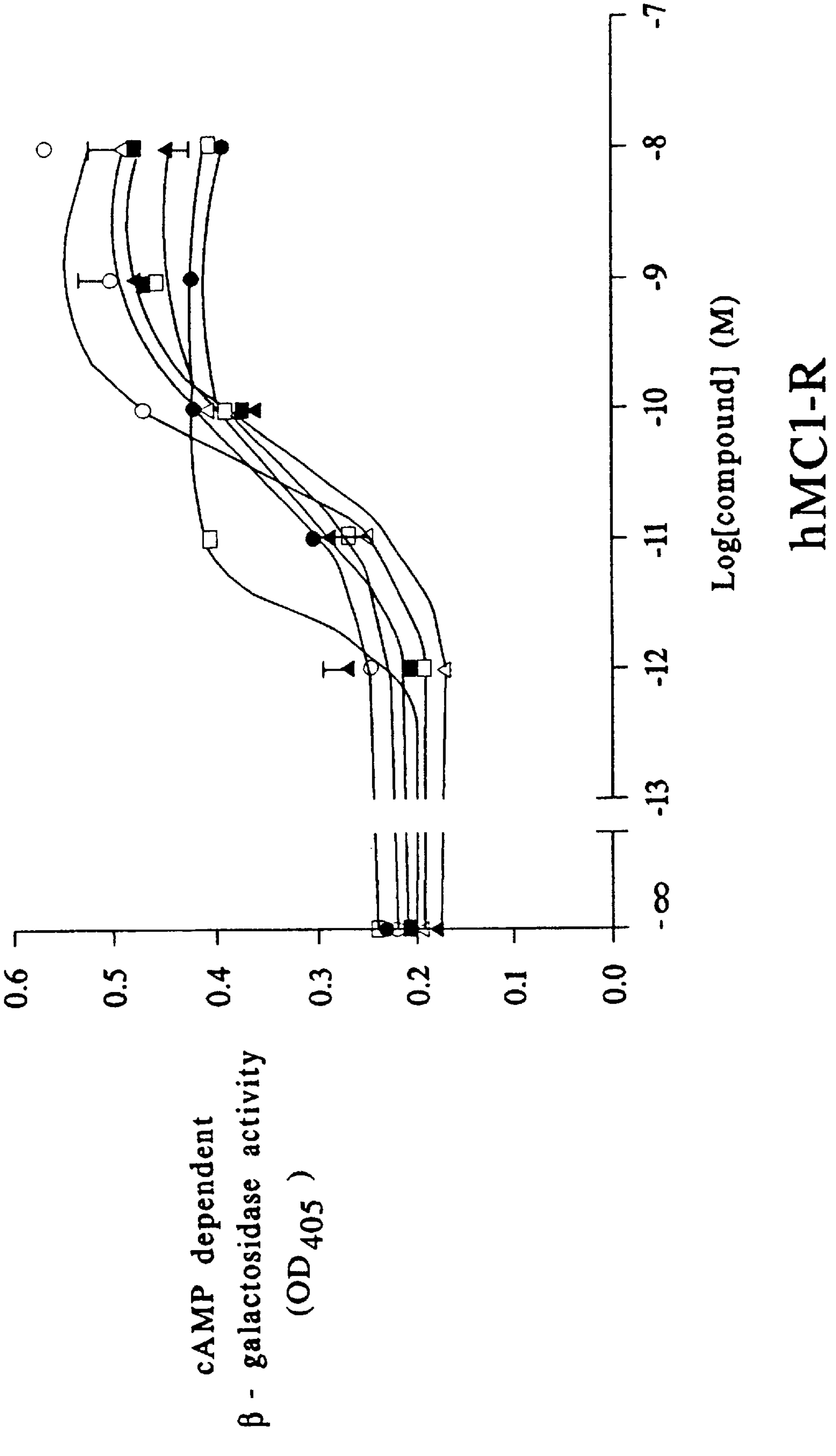
FIG. 15 illustrates the results of the β-galactosidase-coupled, colorimetric melanocortin receptor binding assay using cells expressing each of the MC-1, MC-3, MC-4 or MC-5 receptors and contacted with αMSH or a variety of αMSH analogues.
Figure 15B:
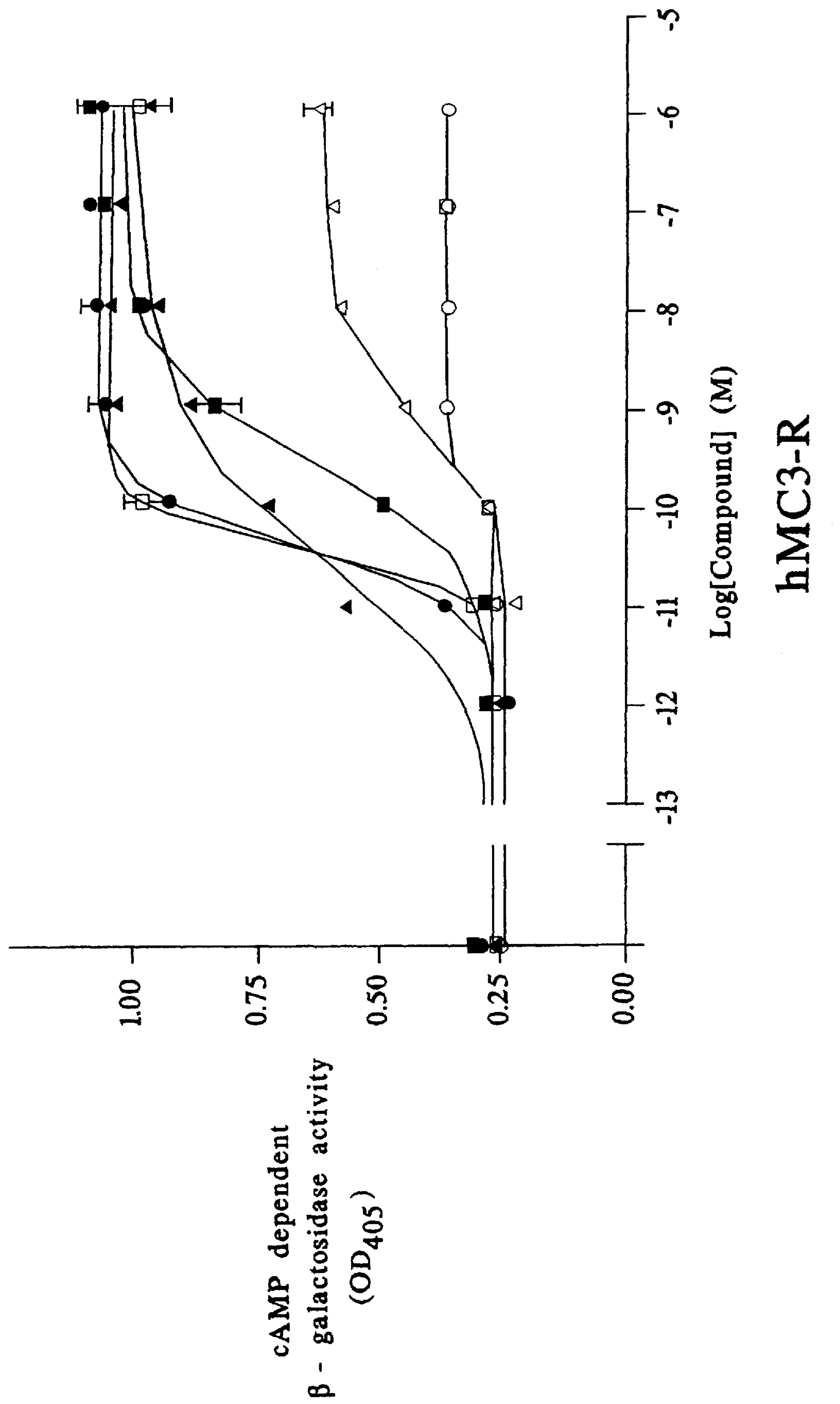
Figure 15C:
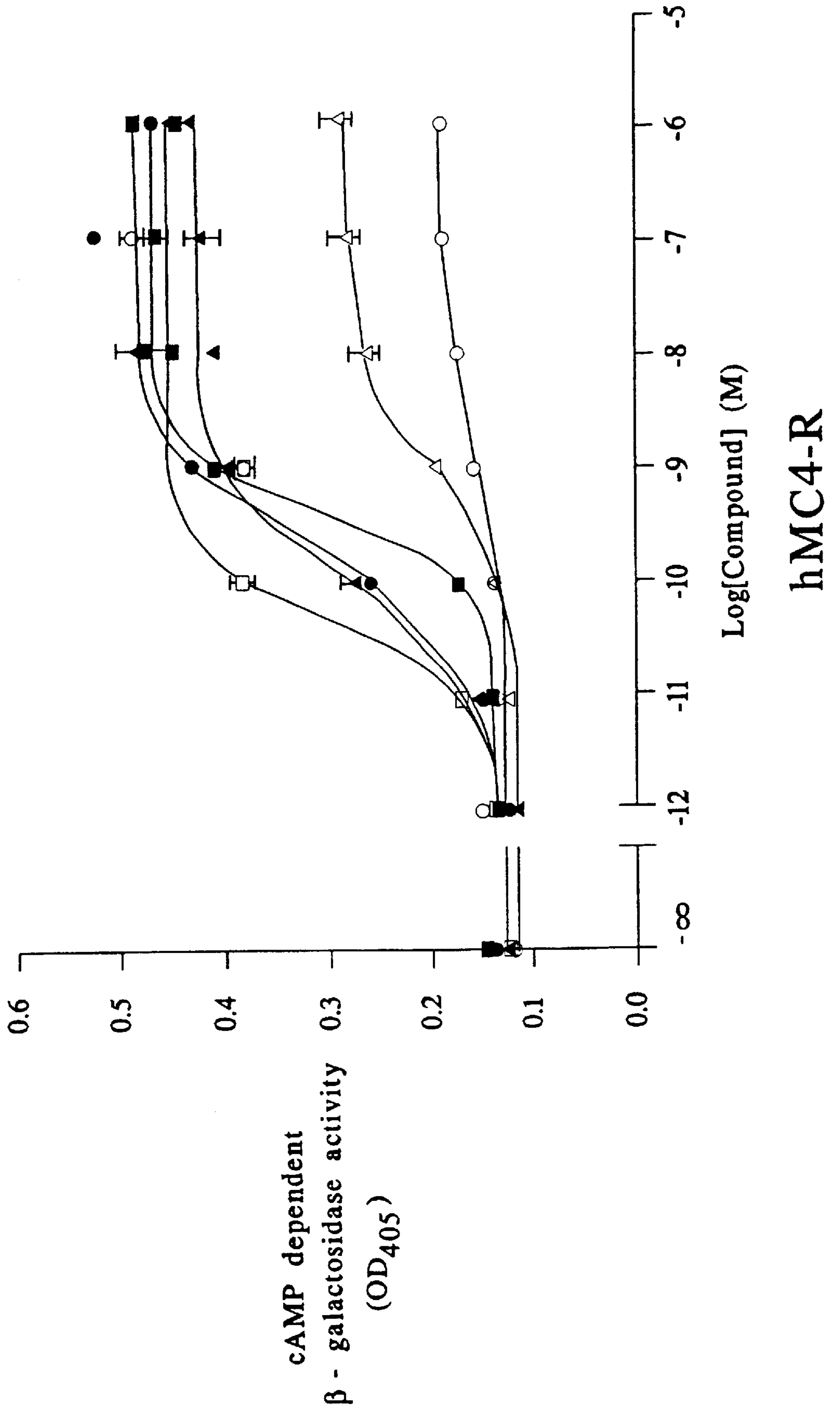
Figure 15D:
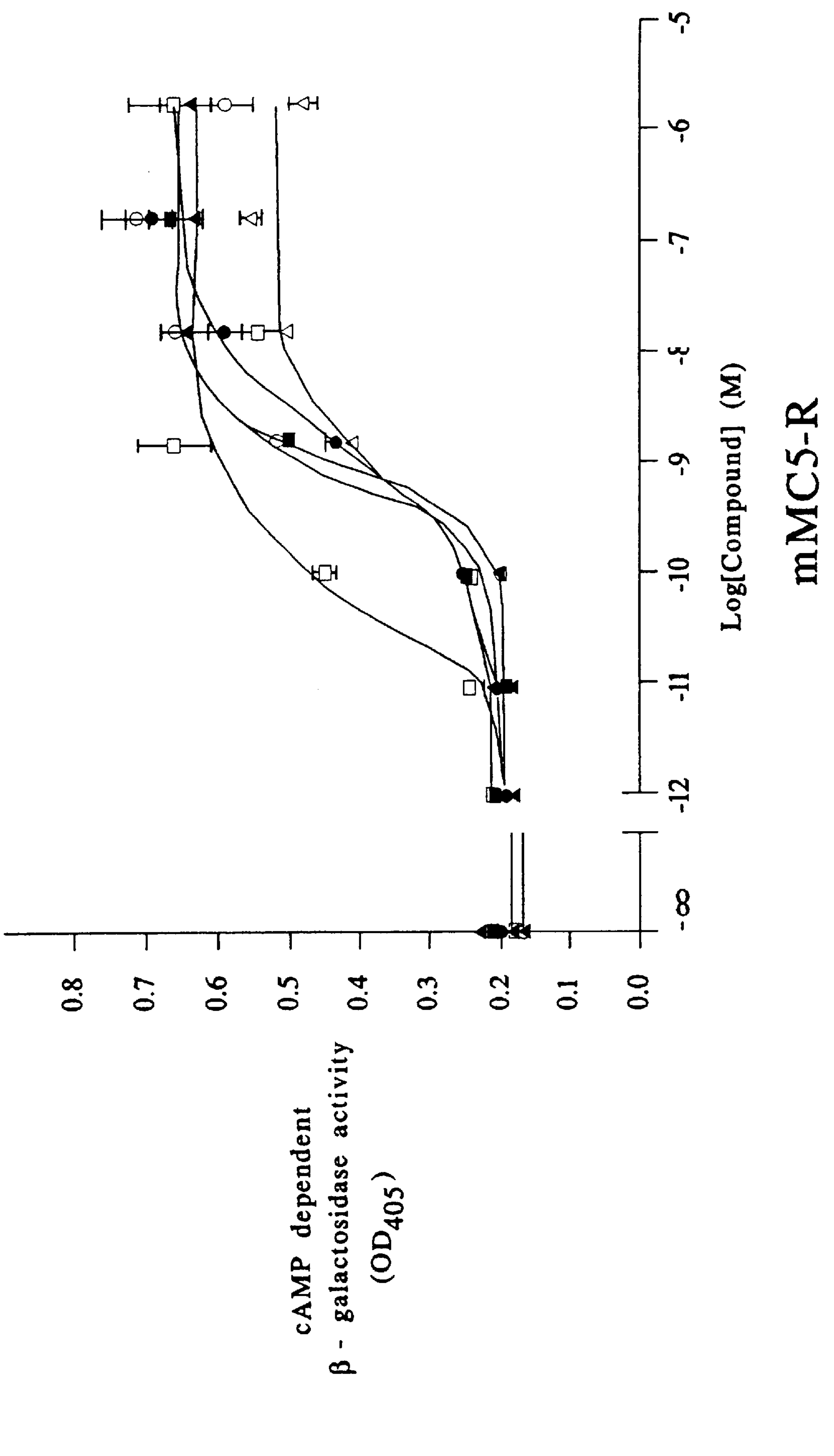
Figure 16A:
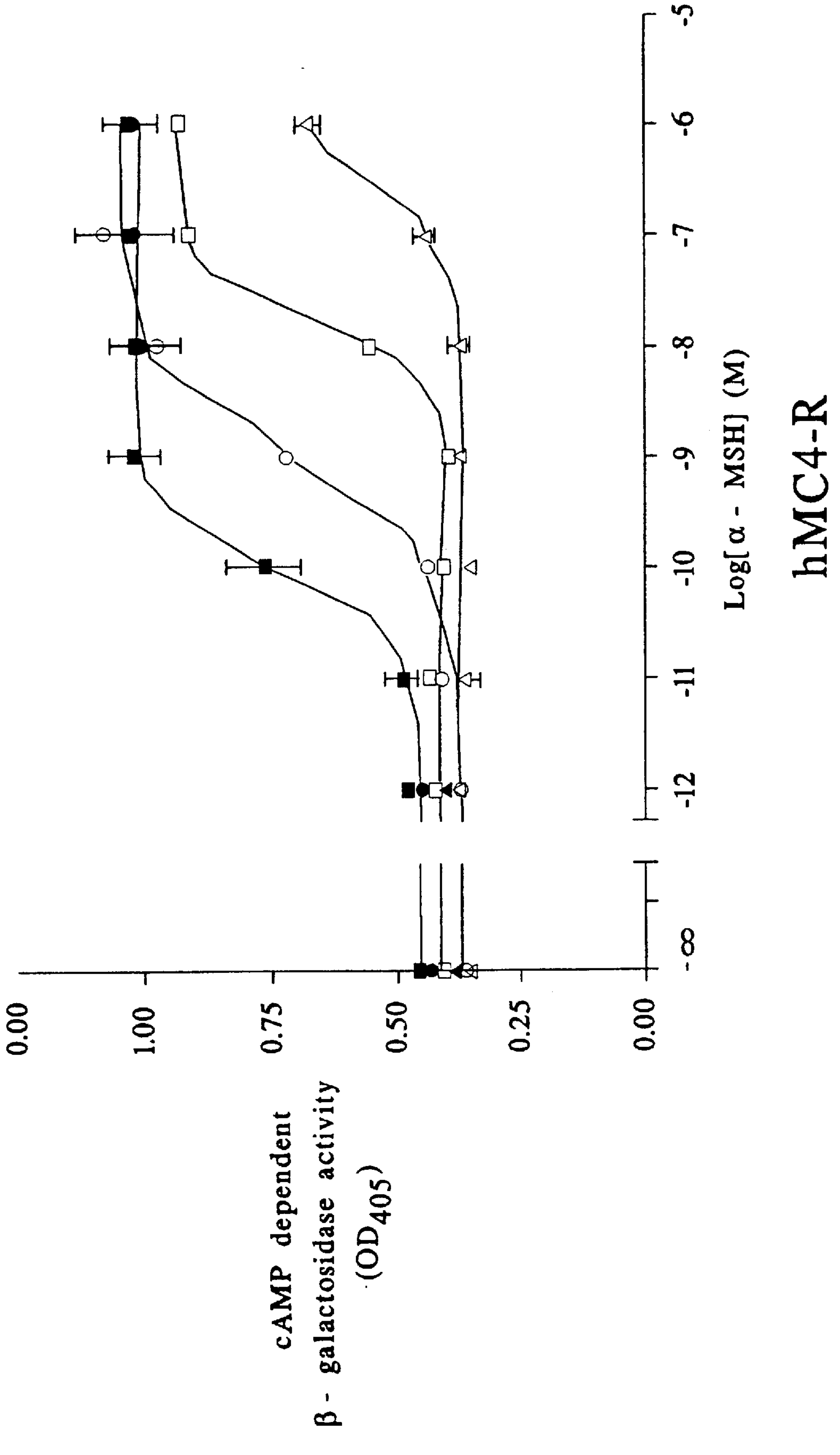
FIG. 16 shows the results of the β-galactosidase-coupled, colorimetric melanocortin receptor binding assay to determine antagonist activity of melanocortin analogues SHU9119 and SHU8914 in cells expressing each of the melanocortin receptors MC-1, MC-3, MC-4 and MC-5.
Figure 16B:
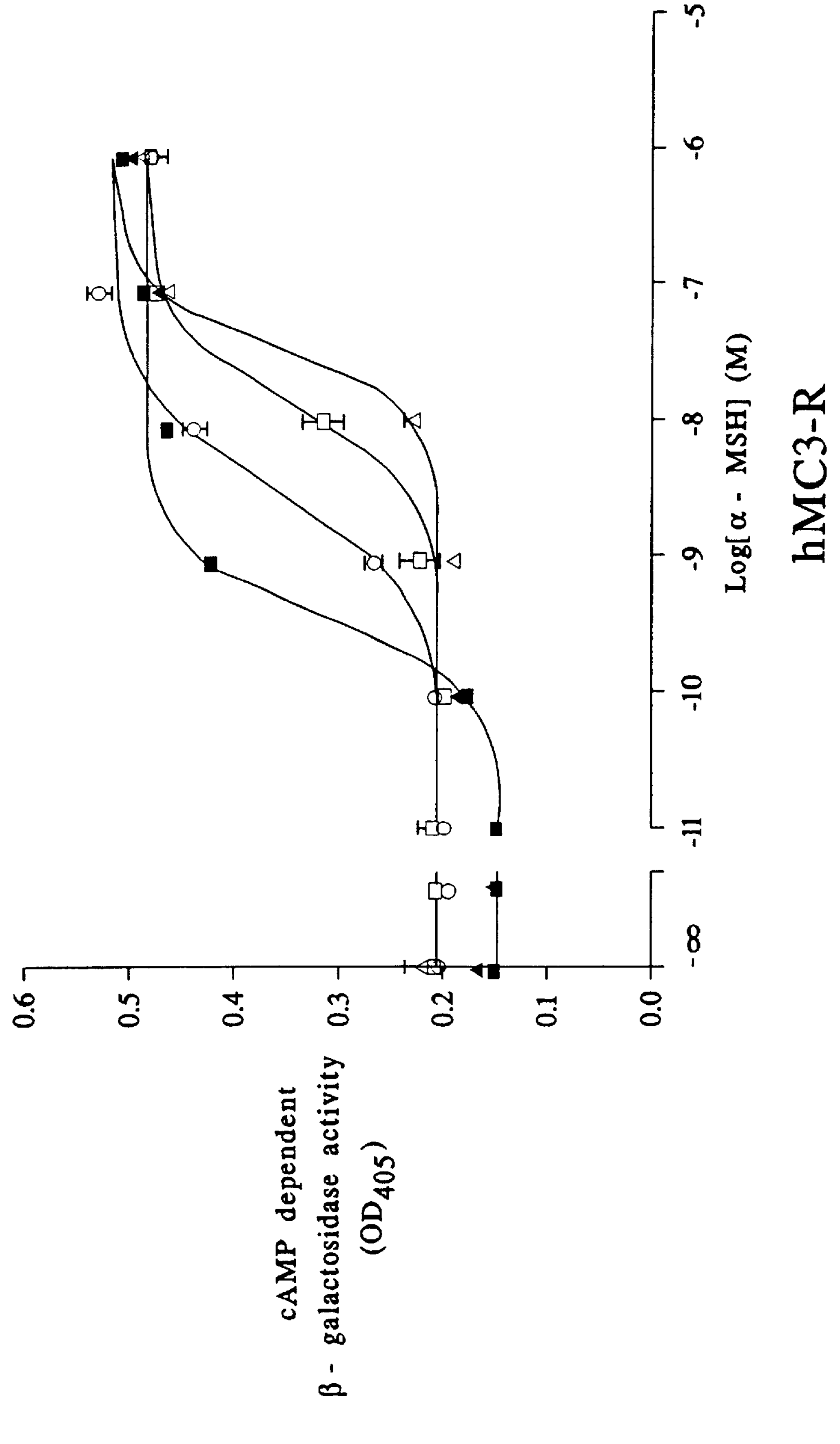
Figure 16C:
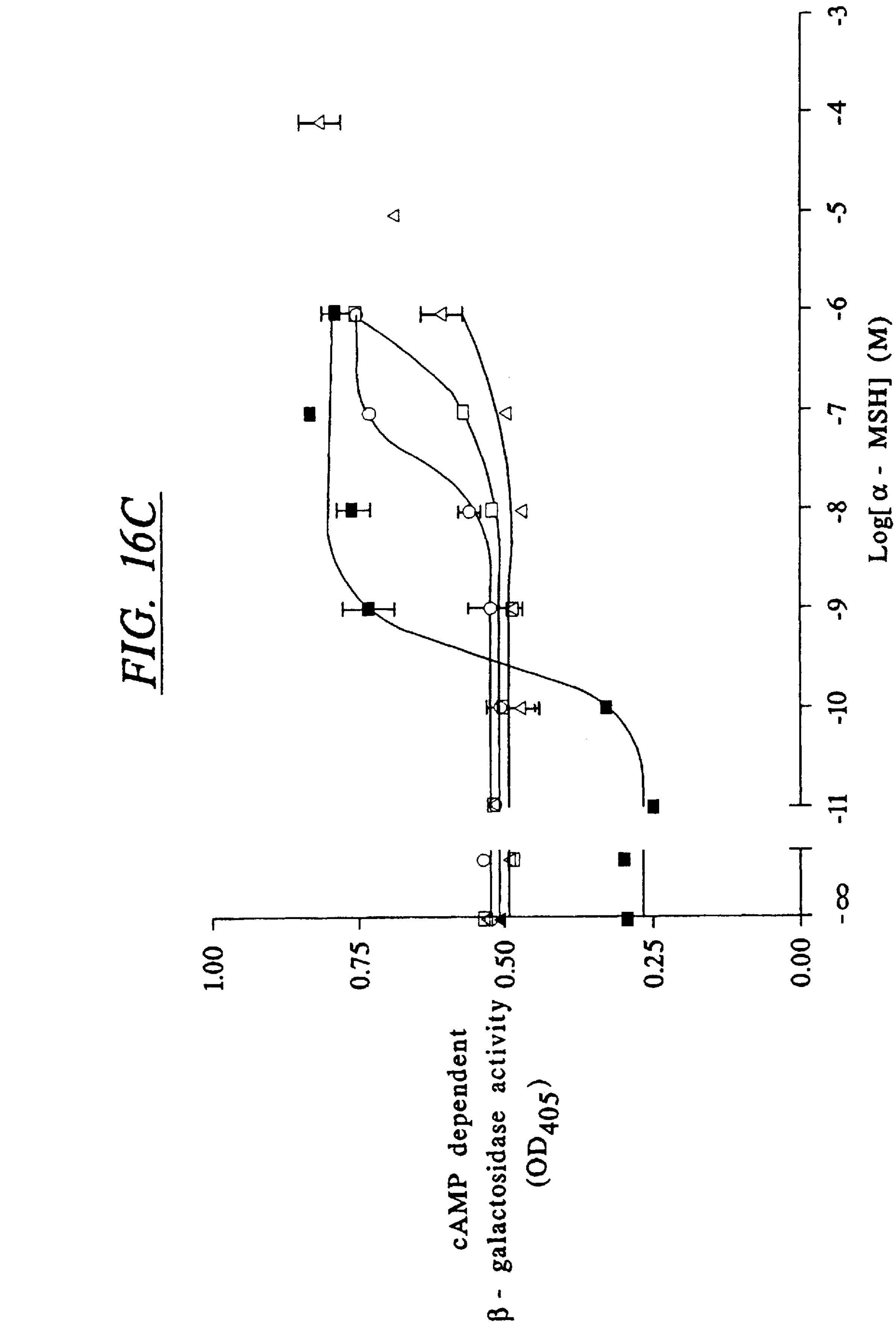
Figure 16D:
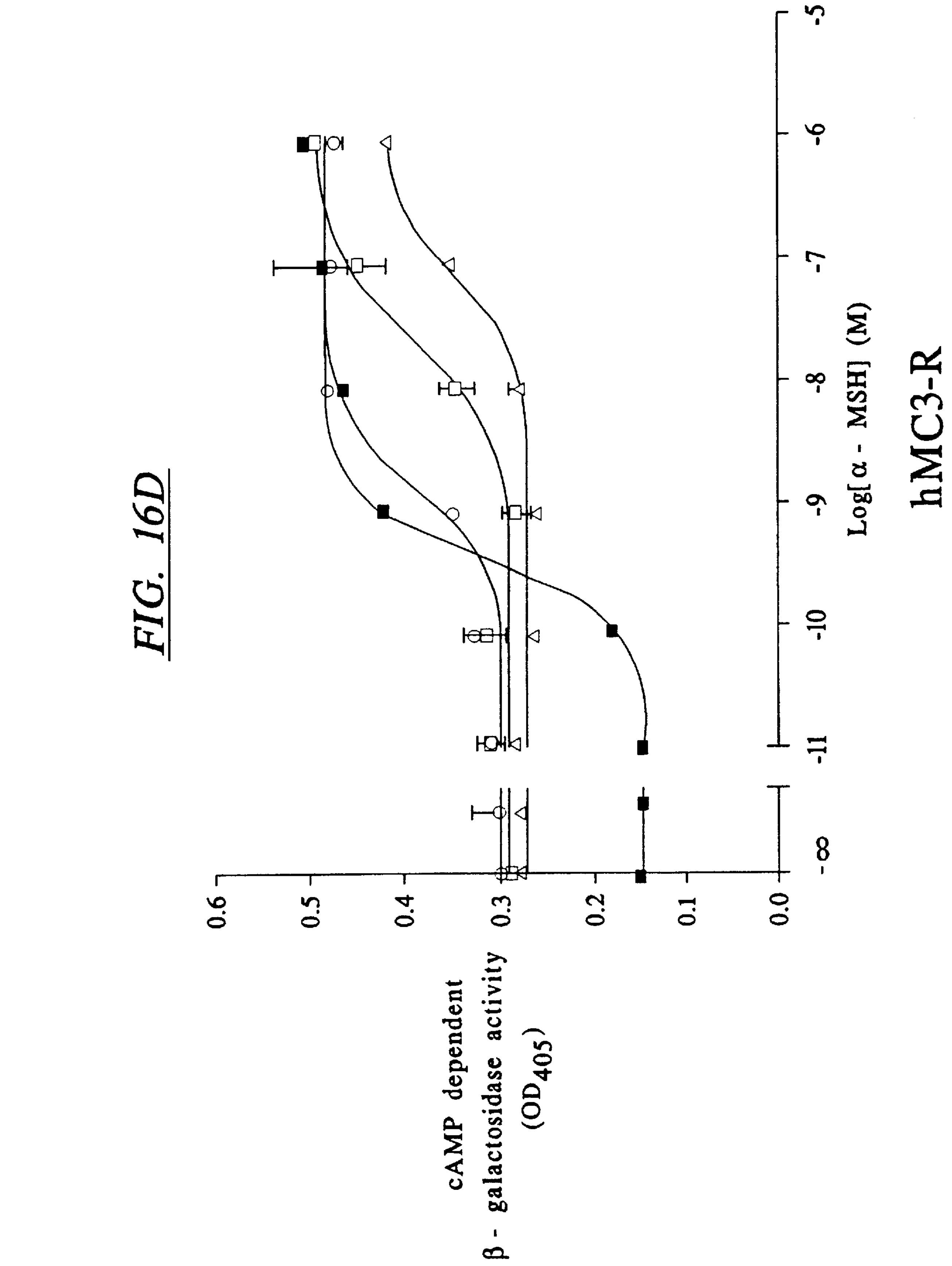

These analogues were tested for melanocortin receptor binding using a colorimetric assay system developed by some of the instant inventors (Chen et al., 1995, *Analyt. Biochem.* 226: 349–354) as follows. A series of concatamers of the synthetic oligonucleotide:

5'-GAATTCGACGTCACAGTATGACGGCCATGG-3' (SEQ ID No:19)

was produced by self-annealing and ligation and a tandem tetramer obtained. This fragment was cloned upstream of a fragment of the human vasoactive intestinal peptide (−93–+152; SEQ ID No.:13; see Fink et al., 1988, *Proc. Natl. Acad. Sci. USA* 85: 6662–6666). This promoter was then cloned upstream of the β-galactosidase gene from *E. coli*. The resulting plasmid construct is shown in FIG. 14.

Transient transfection of the pCRE/β-gal plasmid described above was performed as follows. Cells at between 40–60% confluency (corresponding to about 1.5 million cells/6 cm tissue culture plate) were incubated with Opti-MEM (Gibco BRL, Long Island, N.Y.) and then contacted with a pCRE/β-gal-lipofectin complex which was prepared as follows. 3 μg plasmid DNA and 20 μL lipofectin reagent (Gibco) were each diluted into 0.5 mL Opti-MEM media and then mixed together. This mixture was incubated at room temperature for 15–20 min., and then the mixture (1 mL) added to each 6 cm plate. Transfected plates were incubated at 37° C. for 5–24 h, after which the plates were washed and incubated with DMEM media (Gibco) and the cells split equally into a 96-well culture plate.

To assay melanocortin receptor analogue binding, human 293 cells expressing each of the melanocortin receptors MC-1, MC-3, MC-4 and MC-5, and mouse Y1 cells expressing the MC-2 receptor, were transiently transfected with pCRE/β-gal as described above and assayed as follows. Two days after transfection, cells were stimulated with hormones specific for each receptor or hormone analogue by incubation for 6 h at 37° C. with a mixture comprising $10^{-12}$–$10^{-6}$M hormone or analogue, 0.1 mg/mL bovine serum albumin and 0.1 mM isobutylmethylxanthine in DMEM. The effect of hormone or analogue binding was determined by β-galactosidase assay according to the method of Felgner et al. (1994, *J. Biol. Chem.* 269: 2550–2561). Briefly, media was aspirated from culture wells and 50 μL lysis buffer (0.25M Tris-HCl, pH 8/0.1% Triton-X100) added to each well. Cell lysis was enhanced by one round of freezing and thawing the cell/lysis buffer mixture. 10 μL aliquots were sampled from each well for protein determination using a commercially-available assay (BioRad, Hercules, Calif.). The remaining 40 μL from each well was diluted with 40 μL phosphate buffered saline/0.5% BSA and 150 μL substrate buffer (60 mM sodium phosphate/1 mM $MgCl_2$/10 mM KCV/5 mM β-mercaptoethanol/200 μg/mL o-nitrophenyl-β-D-galactopyranoside) added. Plates were incubated at 37° C. for 1 h and then absorbance at 405 nm determined using a 96-well plate reader (Molecular Devices, Sunnyvale, Calif.). A series of two-fold dilutions from 20 ng of purified β-galactosidase protein (Sigma Chemical Co, St. Louis, Mo.) were assayed in parallel in each experiment to enable conversion of $OD_{405}$ to known quantity of β-galactosidase protein.

The results of these experiments are shown in FIG. 15. This Figure shows the results of the β-galactosidase assay described above using cells expressing each of the MC-1, MC-3, MC-4 or MC-5 receptors and contacted with αMSH or a variety of αMSH analogues, including SHU9119. These results showed that SHU9119 had relatively weak agonist activity for both the human MC-3 and MC-4 receptors.

These results demonstrated the development of a colorimetric assay for cAMP accumulation as the result of melanocortin receptor binding to agonists and antagonists.

The action of MTII, SHU9119, and the endogenous mouse agouti peptide as agonists or antagonists of rodent MC receptors was determined by examining their ability to elevate intracellular cAMP in 293 cell lines expressing the rat MC3-R or mouse MC-4-R (expressed as $IC_{50}$ values representing ligand concentrations required for half-maximal inhibition of binding of $^{125}$I-[Nle$^4$,D-Phe$^7$]α-MSH tracer). Agonist/antagonist activity was also shown by demonstrating inhibition of cAMP elevation by the potent α-MSH analogue [Nle$^4$, D-Phe$^7$]α-MSH, using either a cAMP-responsive β-galactosidase reporter construct as described above, or by direct adenyl cyclase assay as described in Example 3 (wherein $EC_{50}$ values represent ligand concentration required for half-maximal activation of a cAMP-responsive β-galactosidase reporter). Competition binding experiments were determined as the amount of radioactivity bound in the presence of $5\times10^{-6}$M cold [Nle$^4$, D-Phe$^7$]α-MSH, and was typically 3–5% of total counts bound.

In these experiments, murine agouti peptide was produced using a baculovirus system as described by Lu et al., (1994, *Nature* 371: 799–802), with the modification that the agouti peptide was purified from baculovirus supernatants by 0.6M NaCl step elution from an EconoS cation exchange column (BioRad). Agouti peptide used in these assays was approximately 60% pure.

Competition binding assays were performed to determine whether SHU9119 had antagonist activity. towards αMSH binding to either the MC-3 or MC-4 receptors. These assays were performed as follows. Human 293 cells (100,000 cells/well in 24-well plates) expressing either the MC-3 or MC-4 receptors prepared as described above were incubated with a solution of 1 mg/mL BSA in PBS containing 100,000 cpm ($3.1\times10^{-10}$M [$^{125}$I](Nle$^4$, D-Phe$^7$)αMSH and varying concentration αMSH, (Nle$^4$, D-Phe$^7$)αMSH or SHU9119. Cells were incubated for 30 min at 37° C., washed twice with PBS-BSA, lysed with 0.5 mL 0.5N NaOH, and counted using a γ-counter to quantitate the amount of bound [$^{125}$I] (Nle$^4$, D-Phe$^7$)αMSH. Control experiments showed non-specific binding to occur at about 3–5% levels, and this was taken into account when analyzing the experimental results.

Figure 17A:
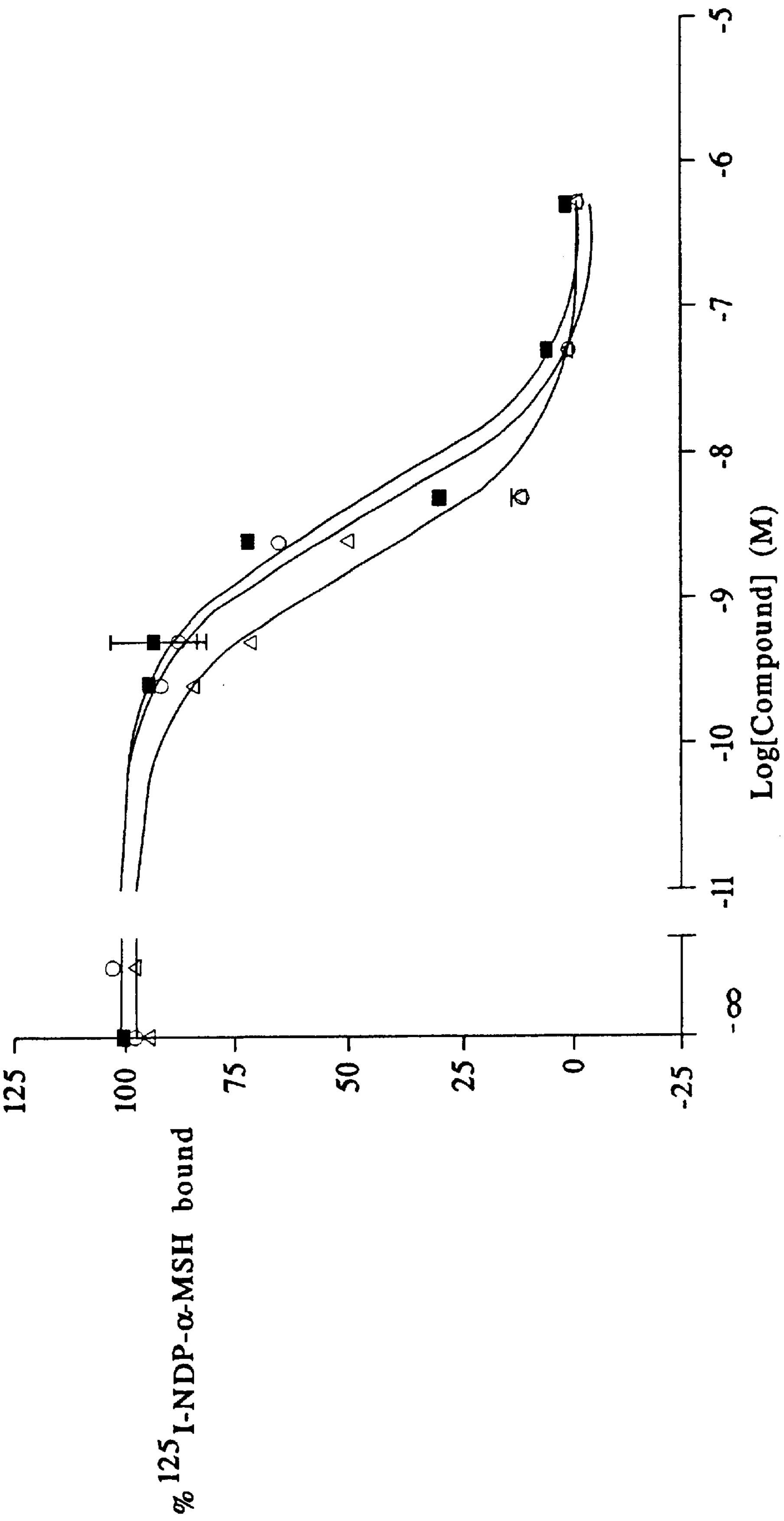
FIG. 17 shows the results of classic competition binding assays using the melanocortin analogues SHU9119 and SHU8914 at the MC3-R and MC-4 R receptors.
Figure 17B:
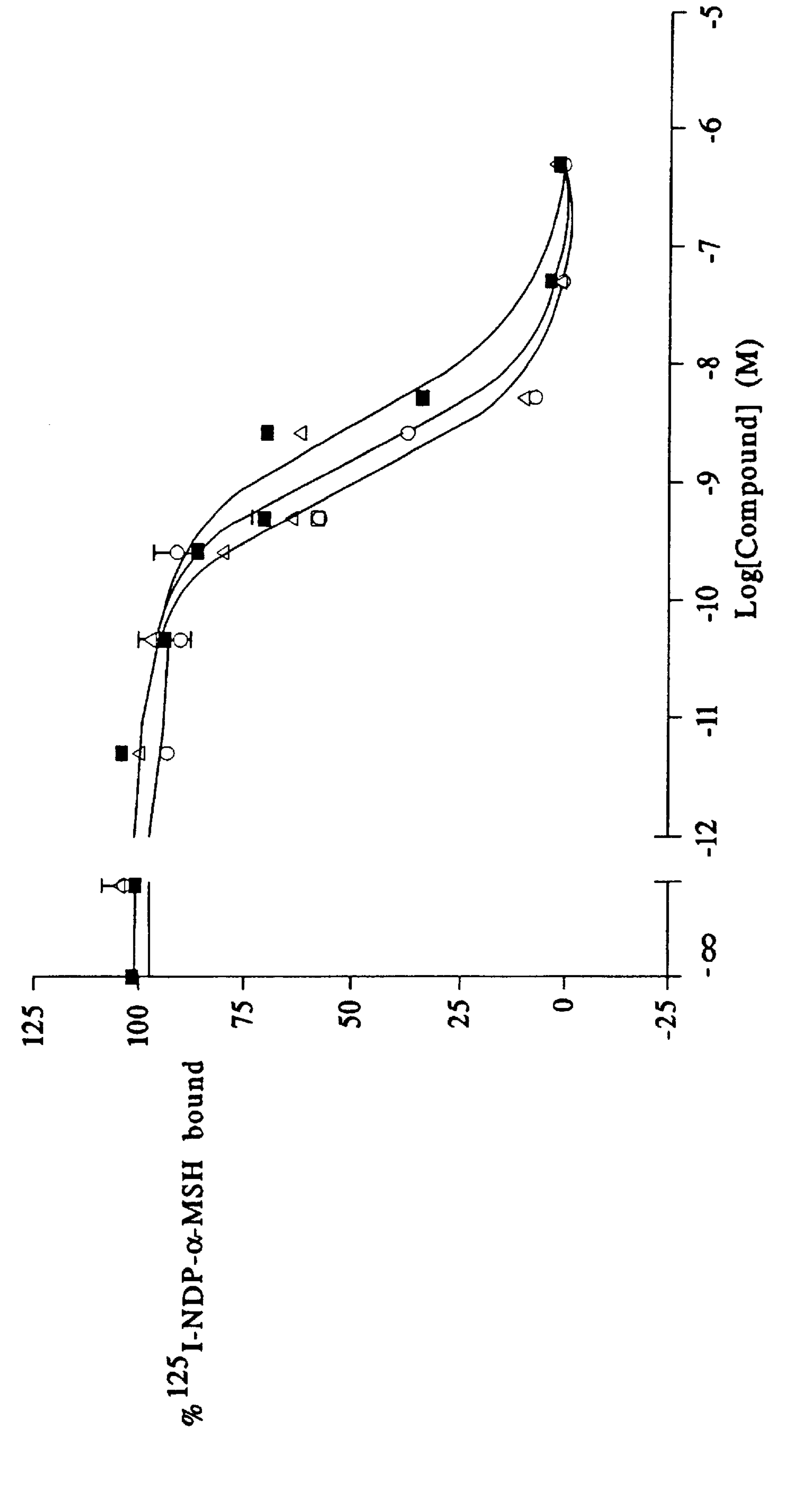

The SHU9119 analogue was found to be a potent antagonist of both the human MC-3 and MC-4 receptors, as shown in FIG. 16. These assays showed $pA_2$ values of 8.3 and 9.3 for the human MC-3 and MC-4 receptors, respectively, as determined using the method of Schild (1947, *Brit. J. Pharmacol.* 2: 189–206). In contrast, no significant alteration in $IC_{50}$ values was detected in binding experiments using this analogue with either the MC-3 or MC-4 receptors (FIG. 17).

Figure 18A:
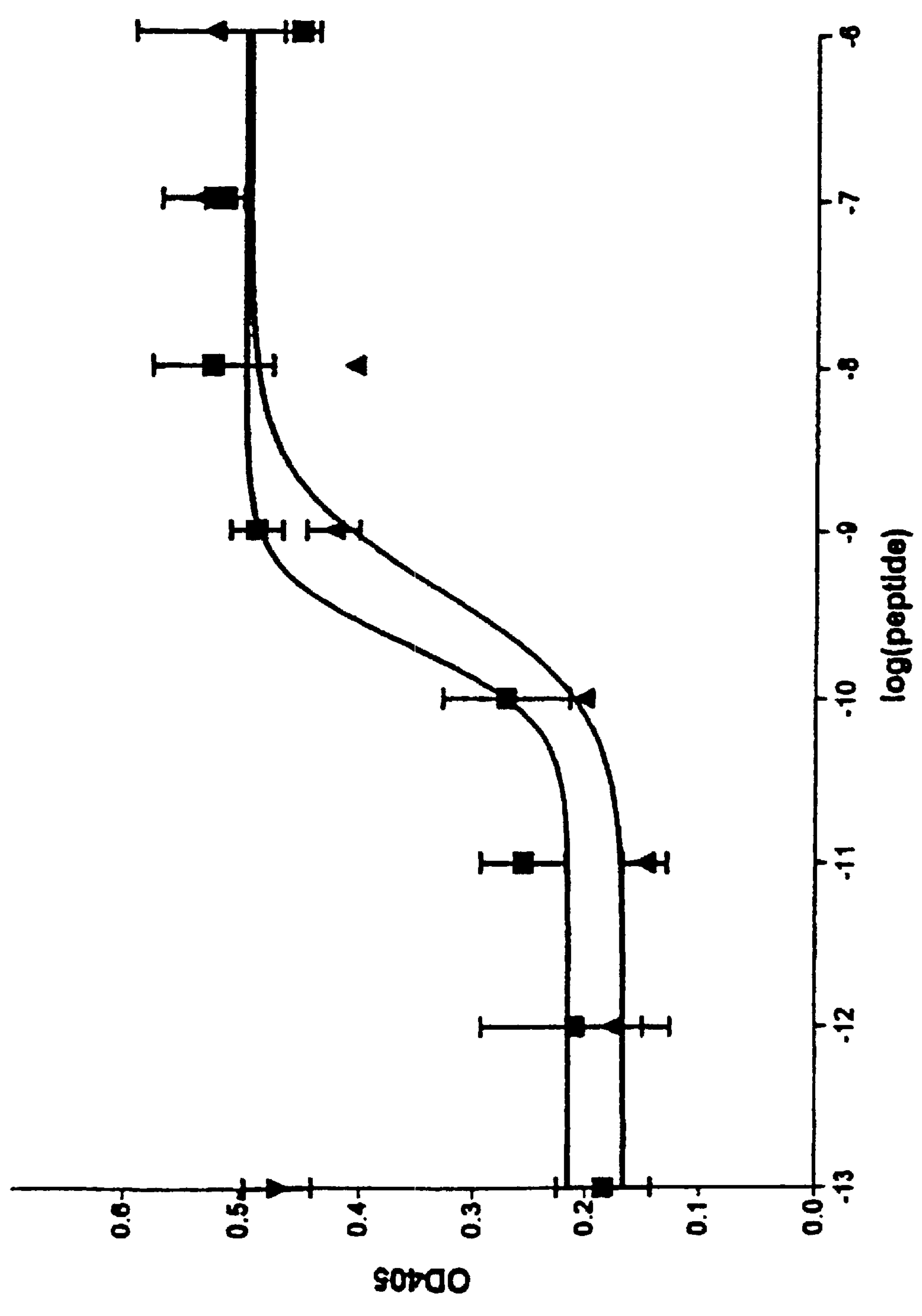
FIGS. 18A and 18B shows the results of cAMP accumulation experiments (performed using the β-galactosidase assay of Example 4) for mouse MC-4 receptor (FIG. 18A) and rat MC-5 receptor (FIG. 18B).
Figure 18:
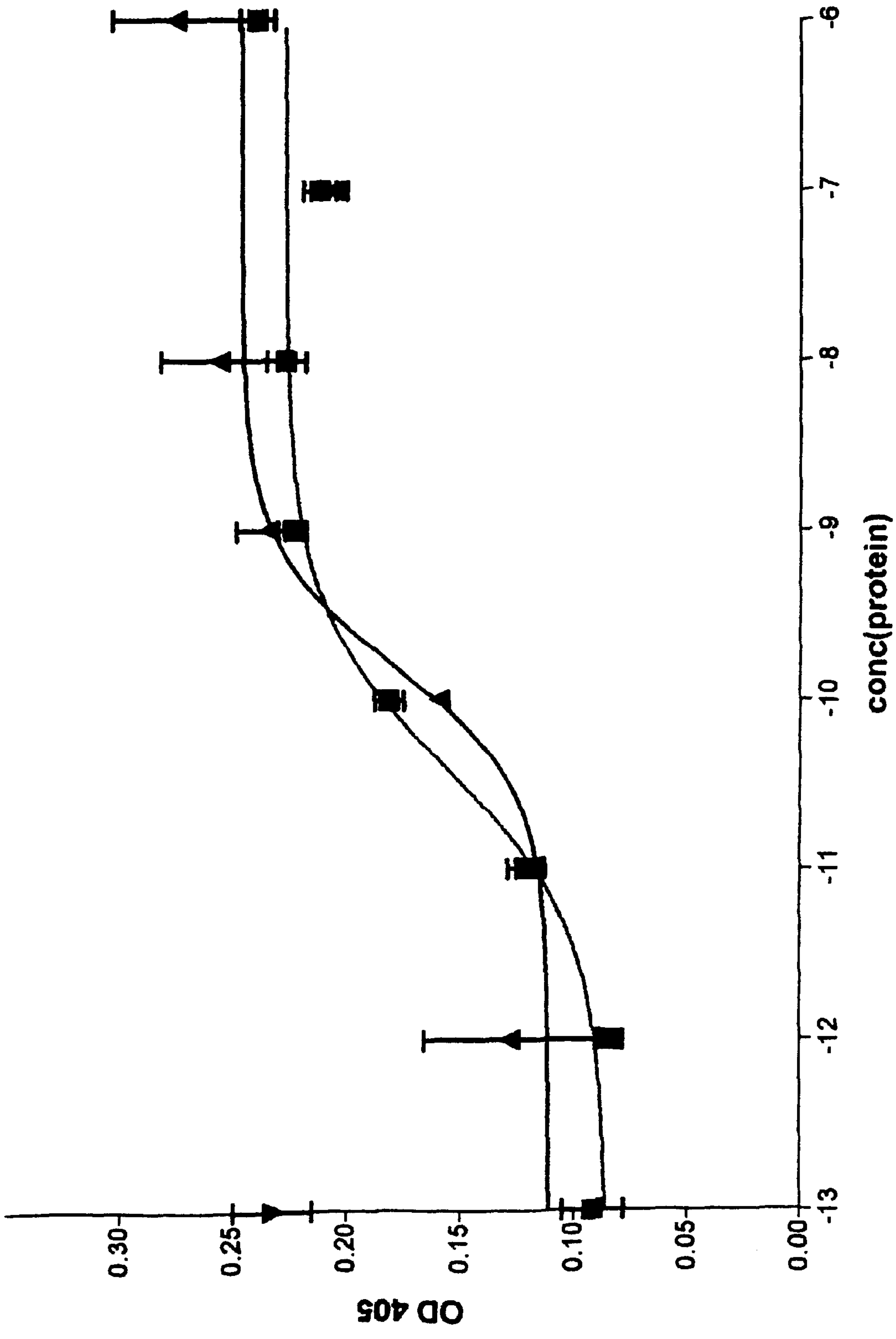

The activity of the MTII analogue was also assayed for melanocortin receptor agonist activity. These results are shown in FIGS. 18A and 18B, and confirmed that the MTII analogue is a specific agonist of the MC-3 and MC-4 receptors.

Specific competition of [Nle$^4$, D-Phe$^7$]α-MSH binding to the rat MC-3 receptor by agouti peptide was observed, although accurate $IC_{50}$ values could not be determined because the peptide preparation was not homogeneous (results not shown). Specific competition of αMSH activation of human MC-4-R by agouti was previously disclosed (Lu et al., 1994, *Nature* 371: 799–802).

EXAMPLE 5

Feeding Behavior Effect of Melanocortin Analogue Binding in Brain

The results shown in Example 4 above suggested a role in the regulation of feeding behavior in mammalian brain for MC receptor agonists and antagonists, in view of the antagonist properties of the agouti peptide at the MC-3 and MC-4 receptors. The agouti peptide was known to cause obesity when expressed ectopically in the mouse, and has been found to be a high affinity antagonist of the melanocyte stimulating hormone receptor (MC1-R) and of the hypothalamic MC-4 receptor (see Lu et al., ibid.). The former activity explained the inhibitory effect of the agouti peptide on eumelanin pigment synthesis. Similarly, it was hypothesized by the inventors that agouti causes obesity in mice by antagonizing hypothalamic MC-4 receptors. The cyclic melanocortin analogue, SHU9119, having been shown herein and elsewhere (Hruby et al.) to be a specific, high affinity antagonist of the central MC-3 and MC-4 receptors, was tested for the effect of direct administration to mouse brain on feeding behavior in the. animals. Intracerebroventricular (ICV) administration of SHU9119 was performed to avoid any complications caused by inhibition of peptide traverse of the blood-brain barrier.

Briefly, male C57B1/6J mice (18–29 g) were maintained on a normal 12 hr/12 hr light dark cycle with food (Purina mouse chow) and water ad libitum. Animals were housed individually for 24 hrs, distributed into experimental and control groups, avoiding any bias as a function of prior weight, then injected with vehicle or vehicle plus drug just prior to the onset of a 12 hr light or dark cycle. Fasted animals were deprived of food from 18:00 to 10:30 hrs to stimulate feeding during the daytime experimental period. Animals were lightly anesthetized with halothane, and administered into one lateral ventricle 2 μL of a solution of artificial cerebrospinal fluid alone (acsf, comprising 130 mM NaCl, 27 mM $NaHCO_3$, 1.2 mM $Na_2$ $HPO_4$, 0.3 mM $NaH_2$ $PO_4$, 0.5 mM $Na_2$ $SO_4$, 1.0 mM $CaCl_2$, 1.0 mM $MgCl_2$, and 2.5 mM KCl), or 6 nmol SHU9119 in acsf. Freehand injections were performed as described by Laursen and Belkunap (1986, *J. Pharmacol. Methods* 16: 355–357) with some modifications. A 10 μl luertip syringe (Hamilton 701LT) was fitted with a 0.5 inch 27 gauge needle. Stiff Tygon tubing was slipped over the needle to expose 3 mM of the needle tip. The syringe was held at a 45° angle from the front of the skull with the bevel facing up. The coronal suture was found by lightly rubbing the needle over the skull. Maintaining the 45° angle, the needle was then inserted 1–2 mm lateral to the midline, using only mild pressure to insert and remove the needle. The compounds indicated in a 2 μl volume of acsf were administered slowly over approximately 15 seconds, and the needle removed after 35 seconds. Animals were allowed to recover from anesthesia and placed into a cage containing a premeasured quantity of food pellets in a spill-free cup. Moribund animals were not included in the study.

Figure 19:
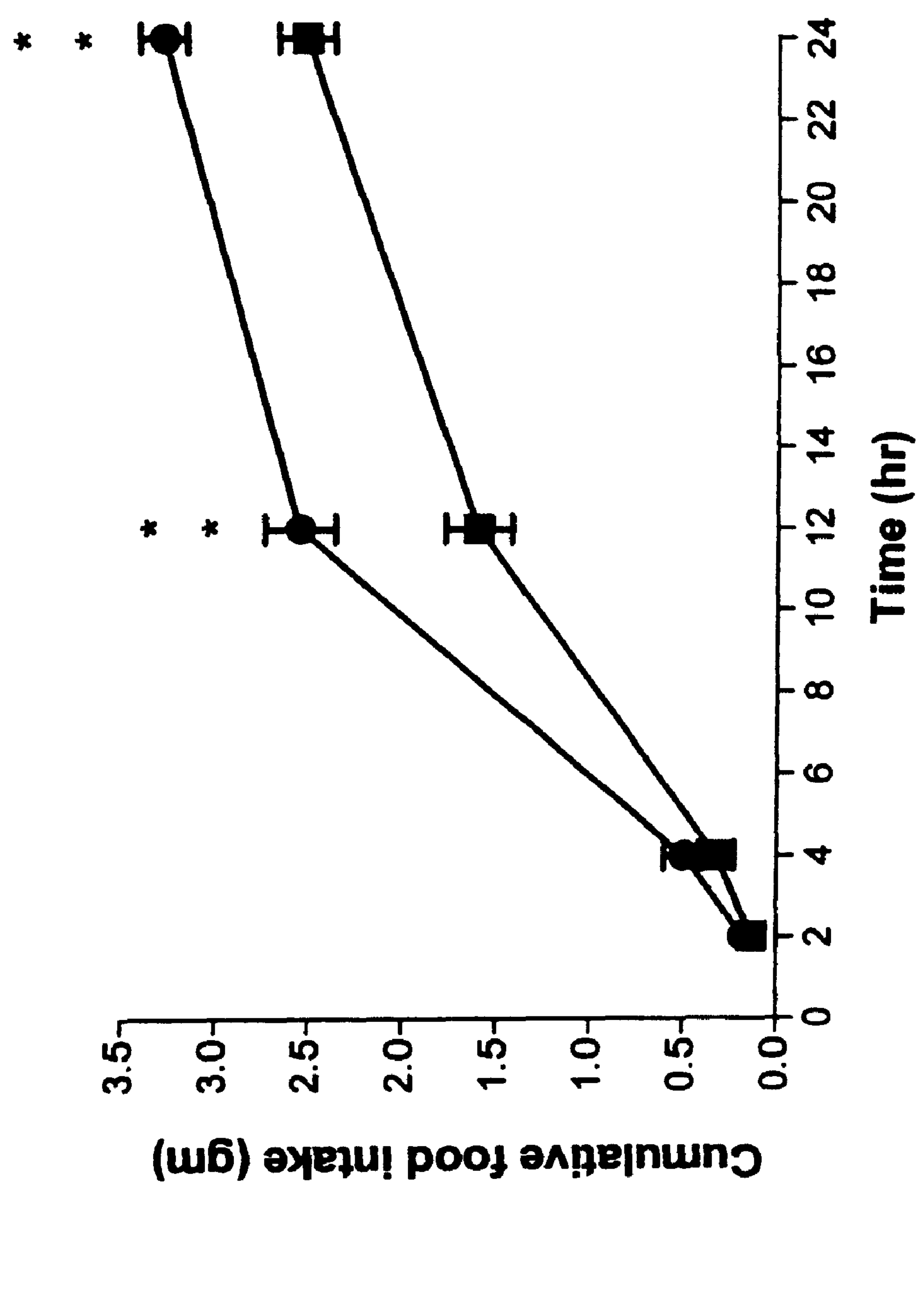
FIGS. 19A through 19C show the effect on food intake of intracerebroventricular administration of melanocortin analogue SHU9119 in mice.
Figure 19:
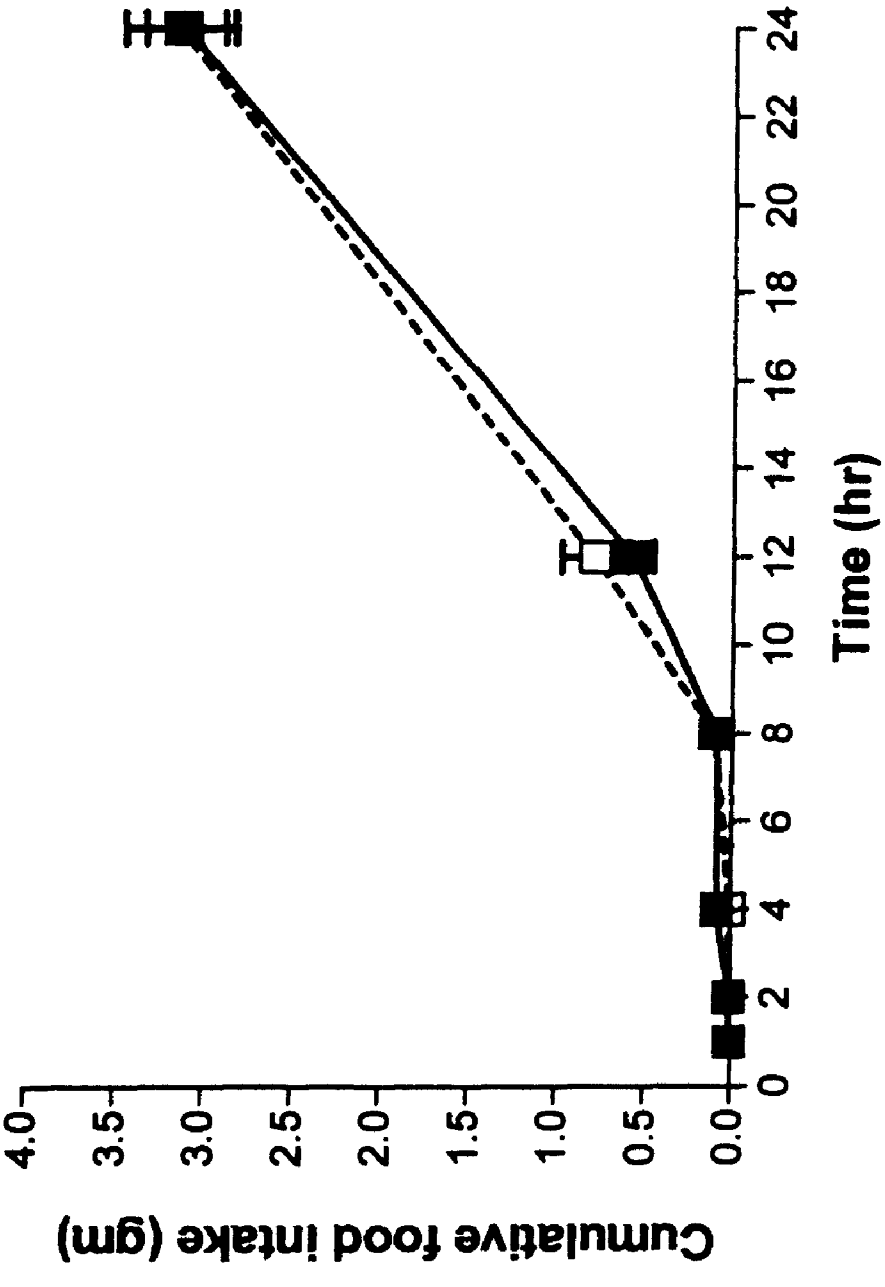
Figure 19:
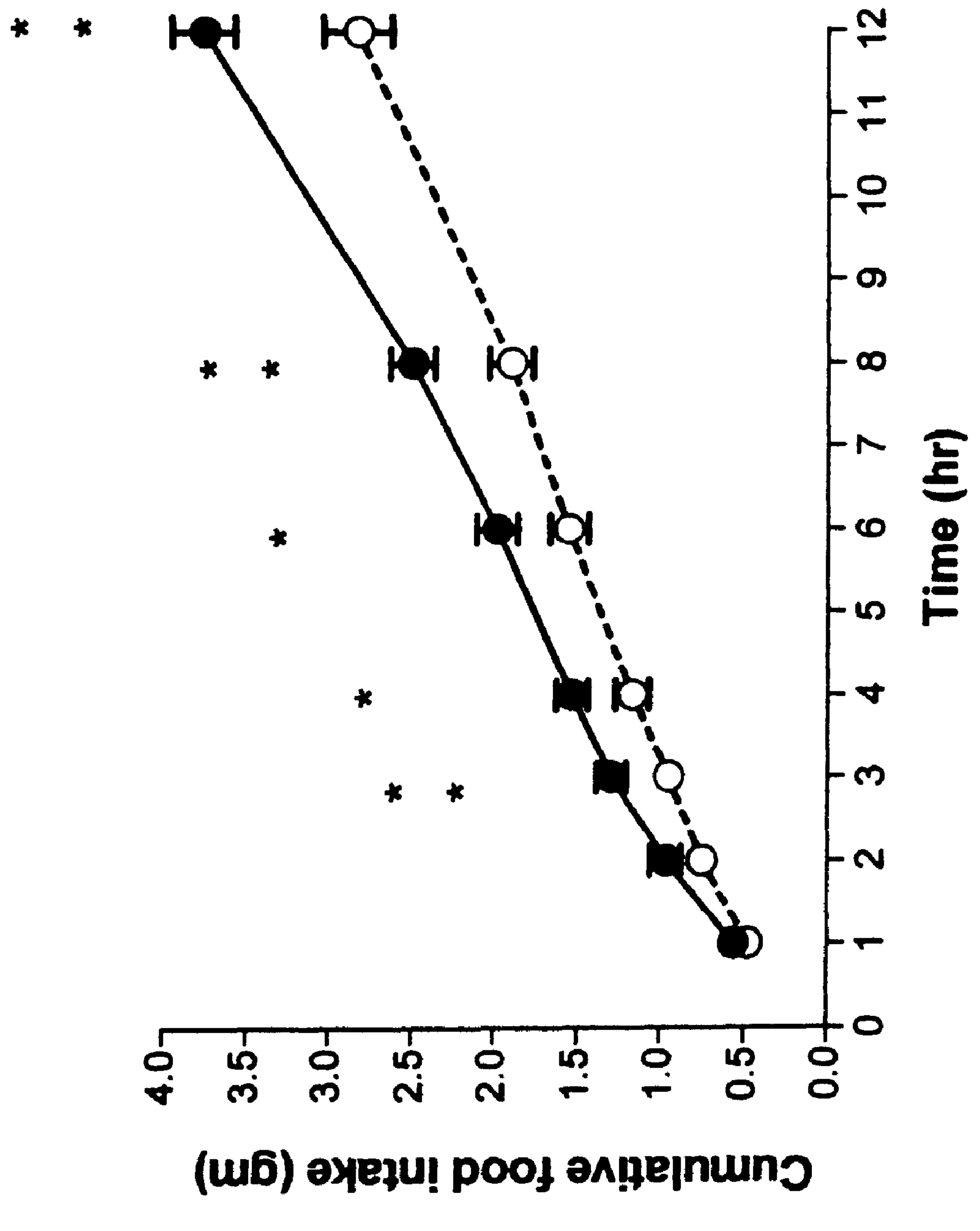

Stimulation of feeding by intracerebroventricular administration of the melan-cortin antagonist SHU9119 is shown in FIGS. 19A through 19C. Curves show cumulative food intake as a function of time following administration of the substances shown. FIG. 19A shows stimulation of feeding by administration of SHU9119just priorto lights off(19:00 hrs) to C57B1/6J mice fed ad libidum. FIG. 19B, in contrast, shows no effect of morning (10:00 hrs) SHU9119 administration in C57B1/6J mice fed ad libidum. FIG. 19C illustrates stimulation of daytime feeding by SHU9119 administration in fasted C57B1/6J mice. In deriving the data points comprising these FIGS., food remaining was briefly removed and weighted at the time intervals indicated. Data points indicate the mean and bars indicate standard error. Significance of the effect over time was determined by ANOVA with repeated measures. Significance of drug effects at individual time points was determined by two-way ANOVA, and is indicated in each Figure (*=P<0.001, =P<0.01, *=P<0.05).

These results demonstrated that ICV administration of SHU9119 into one lateral ventricle of the C57B1/6J mouse just prior to lights out led to a mean 60% increase in food intake over 12 hrs (FIG. 19A; P<0.005). In contrast, daytime food intake in animals fed ad libidum was not stimulated by administration of SHU9119 (FIG. 19B). SHU9119-treatment did, however, significantly stimulate daytime food intake in animals fasted for 16 hrs prior to the experiment (FIG. 19C; P<0.001). Stimulation of feeding was evident at approximately two hrs post-treatment, and continued for 12 hrs, to produce a mean 34% in food intake relative to vehicle-injected controls.

These results supported the hypothesis that agouti or SHU9119 stimulate feeding by antagonizing MC receptors in the central nervous system. To further test this hypothesis, a series of experiments were performed wherein MC receptor agonists were administered to animals primed by fasting to eat, to determine whether feeding in such animals could be inhibited by the MC receptor agonists. Animals were induced to feed by food deprivation for 16 h prior to ICV administration of the non-specific melanocortin agonist MTII. In these experiments, ICV injections in male C57B1/6J mice (20–30 g) and the measurement of food intake were as described above.

Figure 20:
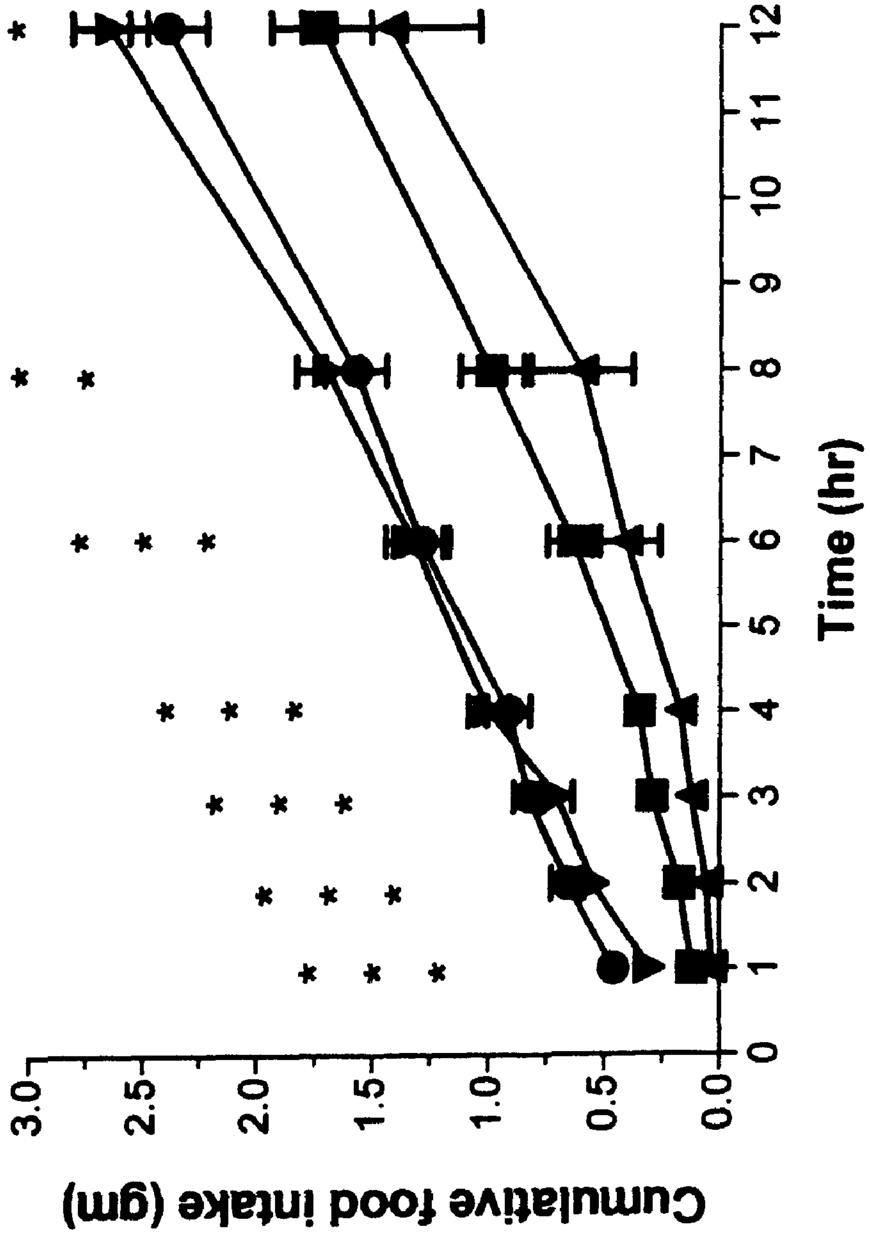
FIGS. 20A through 20C show the effect on food intake of intracerebroventricular administration of melanocortin analogue MTII in mice.
FIG. 20D shows the effect on locomotor activity of intracerebroventricular administration of melanocortin analogue MTII in mice.
Figure 20:
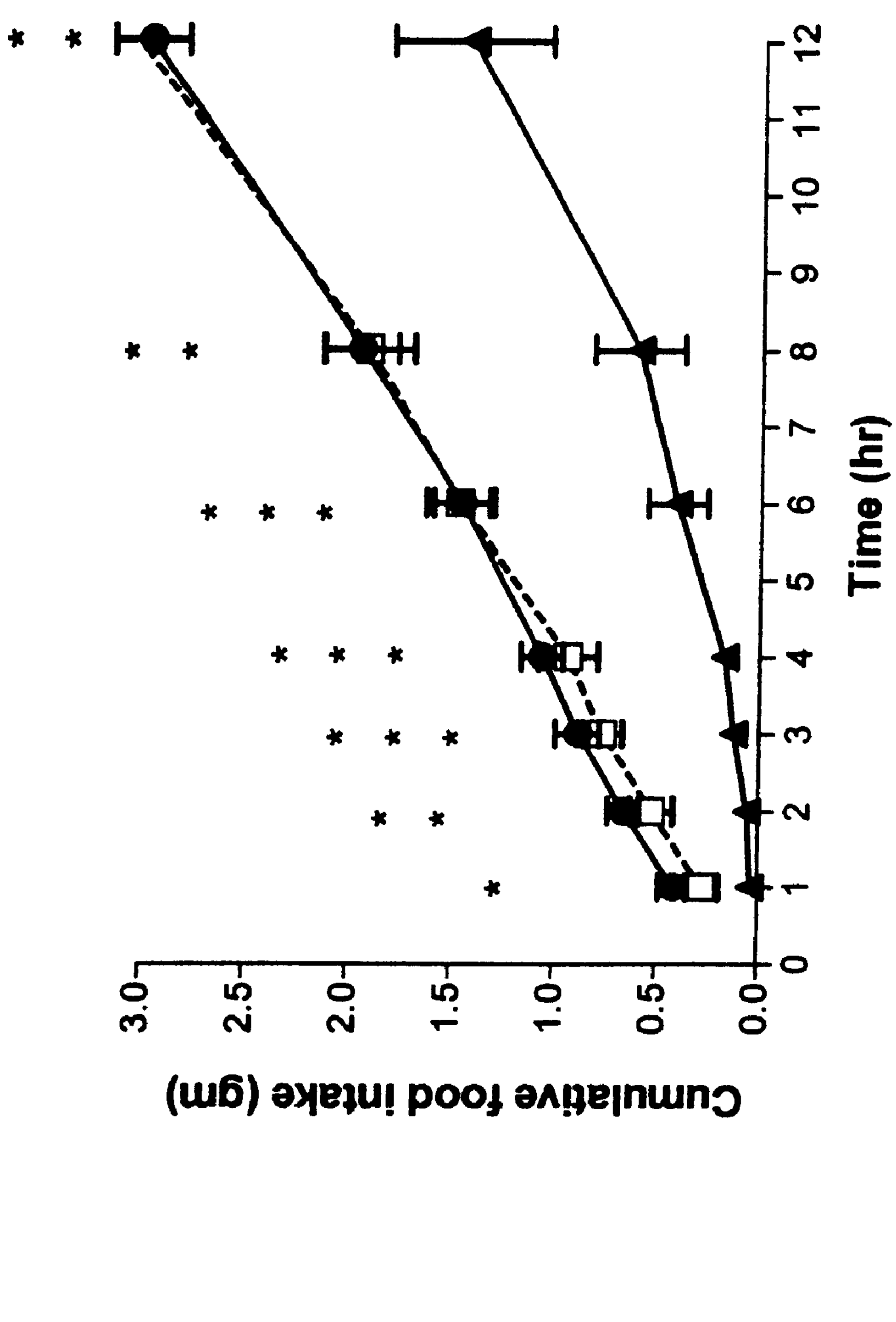
Figure 20:
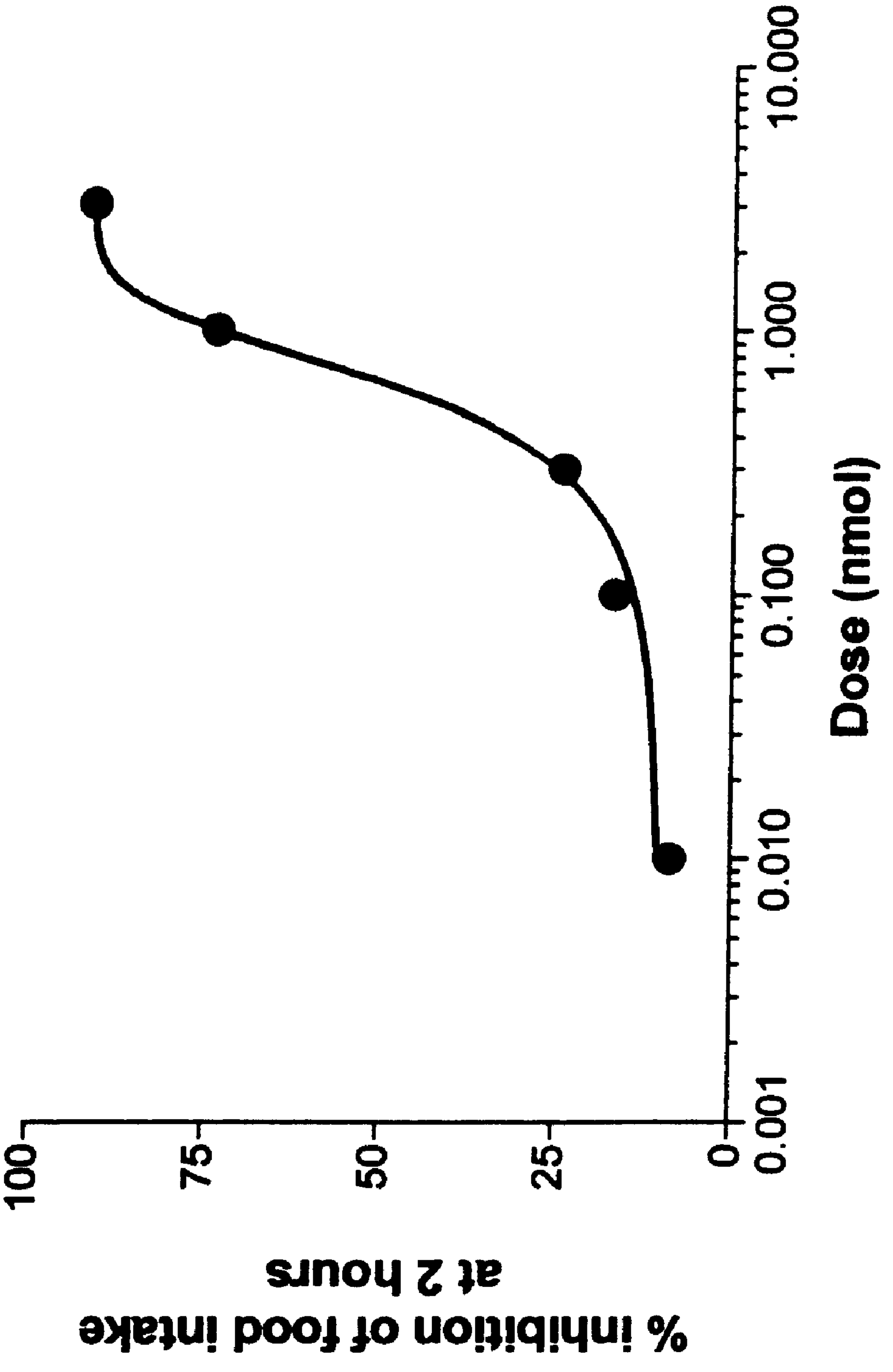
Figure 20:
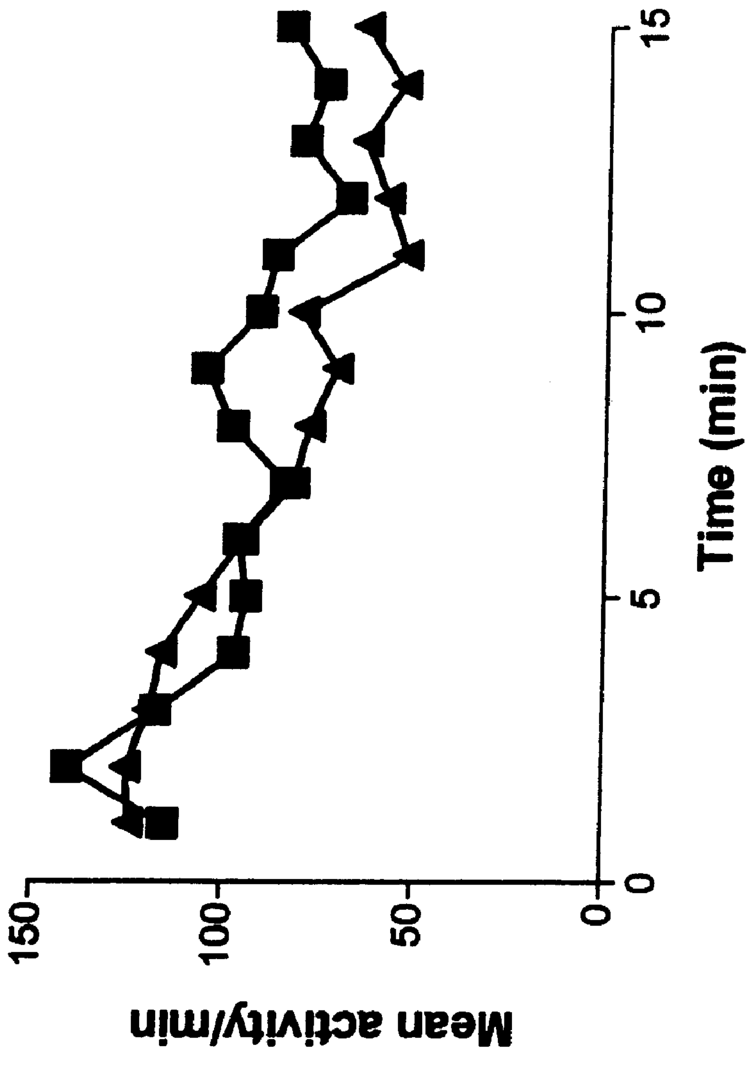

Results of these experiments are shown in FIGS. 20A through 20C. In comparison to vehicle-injected animals, MTII was found to produce a potent inhibition of feeding within one hour after administration (FIG. 20A) in a dose-responsive manner. Food intake was significantly inhibited for up to four hours following administration ($P<0.001$) at the highest dose administered (3 nmol), and decreased food intake continued for the next four hours with normal rates of food intake resuming at about 8 hours after treatment. This dose-responsive inhibition of feeding had an $IC_{50}$ at the two hour time point of approximately 0.5 nmol (FIG. 20C). However, inhibition of feeding with 3 nmol MTII was completely blocked by co-administration of 6 nmol SHU9119 (FIG. 20B; $P<0.001$), demonstrating that the effect results specifically from agonist binding to the MC-4 and/or MC-3 receptor.

Locomotor assays were performed to determine whether the effects on feeding behavior observed in these mice were secondary to generalized behavioral effects caused by administration of these melanocortin analogues. The effects of MTII on locomotor activity were tested by placing vehicle or MTII-treated mice in sound and light-proof cages containing multiple light beam detectors. These assays were performed by first injecting 3 nmol MTII or acsf as described above. At three hours (2:45–3:25) post-injection, 12 mice were placed into 12 separate boxes containing multiple infrared light sources and photodetectors. The boxes were contained within separate ventilated light and sound attenuating chambers (Coulboum model E10–20). Disruption of the infrared beams, with a 10 msec. resolution, was tallied independently for each one minute time period in each cage. The results of these assays are shown in FIG. 20D. Data points indicate the mean total activity (# of light breaks) for 6 animals in each experimental group. Four way Anova statistical analysis was used to analyze the data, and indicated an absence of a significant difference among the two groups.

Inhibition of feeding by MTII could not be explained by any apparent behavioral abnormalities, or any effect on arousal or locomotor activity. MTII-treated animals appeared alert and exhibited no unusual behavior relative to controls. At approximately three hours after ICV administration, MTII-treated animals exhibited locomotor activity that was indistinguishable from vehicle-treated animals (FIG. 20D). The higher initial activity, indicative of exploratory behavior, and continued locomotion over a 15 min period was indistinguishable between the two groups, indicating that the inhibition of feeding was not due to decreased locomotion or decreased arousal.

Figure 21:
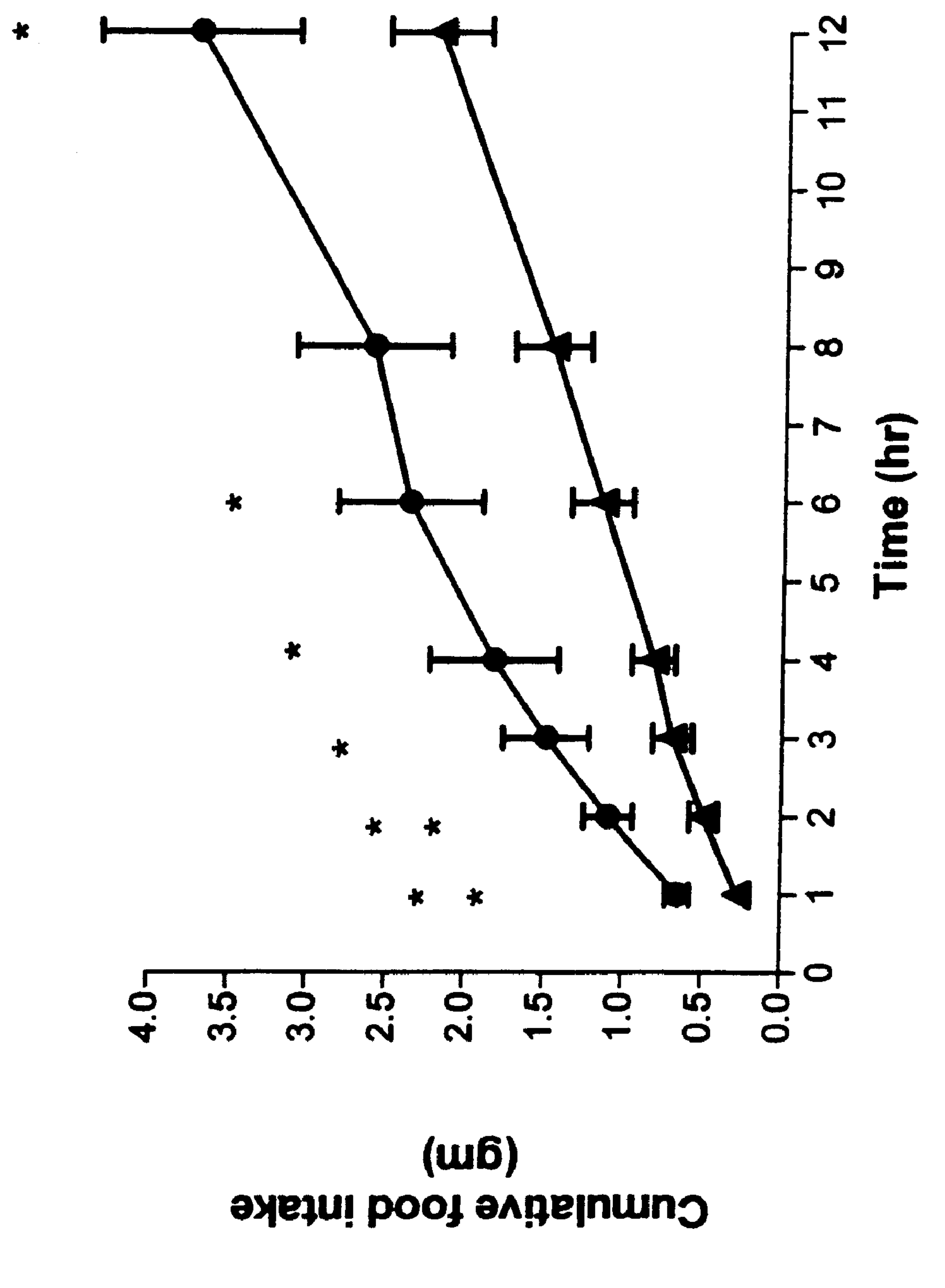
FIGS. 21A through 21D show the effect on food intake of intracerebroventricular administration of melanocortin analogue MTII in mice.
Figure 21:
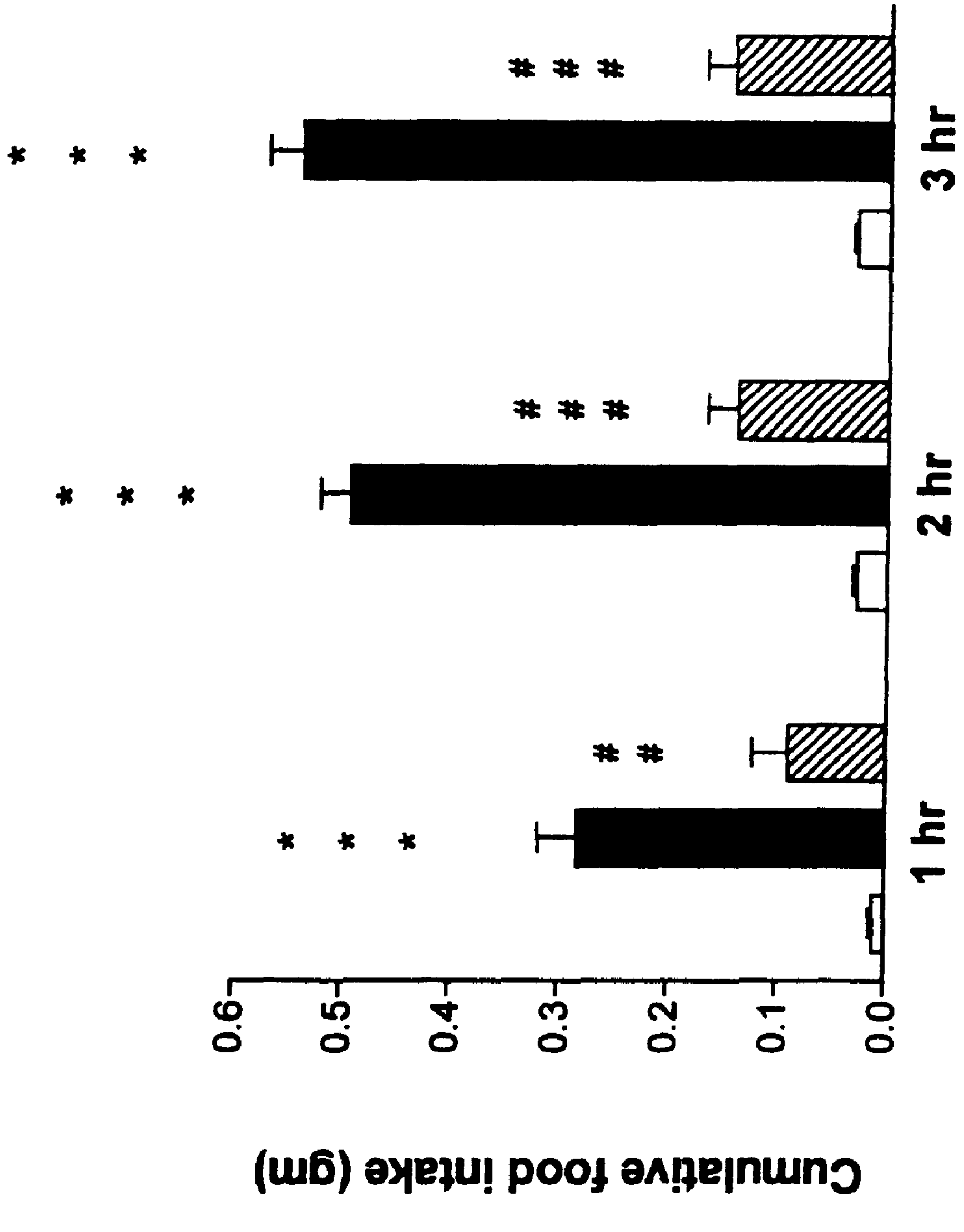
Figure 21:
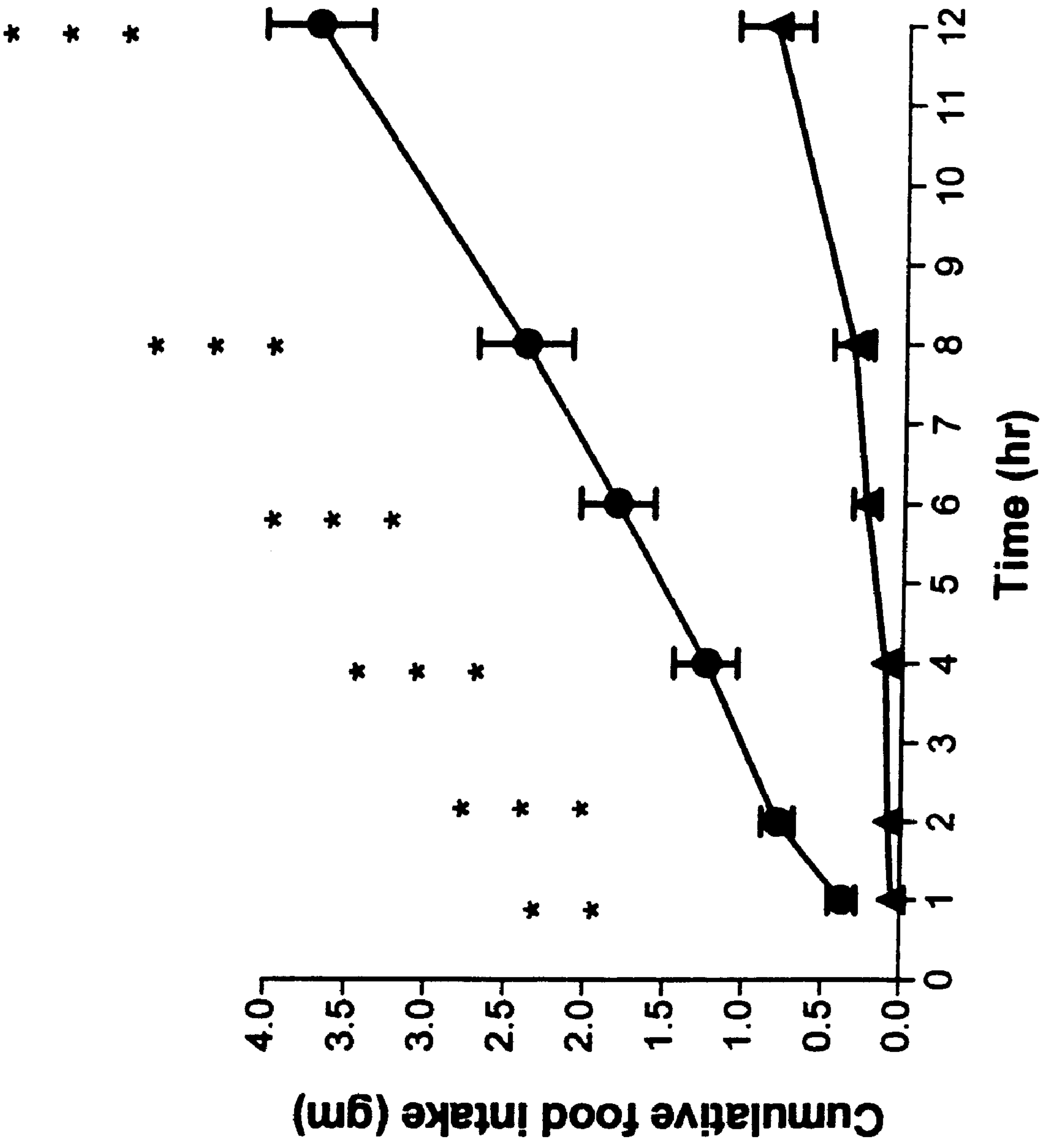
Figure 21:
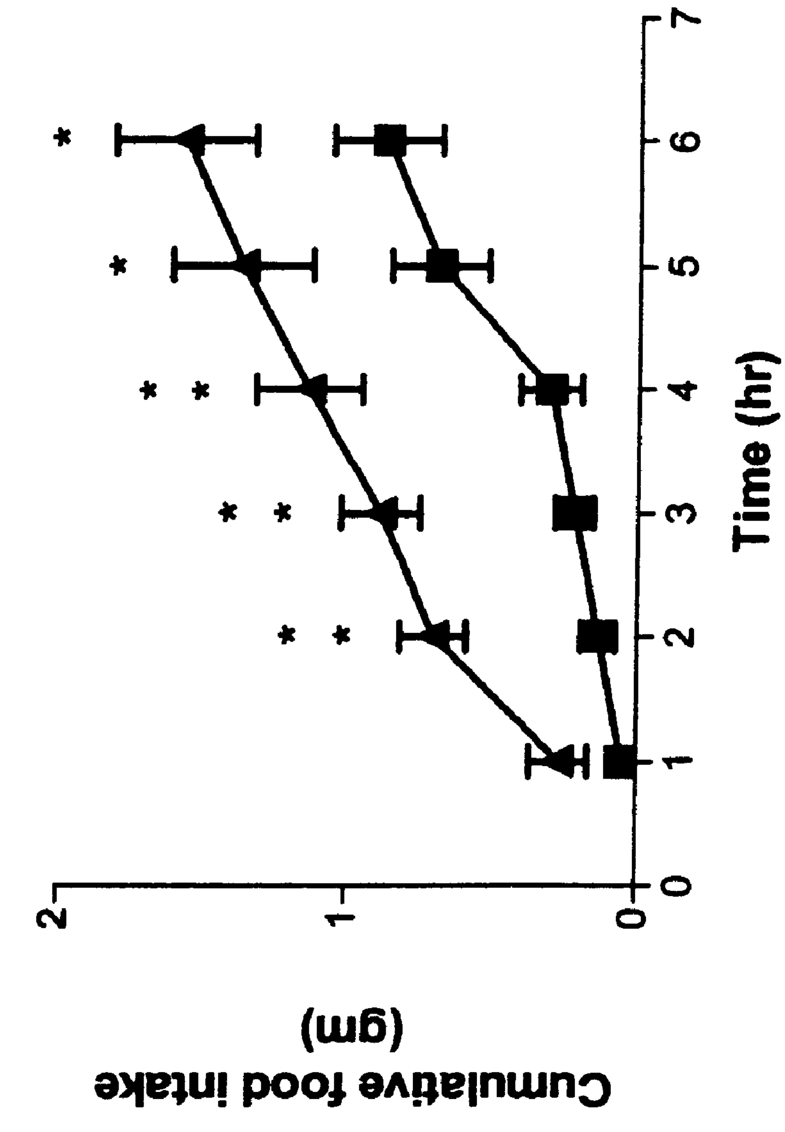

The administration of MTII also inhibited food intake in three other models of hyperphagia: the C57B1/6J-$Lep^{ob}$ mouse, C57B1/6J-$A^Y$ mouse, and NPY-injected C57B1/6J mouse. FIG. 21A shows inhibition of feeding by intracerebroventricular administration of MTII in $A^Y$ mice (females, 19–28 gms). FIG. 21B shows inhibition of feeding by intracerebroventricular administration of MTII in C57B1/6J mice (females, 21–25 gm) stimulated to feed by co-administration of neuropeptide Y. FIG. 21C shows inhibition of feeding by intracerebroventricular administration of the MTII in ob/ob mice (females, 48–69 gms). FIG. 21D shows inhibition of feeding in ob/ob mice intraperitoneal administration of MTII (females, 40–45 gms). ICV injections and measurement of food intake was performed as described above, with the exception of NPY treated animals, which were not fasted prior to experimentation. Animals treated intraperitoneally received 100 $\mu$l of a 1 mM solution of MTII in saline, and vehicle injections consisted of the same value of saline alone. Significance indicated for individual time points, determined as described above, was for 3 nmol MTII vs. acsf(FIG. 21A), 1.18 nmol NPY vs. 1.18 nmol NPY+3 nmol MTII (FIG. 21B), 3 nmol MTII vs. acsf (FIG. 21C), and 100 nmol MTII vs. saline (FIG. 21D).

The hyperphagia in these models can be clearly seen by comparing the 12 hr food intake following a fast in vehicle-injected C57B1/6J (2.4 g, FIG. 19A), C57B1/6J-$A^Y$ (3.7 g, FIG. 21A) and C57B1/6J-$Lep^{ob}$ (3.7 g. FIG. 21C) animals. As expected, MTII treatment inhibited food intake following a 16 hr fast in the C57B1/6J-$A^Y$ mouse (FIG. 21A; $P<0.05$). Interestingly, while food intake for the first four hours is significantly inhibited relative to vehicle-injected animals, it is also significantly less inhibited in the C57B1/6J-$A^Y$ animal than in the C57B1/6J animal given the same 3 nmol dose (compare, FIG. 20A versus FIG. 21A, 1–4 hrs; $P<0.001$). The decreased effectiveness of the agonist in the presence of the $A^Y$ allele is consistent with the proposal that his allele results in chronic expression of agouti peptide melanocortin antagonist in the brain.

MTII, upon co-administration, also significantly inhibited the profound stimulation of feeding induced by neuropeptide Y (NPY), measured over a three hr period (FIG. 21C; $P<0.005$). Co-administration of an approximately two-fold molar excess of MTII produced a 74% inhibition of NPY-stimulated food intake at the three hour time point.

Finally, MTII also inhibited hyperphagia due to absence of leptin in the C57B1/6J-$Lep^{ob}$ mouse (FIG. 21C; $P<0.001$). MTII blocked feeding as potently (FIG. 20A), in contrast to the less potent inhibition described above for the C57B1/6J-$A^Y$ mouse.

The C57B1/6J-$Lep^{ob}$ animal was also used to test the ability of MTII to regulate feeding when administered peripherally. Moderate doses (100 nmol) of MTII were inhibited feeding in the C57B1/6J-$Lep^{ob}$ mouse ($P<0.001$) while low doses (10 nmol) did not (date not shown). The kinetics were similar to those seen with ICV administration, with a potent inhibition of feeding for the first four hours. The 100-fold higher dose required peripherally, as well as the similar kinetics suggest a primarily central mechanism of action of MTII.

These data show that melanocortinergic neurons exert a tonic inhibition of feeding behavior, and that disruption of this signal leads to hyperphagia. With regard to the recently-discovered leptin hormone made by adipocytes, which is generally expressed at elevated levels in obese humans and rodents (such as the C57B1/6J-$Lep^{ob}$ animal), the regulatory defect is understood to be an incapacity to respond properly to the leptin hormone signal. The instant results indicate that the melanocortins act independently, or physiologically "downstream," from the leptin hormone/receptor interaction, because it has been shown herein that melanocortin receptor agonists can potently inhibit feeding in the C57B1/6J-$Lep^{ob}$ animal.

These results suggest that MC receptor agonists and antagonists can affect mammalian feeding behavior, and provide a means for determining candidate compounds for the development of effective pharmacological products directed towards alleviating such human ailments as obesity, anorexia and cachexia.

EXAMPLE 6

Use of MC Receptor-Expressing Recombinant Cells for Screening Compounds that Affect Feeding Behavior in Mammals The results obtained in Example 6 indicated that cells expressing a variety of mammalian melanocortin receptors are useful for characterizing compounds as a first step towards developing MC receptor agonists and antagonists for controlling feeding behavior in mammals, particularly obesity and overweight disorders in general, as well as anorexia, cachexia and other failure-to-thrive disorders.

A panel of mammalian melanocortin receptor-expressing recombinant cells are provided as described above in Example 3, wherein each member of the panel comprises appropriate mammalian cells, such as human 293 cells, comprising a recombinant expression construct encoding the MC-1, MC-2 (ACTH), MC-3, MC-4 or MC-5 receptor, the panel constructed to comprise cells functionally expressing each of these MC receptor proteins.

The panel is used as follows. Receptor agonist activity is assayed by transient or stable expression of a protein which produces a metabolite reporter molecule in response to receptor binding by any of the MC receptor proteins. An example of such a reporter system is the recombinant expression construct described in Example 4, wherein cAMP responsive elements (CREs) are operatively linked to bacterially-derived β-galactosidase (β-gal) gene. In the event of receptor binding, cAMP is produced in the mammalian cell, and the CRE induces β-gal expression. When co-incubated with a colorless substrate for β-gal, receptor binding results in conversion of the colorless substrate to a blue-colored product, which can be easily scored visually or spectrophotometrically. Alternative reporter genes, such a luciferase, can also be used as reporter systems, provided that expression of the reporter molecule-producing protein is functionally linked to receptor binding of a test compound. Alternatively, cAMP production resulting from MC receptor binding can also be measured directly. Additionally, the cell panel or membranes from these cells can be used for direct radioligand binding assays.

Assay panels are arranged so that agonist activity can be identified, quantitated and correlated with expression of each MC receptor. Automated assays using such panels are also envisioned, whereby the qualitative and quantitative detection of a reporter metabolite is detected in an array (such as a 96-well tissue culture plate) and the data collected and assembled into a computer data-base or other analytical program.

Antagonist activity is detected by a modification of the above assay. In this assay, the inhibition of production of an amount of a known receptor agonist, specific for each receptor, is assayed in the presence of a putative antagonist compound. Production of metabolite reporter molecules and their qualitative and quantitative detection is achieved as described above, and the specificity and potency of each antagonist compound characterized with regard to the degree of inhibition achieved for each receptor.

In view of the instant disclosure, MC-3/MC-4 receptor antagonists are expected to be useful to inhibit food intake in a hungry animal, and MC-3/MC-4 receptor agonists are expected to be useful to increase food intake in an animal. Alternative patterns of feeding behavior associated with different patterns of MC receptor agonist/antagonist activity can be determined using this assay.

Compounds having agonist or antagonist activity with the MC-3 or MC-4 receptors detected using this assay are further screened in vivo to determine whether the observed receptor binding activity results in modification of feeding behavior when administered to an animal. In these assays, the MC receptor binding compounds detected using the assay are administered intracerebroventricularly as described above in Example 5 to animals after an overnight fast, to waking animals, or to animals that are not otherwise primed to be hungry. Feeding and locomotor activity is monitored in these animals, and compounds affecting eating behavior (either by inhibiting feeding in otherwise hungry animals or stimulating feeding in otherwise sated animals) are selected for further development.

In addition, systemic administration of compounds found to be active by ICV administration assays is used to screen such compounds for the ability to cross the blood-brain barrier. Such compounds are also useful as templates for modifications aimed at increasing the availability of these compounds in the brain after systemic administration, for increasing bioactivity, or both.

It should be understood that the foregoing disclosure emphasizes certain specific embodiments of the invention and that all modifications or alternatives equivalent thereto are within the spirit and scope of the invention as set forth in the appended claims.

We claim:

1. A compound having the general formula:

A-B-C-D-E-F-G-amide wherein A is Leu, Ile, or Met;

B is Asp or Glu;

C is His;

D is D-Phe, D-Tyr or D-Nal;

E is Arg, Lys, homoArg or homoLys;

F is Trp;

G is Lys or homoLys;

wherein the peptide is cyclized by the formation of an amide bond between the side chain carboxyl group of the Asp or Glu residue at position B in the peptide, and the side chain amino group of the Lys or homoLys residue at position G, and wherein the compound is an agonist of MC-3 melanocortin receptor.

* * * * *

```
                         SEQUENCE LISTING


(1) GENERAL INFORMATION:

   (iii) NUMBER OF SEQUENCES: 19


(2) INFORMATION FOR SEQ ID NO: 1:

     (i) SEQUENCE CHARACTERISTICS:
          (A) LENGTH: 35 base pairs
          (B) TYPE: nucleic acid
          (C) STRANDEDNESS: single
          (D) TOPOLOGY: linear

    (ii) MOLECULE TYPE: DNA (genomic)
```

-continued (ix) FEATURE:
(A) NAME/KEY: misc_feature
(B) LOCATION: 1..35
(D) OTHER INFORMATION: /function = "Degenerate oligonucleotide primer (sense)"
/note= "The residue at positions 24 and 24 are inosine"

(xi) SEQUENCE DESCRIPTION: SEQ ID NO: 1:

```
GAGTCGACCT GTGYGYSATY RCNNTKGACM GSTAC                          35
```

(2) INFORMATION FOR SEQ ID NO: 2:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..32
(D) OTHER INFORMATION: /function = "Degenerate oligonucleotide primer (antisense)"
/note= "The residue at position 18 is inosine"

(xi) SEQUENCE DESCRIPTION: SEQ ID NO: 2:

```
CAGAATTCAG WAGGGCANCC AGCAGASRYG AA                             32
```

(2) INFORMATION FOR SEQ ID NO: 3:

(i) SEQUENCE CHARACTERISTICS:
(A) LENGTH: 1260 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: 5'UTR
(B) LOCATION: 1..14

(ix) FEATURE:
(A) NAME/KEY: CDS
(B) LOCATION: 15..959

(ix) FEATURE:
(A) NAME/KEY: 3'UTR
(B) LOCATION: 960..1260

(xi) SEQUENCE DESCRIPTION: SEQ ID NO: 3:

```
TTCCTGACAA GACT ATG TCC ACT CAG GAG CCC CAG AAG AGT CTT CTG GGT       50
                Met Ser Thr Gln Glu Pro Gln Lys Ser Leu Leu Gly
                  1               5                  10

TCT CTC AAC TCC AAT GCC ACC TCT CAC CTT GGA CTG GCC ACC AAC CAG       98
Ser Leu Asn Ser Asn Ala Thr Ser His Leu Gly Leu Ala Thr Asn Gln
         15                  20                  25

TCA GAG CCT TGG TGC CTG TAT GTG TCC ATC CCA GAT GGC CTC TTC CTC      146
Ser Glu Pro Trp Cys Leu Tyr Val Ser Ile Pro Asp Gly Leu Phe Leu
     30                  35                  40

AGC CTA GGG CTG GTG AGT CTG GTG GAG AAT GTG CTG GTT GTG ATA GCC      194
Ser Leu Gly Leu Val Ser Leu Val Glu Asn Val Leu Val Val Ile Ala
 45                  50                  55                  60

ATC ACC AAA AAC CGC AAC CTG CAC TCG CCC ATG TAT TAC TTC ATC TGC      242
Ile Thr Lys Asn Arg Asn Leu His Ser Pro Met Tyr Tyr Phe Ile Cys
                 65                  70                  75
```

-continued

```
TGC CTG GCC CTG TCT GAC CTG ATG GTA AGT GTC AGC ATC GTG CTG GAG      290
Cys Leu Ala Leu Ser Asp Leu Met Val Ser Val Ser Ile Val Leu Glu
            80                  85                  90

ACT ACT ATC ATC CTG CTG CTG GAG GTG GGC ATC CTG GTG GCC AGA GTG      338
Thr Thr Ile Ile Leu Leu Leu Glu Val Gly Ile Leu Val Ala Arg Val
        95                  100                 105

GCT TTG GTG CAG CAG CTG GAC AAC CTC ATT GAC GTG CTC ATC TGT GGC      386
Ala Leu Val Gln Gln Leu Asp Asn Leu Ile Asp Val Leu Ile Cys Gly
    110                 115                 120

TCC ATG GTG TCC AGT CTC TGC TTC CTG GGC ATC ATT GCT ATA GAC CGC      434
Ser Met Val Ser Ser Leu Cys Phe Leu Gly Ile Ile Ala Ile Asp Arg
125                 130                 135                 140

TAC ATC TCC ATC TTC TAT GCG CTG CGT TAT CAC AGC ATC GTG ACG CTG      482
Tyr Ile Ser Ile Phe Tyr Ala Leu Arg Tyr His Ser Ile Val Thr Leu
                145                 150                 155

CCC AGA GCA CGA CGG GCT GTC GTG GGC ATC TGG ATG GTC AGC ATC GTC      530
Pro Arg Ala Arg Arg Ala Val Val Gly Ile Trp Met Val Ser Ile Val
            160                 165                 170

TCC AGC ACC CTC TTT ATC ACC TAC TAC AAG CAC ACA GCC GTT CTG CTC      578
Ser Ser Thr Leu Phe Ile Thr Tyr Tyr Lys His Thr Ala Val Leu Leu
        175                 180                 185

TGC CTC GTC ACT TTC TTT CTA GCC ATG CTG GCA CTC ATG GCG ATT CTG      626
Cys Leu Val Thr Phe Phe Leu Ala Met Leu Ala Leu Met Ala Ile Leu
    190                 195                 200

TAT GCC CAC ATG TTC ACG AGA GCG TGC CAG CAC GTC CAG GGC ATT GCC      674
Tyr Ala His Met Phe Thr Arg Ala Cys Gln His Val Gln Gly Ile Ala
205                 210                 215                 220

CAG CTC CAC AAA AGG CGG CGG TCC ATC CGC CAA GGC TTC TGC CTC AAG      722
Gln Leu His Lys Arg Arg Arg Ser Ile Arg Gln Gly Phe Cys Leu Lys
                225                 230                 235

GGT GCT GCC ACC CTT ACT ATC CTT CTG GGG ATT TTC TTC CTG TGC TGG      770
Gly Ala Ala Thr Leu Thr Ile Leu Leu Gly Ile Phe Phe Leu Cys Trp
            240                 245                 250

GGC CCC TTC TTC CTG CAT CTC TTG CTC ATC GTC CTC TGC CCT CAG CAC      818
Gly Pro Phe Phe Leu His Leu Leu Leu Ile Val Leu Cys Pro Gln His
        255                 260                 265

CCC ACC TGC AGC TGC ATC TTC AAG AAC TTC AAC CTC TTC CTC CTC CTC      866
Pro Thr Cys Ser Cys Ile Phe Lys Asn Phe Asn Leu Phe Leu Leu Leu
    270                 275                 280

ATC GTC CTC AGC TCC ACT GTT GAC CCC CTC ATC TAT GCT TTC CGC AGC      914
Ile Val Leu Ser Ser Thr Val Asp Pro Leu Ile Tyr Ala Phe Arg Ser
285                 290                 295                 300

CAG GAG CTC CGC ATG ACA CTC AAG GAG GTG CTG CTG TGC TCC TGG          959
Gln Glu Leu Arg Met Thr Leu Lys Glu Val Leu Leu Cys Ser Trp
                305                 310                 315

TGATCAGAGG GCGCTGGGCA GAGGGTGACA GTGATATCCA GTGGCCTGCA TCTGTGAGAC   1019

CACAGGTACT CATCCCTTCC TGATCTCCAT TTGTCTAAGG GTCGACAGGA TGAGCTTTAA   1079

AATAGAAACC CAGAGTGCCT GGGGCCAGGA GAAAGGGTAA CTGTGACTGC AGGGCTCACC   1139

CAGGGCAGCT ACGGGAAGTG GAGGAGACAG GGATGGGAAC TCTAGCCCTG AGCAAGGGTC   1199

AGACCACAGG CTCCTGAAGA GCTTCACCTC TCCCCACCTA CAGGCAACTC CTGCTCAAGC   1259

C                                                                   1260
```

(2) INFORMATION FOR SEQ ID NO: 4:

(i) SEQUENCE CHARACTERISTICS:
(A) LENGTH: 315 amino acids
(B) TYPE: amino acid

-continued (D) TOPOLOGY: linear (ii) MOLECULE TYPE: protein (xi) SEQUENCE DESCRIPTION: SEQ ID NO: 4:

```
Met Ser Thr Gln Glu Pro Gln Lys Ser Leu Leu Gly Ser Leu Asn Ser
  1               5                  10                  15

Asn Ala Thr Ser His Leu Gly Leu Ala Thr Asn Gln Ser Glu Pro Trp
             20                  25                  30

Cys Leu Tyr Val Ser Ile Pro Asp Gly Leu Phe Leu Ser Leu Gly Leu
         35                  40                  45

Val Ser Leu Val Glu Asn Val Leu Val Val Ile Ala Ile Thr Lys Asn
     50                  55                  60

Arg Asn Leu His Ser Pro Met Tyr Tyr Phe Ile Cys Cys Leu Ala Leu
 65                  70                  75                  80

Ser Asp Leu Met Val Ser Val Ser Ile Val Leu Glu Thr Thr Ile Ile
                 85                  90                  95

Leu Leu Leu Glu Val Gly Ile Leu Val Ala Arg Val Ala Leu Val Gln
            100                 105                 110

Gln Leu Asp Asn Leu Ile Asp Val Leu Ile Cys Gly Ser Met Val Ser
        115                 120                 125

Ser Leu Cys Phe Leu Gly Ile Ile Ala Ile Asp Arg Tyr Ile Ser Ile
    130                 135                 140

Phe Tyr Ala Leu Arg Tyr His Ser Ile Val Thr Leu Pro Arg Ala Arg
145                 150                 155                 160

Arg Ala Val Val Gly Ile Trp Met Val Ser Ile Val Ser Ser Thr Leu
                165                 170                 175

Phe Ile Thr Tyr Tyr Lys His Thr Ala Val Leu Leu Cys Leu Val Thr
            180                 185                 190

Phe Phe Leu Ala Met Leu Ala Leu Met Ala Ile Leu Tyr Ala His Met
        195                 200                 205

Phe Thr Arg Ala Cys Gln His Val Gln Gly Ile Ala Gln Leu His Lys
    210                 215                 220

Arg Arg Arg Ser Ile Arg Gln Gly Phe Cys Leu Lys Gly Ala Ala Thr
225                 230                 235                 240

Leu Thr Ile Leu Leu Gly Ile Phe Phe Leu Cys Trp Gly Pro Phe Phe
                245                 250                 255

Leu His Leu Leu Leu Ile Val Leu Cys Pro Gln His Pro Thr Cys Ser
            260                 265                 270

Cys Ile Phe Lys Asn Phe Asn Leu Phe Leu Leu Leu Ile Val Leu Ser
        275                 280                 285

Ser Thr Val Asp Pro Leu Ile Tyr Ala Phe Arg Ser Gln Glu Leu Arg
    290                 295                 300

Met Thr Leu Lys Glu Val Leu Leu Cys Ser Trp
305                 310                 315
```

(2) INFORMATION FOR SEQ ID NO: 5:

(i) SEQUENCE CHARACTERISTICS:
(A) LENGTH: 1633 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: 5'UTR -continued

```
         (B) LOCATION: 1..461

    (ix) FEATURE:
         (A) NAME/KEY: CDS
         (B) LOCATION: 462..1415

    (ix) FEATURE:
         (A) NAME/KEY: 3'UTR
         (B) LOCATION: 1416..1633

    (xi) SEQUENCE DESCRIPTION: SEQ ID NO: 5:

CCCGCATGTG GCCGCCCTCA ATGGAGGGCT CTGAGAACGA CTTTTAAAAC GCAGAGAAAA     60

AGCTCCATTC TTCCCAGACC TCAGCGCAGC CCTGGCCCAG GAAGGGAGGA GACAGAGGCC    120

AGGACGGTCC AGAGGTGTCG AAATGTCCTG GGAACCTGAG CAGCAGCCAC CAGGGAAGAG    180

GCAGGGAGGG AGCTGAGGAC CAGGCTTGGT TGTGAGAATC CCTGAGCCCA GGCGGTTGAT    240

GCCAGGAGGT GTCTGGACTG GCTGGGCCAT GCCTGGGCTG ACCTGTCCAG CCAGGGAGAG    300

GGTGTGAGGG CAGATCTGGG GGTGCCCAGA TGGAAGGAGG CAGGCATGGG GACACCCAAG    360

GCCCCCTGGC AGCACCATGA ACTAAGCAGG ACACCTGGAG GGGAAGAACT GTGGGGACCT    420

GGAGGCCTCC AACGACTCCT TCCTGCTTCC TGGACAGGAC T ATG GCT GTG CAG        473
                                              Met Ala Val Gln
                                                1

GGA TCC CAG AGA AGA CTT CTG GGC TCC CTC AAC TCC ACC CCC ACA GCC      521
Gly Ser Gln Arg Arg Leu Leu Gly Ser Leu Asn Ser Thr Pro Thr Ala
  5                  10                  15                  20

ATC CCC CAG CTG GGG CTG GCT GCC AAC CAG ACA GGA GCC CGG TGC CTG      569
Ile Pro Gln Leu Gly Leu Ala Ala Asn Gln Thr Gly Ala Arg Cys Leu
                 25                  30                  35

GAG GTG TCC ATC TCT GAC GGG CTC TTC CTC AGC CTG GGG CTG GTG AGC      617
Glu Val Ser Ile Ser Asp Gly Leu Phe Leu Ser Leu Gly Leu Val Ser
             40                  45                  50

TTG GTG GAG AAC GCG CTG GTG GTG GCC ACC ATC GCC AAG AAC CGG AAC      665
Leu Val Glu Asn Ala Leu Val Val Ala Thr Ile Ala Lys Asn Arg Asn
         55                  60                  65

CTG CAC TCA CCC ATG TAC TGC TTC ATC TGC TGC CTG GCC TTG TCG GAC      713
Leu His Ser Pro Met Tyr Cys Phe Ile Cys Cys Leu Ala Leu Ser Asp
     70                  75                  80

CTG CTG GTG AGC GGG ACG AAC GTG CTG GAG ACG GCC GTC ATC CTC CTG      761
Leu Leu Val Ser Gly Thr Asn Val Leu Glu Thr Ala Val Ile Leu Leu
 85                  90                  95                 100

CTG GAG GCC GGT GCA CTG GTG GCC CGG GCT GCG GTG CTG CAG CAG CTG      809
Leu Glu Ala Gly Ala Leu Val Ala Arg Ala Ala Val Leu Gln Gln Leu
                105                 110                 115

GAC AAT GTC ATT GAC GTG ATC ACC TGC AGC TCC ATG CTG TCC AGC CTC      857
Asp Asn Val Ile Asp Val Ile Thr Cys Ser Ser Met Leu Ser Ser Leu
            120                 125                 130

TGC TTC CTG GGC GCC ATC GCC GTG GAC CGC TAC ATC TCC ATC TTC TAC      905
Cys Phe Leu Gly Ala Ile Ala Val Asp Arg Tyr Ile Ser Ile Phe Tyr
        135                 140                 145

GCA CTG CGC TAC CAC AGC ATC GTG ACC CTG CCG CGG GCG CCG CGA GCC      953
Ala Leu Arg Tyr His Ser Ile Val Thr Leu Pro Arg Ala Pro Arg Ala
    150                 155                 160

GTT GCG GCC ATC TGG GTG GCC AGT GTC GTC TTC AGC ACG CTC TTC ATC     1001
Val Ala Ala Ile Trp Val Ala Ser Val Val Phe Ser Thr Leu Phe Ile
165                 170                 175                 180

GGC TAC TAC GAC CAC GTG GCC GTC CTG CTG TGC CTC GTG GTC TTC TTC     1049
Gly Tyr Tyr Asp His Val Ala Val Leu Leu Cys Leu Val Val Phe Phe
                185                 190                 195

CTG GCT ATG CTG GTG CTC ATG GCC GTG CTG GAC GTC CAC ATG CTG GCC     1097
```

-continued

```
Leu Ala Met Leu Val Leu Met Ala Val Leu Asp Val His Met Leu Ala
            200                 205                 210

CGG GCC TGC CAG CAC GCC CAG GGC ATC GCC CGG CTC CAC AAG AGG CAG     1145
Arg Ala Cys Gln His Ala Gln Gly Ile Ala Arg Leu His Lys Arg Gln
        215                 220                 225

CGC CCG GTC CAC CAG GGC TTT GGC CTT AAA GGC GCT GTC ACC CTC ACC     1193
Arg Pro Val His Gln Gly Phe Gly Leu Lys Gly Ala Val Thr Leu Thr
    230                 235                 240

ATC CTG CTG GGC ATT TTC TTC CTC TGC TGG GGC CCC TTC TTC CTG CAT     1241
Ile Leu Leu Gly Ile Phe Phe Leu Cys Trp Gly Pro Phe Phe Leu His
245                 250                 255                 260

CTC ACA CTC ATC GTC CTC TGC CCC GAG CAC CCC ACG TGC GGC TGC ATC     1289
Leu Thr Leu Ile Val Leu Cys Pro Glu His Pro Thr Cys Gly Cys Ile
                265                 270                 275

TTC AAG AAC TTC AAC CTC TTT CTC GCC CTC ATC ATC TGC AAT GCC ATC     1337
Phe Lys Asn Phe Asn Leu Phe Leu Ala Leu Ile Ile Cys Asn Ala Ile
            280                 285                 290

ATC GAC CCC CTC ATC TAC GCC TTC CAC AGC CAG GAG CTC CGC AGG ACG     1385
Ile Asp Pro Leu Ile Tyr Ala Phe His Ser Gln Glu Leu Arg Arg Thr
        295                 300                 305

CTC AAG GAG GTG CTG ACA TGC TCC TGG TGA GCGCGGTGCA CGCGCTTTAA       1435
Leu Lys Glu Val Leu Thr Cys Ser Trp  *
    310                 315

GTGTGCTGGG CAGAGGGAGG TGGTGATATT GTGGTCTGGT TCCTGTGTGA TGACCCTGGG1495

TTCCTTACCT CCCTGGTCCC CGTTTGTCAA AGAGGATGGA CTAAATGATC TCTGAAAG1555

TTGAAGCGCG GACCCTTCTG GGCAGGGAGG GGTCCTGCAA AACTCCAGGC AGGACTT1615

ACCAGCAGTC GTCGTGGGAA C                                            1633
```

(2) INFORMATION FOR SEQ ID NO: 6:

(i) SEQUENCE CHARACTERISTICS:
(A) LENGTH: 317 amino acids
(B) TYPE: amino acid
(D) TOPOLOGY: linear (ii) MOLECULE TYPE: protein (xi) SEQUENCE DESCRIPTION: SEQ ID NO: 6:

```
Met Ala Val Gln Gly Ser Gln Arg Arg Leu Leu Gly Ser Leu Asn Ser
  1               5                  10                  15

Thr Pro Thr Ala Ile Pro Gln Leu Gly Leu Ala Ala Asn Gln Thr Gly
             20                  25                  30

Ala Arg Cys Leu Glu Val Ser Ile Ser Asp Gly Leu Phe Leu Ser Leu
         35                  40                  45

Gly Leu Val Ser Leu Val Glu Asn Ala Leu Val Val Ala Thr Ile Ala
     50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Thr Asn Val Leu Glu Thr Ala
                 85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
```

-continued

```
145                 150                 155                 160

Ala Pro Arg Ala Val Ala Ala Ile Trp Val Ala Ser Val Val Phe Ser
                165                 170                 175

Thr Leu Phe Ile Gly Tyr Tyr Asp His Val Ala Val Leu Leu Cys Leu
            180                 185                 190

Val Val Phe Phe Leu Ala Met Leu Val Leu Met Ala Val Leu Asp Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Trp
305                 310                 315
```

(2) INFORMATION FOR SEQ ID NO: 7:

(i) SEQUENCE CHARACTERISTICS:
(A) LENGTH: 2012 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: 5'UTR
(B) LOCATION: 1..693

(ix) FEATURE:
(A) NAME/KEY: CDS
(B) LOCATION: 694..1587

(ix) FEATURE:
(A) NAME/KEY: 3'UTR
(B) LOCATION: 1588..2012

(xi) SEQUENCE DESCRIPTION: SEQ ID NO: 7:

```
ACAACACTTT ATATATATTT TTATAAATGT AAGGGGTACA AAGGTGCCAT TTTGTTACAT     60

GGATATACCG TGTAGTGGTG AAGCCTGGGC TTTTAGTGTA TCTGTCATCA GAATAACATA    120

CGTGTTACCC ATAGGAATTT CTCATCACCC GCCCCCTCCA CCCTTCGAGT CTCCAATGTC    180

CATTCCACAC TCTATATCCA CGTGTATGCA TATAGCTCCA CATATAAGTG AGAACATGTA    240

GTATTTGACT TCCTCTTTCT GAGTTATTTC ACTTTGATAA TGGCCTCCAC TTCCATCCAT    300

GTTGCTGCAA AAGACATGAC CTTATTCTTT TTGATAGCTG GGGAGTACTC CATTGTGTAT    360

ATGTACCACA TTTCTTTATC CATTCACCCA TTGAGAACAC TTAGTTGATT CCATATCTTT    420

GCTATTGTCA CTAGTGCTGC AATAAACATA CATGTGCAGG CTCCTTCTAA TATACTGATT    480

TATATTTTAT GGAGAGAGAT AGAGTTCTTA GCGAGTGTGC TGTTTATTTC TAGTGTACTT    540

GCAACTAATA TTCTGTATAC TCCCTTTAGG TGATTGGAGA TTTAACTTAG ATCTCCAGCA    600

AGTGCTACAA GAAGAAAAGA TCCTGAAGAA TCAATCAAGT TTCCGTGAAG TCAAGTCCAA    660
```

-continued

```
GTAACATCCC CGCCTTAACC ACAAGCAGGA GAA ATG AAG CAC ATT ATC AAC TCG      714
                                     Met Lys His Ile Ile Asn Ser
                                      1               5

TAT GAA AAC ATC AAC AAC ACA GCA AGA AAT AAT TCC GAC TGT CCT CGT      762
Tyr Glu Asn Ile Asn Asn Thr Ala Arg Asn Asn Ser Asp Cys Pro Arg
        10                  15                  20

TGT GTT TTG CCG GAG GAG ATA TTT TTC ACA ATT TCC ATT GTT GGA GTT      810
Cys Val Leu Pro Glu Glu Ile Phe Phe Thr Ile Ser Ile Val Gly Val
    25                  30                  35

TTG GAG AAT CTG ATC GTC CTG CTG GCT GTG TTC AAG AAT AAG AAT CTC      858
Leu Glu Asn Leu Ile Val Leu Leu Ala Val Phe Lys Asn Lys Asn Leu
 40                  45                  50                  55

CAG GCA CCC ATG TAC TTT TTC ATC TGT AGC TTG GCC ATA TCT GAT ATG      906
Gln Ala Pro Met Tyr Phe Phe Ile Cys Ser Leu Ala Ile Ser Asp Met
                60                  65                  70

CTG GGC AGC CTA TAT AAG ATC TTG GAA AAT ATC CTG ATC ATA TTG AGA      954
Leu Gly Ser Leu Tyr Lys Ile Leu Glu Asn Ile Leu Ile Ile Leu Arg
            75                  80                  85

AAC ATG GGC ATA CTC AAG CCA CGT GGC AGT TTT GAA ACC ACA GCC CAT     1002
Asn Met Gly Ile Leu Lys Pro Arg Gly Ser Phe Glu Thr Thr Ala His
        90                  95                 100

GAC ATC ATC GAC TCC CTG TTT CTG CTC TCC CGT CTT GGC TCC ATC TTC     1050
Asp Ile Ile Asp Ser Leu Phe Leu Leu Ser Arg Leu Gly Ser Ile Phe
    105                 110                 115

GAC CTG CTC GTG ATT GCT GCG GAC CGC TAC ATC ACC ATC TTC CAC GCA     1098
Asp Leu Leu Val Ile Ala Ala Asp Arg Tyr Ile Thr Ile Phe His Ala
120                 125                 130                 135

CTG CGG TAC CAC AGC ATC GTG ACC ATG CGC CGC ACT GTG GTG GTG CTT     1146
Leu Arg Tyr His Ser Ile Val Thr Met Arg Arg Thr Val Val Val Leu
                140                 145                 150

ACG GTC ATC TGG ACG TTC TGC ACG GGG ACT GGC ATC ACC ATG GTG ATC     1194
Thr Val Ile Trp Thr Phe Cys Thr Gly Thr Gly Ile Thr Met Val Ile
            155                 160                 165

TTC TCC CAT CAT GTG CCC CAC GTG ATC ACC TTC ACG TCG CTG TTC CCG     1242
Phe Ser His His Val Pro His Val Ile Thr Phe Thr Ser Leu Phe Pro
        170                 175                 180

CTG ATG CTG GTC TTC ATC CTG TGC CTC TAT GTG CAC ATG TTC CTG CTG     1290
Leu Met Leu Val Phe Ile Leu Cys Leu Tyr Val His Met Phe Leu Leu
    185                 190                 195

GCT CGA TGG CAC ACC AGG AAG ATC TCC ACC CTC CCC AGA GCC AAC ATG     1338
Ala Arg Trp His Thr Arg Lys Ile Ser Thr Leu Pro Arg Ala Asn Met
200                 205                 210                 215

AAA GGG GCC ATG ACA CTG ACC ATC CTG CTC GGG GTC TTC ATC TTC TGC     1386
Lys Gly Ala Met Thr Leu Thr Ile Leu Leu Gly Val Phe Ile Phe Cys
                220                 225                 230

TGG GCC CCC TTT GTG CTT CAT GTC CTC TTG ATG ACA TTC TGC CCA AGT     1434
Trp Ala Pro Phe Val Leu His Val Leu Leu Met Thr Phe Cys Pro Ser
            235                 240                 245

AAC CCC TAC TGC GCC TGC TAC ATG TCT CTC TTC CAG GTG AAC GGC ATG     1482
Asn Pro Tyr Cys Ala Cys Tyr Met Ser Leu Phe Gln Val Asn Gly Met
        250                 255                 260

TTG ATC ATG TGC AAT GCC GTC ATT GAC CCC TTC ATA TAT GCC TTC CGG     1530
Leu Ile Met Cys Asn Ala Val Ile Asp Pro Phe Ile Tyr Ala Phe Arg
    265                 270                 275

AGC CCA GAG CTC AGG GAC GCA TTC AAA AAG ATG ATC TTC TGC AGC AGG     1578
Ser Pro Glu Leu Arg Asp Ala Phe Lys Lys Met Ile Phe Cys Ser Arg
280                 285                 290                 295

TAC TGG TAG AATGGCTGAT CCCTGGTTTT AGAATCCATG GGAATAACGT             1627
Tyr Trp  *
```

-continued

```
TGCCAAGTGC CAGAATAGTG TAACATTCCA ACAAATGCCA GTGCTCCTCA CTGGCCTTCC   1687

TTCCCTAATG GATGCAAGGA TGACCCACCA GCTAGTGTTT CTGAATACTA TGGCCAGGAA   1747

CAGTCTATTG TAGGGGCAAC TCTATTTGTG ACTGGACAGA TAAAACGTGT AGTAAAAGAA   1807

GGATAGAATA CAAAGTATTA GGTACAAAAG TAATTAGGTT TGCATTACTT ATGACAAATG   1867

CATTACTTTT GCACCAATCT AGTAAAACAG CAATAAAAAT TCAAGGGCTT TGGGCTAAGG   1927

CAAAGACTTG CTTTCCTGTG GACATTAACA AGCCAGTTCT GAGGCGGCCT TTCCAGGTGG   1987

AGGCCATTGC AGCCAATTTC AGAGT                                         2012
```

(2) INFORMATION FOR SEQ ID NO: 8:

(i) SEQUENCE CHARACTERISTICS:
(A) LENGTH: 297 amino acids
(B) TYPE: amino acid
(D) TOPOLOGY: linear (ii) MOLECULE TYPE: protein (xi) SEQUENCE DESCRIPTION: SEQ ID NO: 8:

```
Met Lys His Ile Ile Asn Ser Tyr Glu Asn Ile Asn Asn Thr Ala Arg
  1               5                  10                  15

Asn Asn Ser Asp Cys Pro Arg Cys Val Leu Pro Glu Glu Ile Phe Phe
             20                  25                  30

Thr Ile Ser Ile Val Gly Val Leu Glu Asn Leu Ile Val Leu Leu Ala
         35                  40                  45

Val Phe Lys Asn Lys Asn Leu Gln Ala Pro Met Tyr Phe Phe Ile Cys
     50                  55                  60

Ser Leu Ala Ile Ser Asp Met Leu Gly Ser Leu Tyr Lys Ile Leu Glu
 65                  70                  75                  80

Asn Ile Leu Ile Ile Leu Arg Asn Met Gly Ile Leu Lys Pro Arg Gly
                 85                  90                  95

Ser Phe Glu Thr Thr Ala His Asp Ile Ile Asp Ser Leu Phe Leu Leu
            100                 105                 110

Ser Arg Leu Gly Ser Ile Phe Asp Leu Leu Val Ile Ala Ala Asp Arg
        115                 120                 125

Tyr Ile Thr Ile Phe His Ala Leu Arg Tyr His Ser Ile Val Thr Met
    130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro His Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Trp His Thr Arg Lys Ile Ser
        195                 200                 205

Thr Leu Pro Arg Ala Asn Met Lys Gly Ala Met Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285
```

-continued

```
Lys Met Ile Phe Cys Ser Arg Tyr Trp
    290                 295


(2) INFORMATION FOR SEQ ID NO: 9:

     (i) SEQUENCE CHARACTERISTICS:
          (A) LENGTH: 1108 base pairs
          (B) TYPE: nucleic acid
          (C) STRANDEDNESS: single
          (D) TOPOLOGY: linear

    (ii) MOLECULE TYPE: cDNA to mRNA

    (ix) FEATURE:
          (A) NAME/KEY: 5'UTR
          (B) LOCATION: 1..132

    (ix) FEATURE:
          (A) NAME/KEY: CDS
          (B) LOCATION: 133..1026

    (ix) FEATURE:
          (A) NAME/KEY: 3'UTR
          (B) LOCATION: 1027..1106

    (xi) SEQUENCE DESCRIPTION: SEQ ID NO: 9:

GGGGCCAGAA AGTTCCTGCT TCAGAGCAGA AGATCTTCAG CAAGAACTAC AAAGAAGAAA      60

AGATTCTGGA GAATCAATCA AGTTTCCTGT CAAGTTCCAG TAACGTTTCT GTCTTAACTG     120

CACACAGGAA AG ATG AAA CAC ATT CTC AAT CTG TAT GAA AAC CTC AAC         168
              Met Lys His Ile Leu Asn Leu Tyr Glu Asn Leu Asn
                1               5                  10

AGT ACA GCA AGA AAT AAC TCA GAC TGT CCT GCT GTG ATT TTG CCA GAA       216
Ser Thr Ala Arg Asn Asn Ser Asp Cys Pro Ala Val Ile Leu Pro Glu
        15                  20                  25

GAG ATA TTT TTC ACA GTA TCC ATT GTT GGG GTT TTG GAG AAC CTG ATG       264
Glu Ile Phe Phe Thr Val Ser Ile Val Gly Val Leu Glu Asn Leu Met
     30                  35                  40

GTC CTT CTG GCT GTG GCC AAG AAT AAG ATG CTT CAG TCG CCC ATG TAC       312
Val Leu Leu Ala Val Ala Lys Asn Lys Met Leu Gln Ser Pro Met Tyr
 45                  50                  55                  60

TTT TTC ATC TGC AGC TTG GCT ATT TCC GAT ATG CTG GGG AGC ATG TAC       360
Phe Phe Ile Cys Ser Leu Ala Ile Ser Asp Met Leu Gly Ser Met Tyr
                 65                  70                  75

AAG ATT TTG GAA AAC GTT CTG ATC ATG TTC AAA AAC ATG GGT TAC CTC       408
Lys Ile Leu Glu Asn Val Leu Ile Met Phe Lys Asn Met Gly Tyr Leu
             80                  85                  90

GAG CCT CGA GGC AGT TTT GAA AGC ACA GCA GAT GAT GTG GTG GAC TCC       456
Glu Pro Arg Gly Ser Phe Glu Ser Thr Ala Asp Asp Val Val Asp Ser
        95                 100                 105

CTG TTC ATC CTC TCC CTT CTC GGC TCC ATC TGC AGC CTG TCT GTG ATT       504
Leu Phe Ile Leu Ser Leu Leu Gly Ser Ile Cys Ser Leu Ser Val Ile
    110                 115                 120

GCC GCT GAC CGC TAC ACT ACA ATC TTC CAC GCT CTG CAG TAC CAC CGC       552
Ala Ala Asp Arg Tyr Thr Thr Ile Phe His Ala Leu Gln Tyr His Arg
125                 130                 135                 140

ATC ATG ACC CCC GCA CCG TGC CCT CGT CAT CTG ACG GTC CTC TGG CGA       600
Ile Met Thr Pro Ala Pro Cys Pro Arg His Leu Thr Val Leu Trp Arg
                145                 150                 155

GGC TGC ACA GGC AGT GGC ATT ACC ATC GTG ACC TTC TCC CAT CAC GTC       648
Gly Cys Thr Gly Ser Gly Ile Thr Ile Val Thr Phe Ser His His Val
            160                 165                 170

CCC ACA GTG ATC GCC TTC ACA GCG CTG TTC CCG CTG ATG CTG GCC TTC       696
Pro Thr Val Ile Ala Phe Thr Ala Leu Phe Pro Leu Met Leu Ala Phe
```

-continued

```
        175                 180                 185

ATC CTG TGC CTC TAC GTG CAC ATG TTC CTG CTG GCC CGC TCC CAC ACC      744
Ile Leu Cys Leu Tyr Val His Met Phe Leu Leu Ala Arg Ser His Thr
    190                 195                 200

AGG AGG ACC CCC TCC CTT CCC AAA GCC AAC ATG AGA GGG GCC GTC ACA      792
Arg Arg Thr Pro Ser Leu Pro Lys Ala Asn Met Arg Gly Ala Val Thr
205                 210                 215                 220

CTG ACT GTC CTG CTC GGG GTC TTC ATT TTC TGT TGG GCA CCC TTT GTC      840
Leu Thr Val Leu Leu Gly Val Phe Ile Phe Cys Trp Ala Pro Phe Val
                225                 230                 235

CTT CAT GTC CTC TTG ATG ACA TTC TGC CCA GCT GAC CCC TAC TGT GCC      888
Leu His Val Leu Leu Met Thr Phe Cys Pro Ala Asp Pro Tyr Cys Ala
            240                 245                 250

TGC TAC ATG TCC CTC TTC CAG GTG AAT GGT GTG TTG ATC ATG TGT AAT      936
Cys Tyr Met Ser Leu Phe Gln Val Asn Gly Val Leu Ile Met Cys Asn
        255                 260                 265

GCC ATC ATC GAC CCC TTC ATA TAT GCC TTT CGG AGC CCA GAG CTC AGG      984
Ala Ile Ile Asp Pro Phe Ile Tyr Ala Phe Arg Ser Pro Glu Leu Arg
    270                 275                 280

GTC GCA TTC AAA AAG ATG GTT ATC TGC AAC TGT TAC CAG TAG             1026
Val Ala Phe Lys Lys Met Val Ile Cys Asn Cys Tyr Gln  *
285                 290                 295

AATGATTGGT CCCTGATTTT AGGAGCCACA GGGATATACT GTCAGGGACA GAGTAGCGTG   1086

ACAGACCAAC AACACTAGGA CT                                            1108
```

(2) INFORMATION FOR SEQ ID NO: 10:

(i) SEQUENCE CHARACTERISTICS:
(A) LENGTH: 297 amino acids
(B) TYPE: amino acid
(D) TOPOLOGY: linear (ii) MOLECULE TYPE: protein (xi) SEQUENCE DESCRIPTION: SEQ ID NO: 10:

```
Met Lys His Ile Leu Asn Leu Tyr Glu Asn Leu Asn Ser Thr Ala Arg
  1               5                  10                  15

Asn Asn Ser Asp Cys Pro Ala Val Ile Leu Pro Glu Glu Ile Phe Phe
             20                  25                  30

Thr Val Ser Ile Val Gly Val Leu Glu Asn Leu Met Val Leu Leu Ala
         35                  40                  45

Val Ala Lys Asn Lys Met Leu Gln Ser Pro Met Tyr Phe Phe Ile Cys
     50                  55                  60

Ser Leu Ala Ile Ser Asp Met Leu Gly Ser Met Tyr Lys Ile Leu Glu
 65                  70                  75                  80

Asn Val Leu Ile Met Phe Lys Asn Met Gly Tyr Leu Glu Pro Arg Gly
                 85                  90                  95

Ser Phe Glu Ser Thr Ala Asp Asp Val Val Asp Ser Leu Phe Ile Leu
            100                 105                 110

Ser Leu Leu Gly Ser Ile Cys Ser Leu Ser Val Ile Ala Ala Asp Arg
        115                 120                 125

Tyr Thr Thr Ile Phe His Ala Leu Gln Tyr His Arg Ile Met Thr Pro
    130                 135                 140

Ala Pro Cys Pro Arg His Leu Thr Val Leu Trp Arg Gly Cys Thr Gly
145                 150                 155                 160

Ser Gly Ile Thr Ile Val Thr Phe Ser His His Val Pro Thr Val Ile
                165                 170                 175
```

-continued

```
Ala Phe Thr Ala Leu Phe Pro Leu Met Leu Ala Phe Ile Leu Cys Leu
            180                 185                 190

Tyr Val His Met Phe Leu Leu Ala Arg Ser His Thr Arg Arg Thr Pro
        195                 200                 205

Ser Leu Pro Lys Ala Asn Met Arg Gly Ala Val Thr Leu Thr Val Leu
    210                 215                 220

Leu Gly Val Phe Ile Phe Cys Trp Ala Pro Phe Val Leu His Val Leu
225                 230                 235                 240

Leu Met Thr Phe Cys Pro Ala Asp Pro Tyr Cys Ala Cys Tyr Met Ser
                245                 250                 255

Leu Phe Gln Val Asn Gly Val Leu Ile Met Cys Asn Ala Ile Ile Asp
            260                 265                 270

Pro Phe Ile Tyr Ala Phe Arg Ser Pro Glu Leu Arg Val Ala Phe Lys
        275                 280                 285

Lys Met Val Ile Cys Asn Cys Tyr Gln
    290                 295
```

(2) INFORMATION FOR SEQ ID NO: 11:

(i) SEQUENCE CHARACTERISTICS:
(A) LENGTH: 1338 base pairs
(B) TYPE: nucleic acid
(C) STRANDEDNESS: single
(D) TOPOLOGY: linear (ii) MOLECULE TYPE: cDNA to mRNA (ix) FEATURE:
(A) NAME/KEY: 5'UTR
(B) LOCATION: 1..297

(ix) FEATURE:
(A) NAME/KEY: CDS
(B) LOCATION: 298..1269

(ix) FEATURE:
(A) NAME/KEY: 3'UTR
(B) LOCATION: 1270..1338

(xi) SEQUENCE DESCRIPTION: SEQ ID NO: 11:

```
GGCTGTAACT GTAGCAACCG GTGTTGGGTG GGGATGAGAA GAGACCAGAG AGAGAGAGGG     60

TCAGAGCGAC AGGGGATGAG ACAGGCTGGT CAGAGTCTGC ACTGATTGTT GGAGACGCAA    120

AGGAAAGTTT TTTCTATGTC TCCAACCTCC CCCTCCTCCC CCGTTTCTCT CTGGAGAAAC    180

TAAAATGTAG ACTGGACAGC ATCCACAAGA GAAGCACCTA GAAGAAGATT TTTTTTTCCC    240

AGCAGCTTGC TCAGGACCCT GCAGGAGCTG CAGCCGGAAC TGGTCCCGCC GATAACC       297

ATG AAC TCT TCC TGC TGC CCG TCC TCC TCT TAT CCG ACG CTG CCT AAC      345
Met Asn Ser Ser Cys Cys Pro Ser Ser Ser Tyr Pro Thr Leu Pro Asn
  1               5                  10                  15

CTC TCC CAG CAC CCT GCA GCC CCC TCT GCC AGC AAC CGG AGT GGC AGT      393
Leu Ser Gln His Pro Ala Ala Pro Ser Ala Ser Asn Arg Ser Gly Ser
             20                  25                  30

GGG TTC TGC GAG CAG GTT TTC ATC AAG CCA GAG GTC TTC CTG GCA CTG      441
Gly Phe Cys Glu Gln Val Phe Ile Lys Pro Glu Val Phe Leu Ala Leu
         35                  40                  45

GGC ATC GTC AGT CTG ATG GAA AAC ATC CTG GTG ATC CTG GCT GTG GTG      489
Gly Ile Val Ser Leu Met Glu Asn Ile Leu Val Ile Leu Ala Val Val
     50                  55                  60

AGG AAC GGC AAC CTG CAC TCC CCC ATG TAC TTC TTC CTG CTG AGC CTG      537
Arg Asn Gly Asn Leu His Ser Pro Met Tyr Phe Phe Leu Leu Ser Leu
 65                  70                  75                  80
```

-continued

```
CTG CAG GCC GAC CTG CTG GTG AGC CTG TCC AAC TCC CTG GAG ACC ATC       585
Leu Gln Ala Asp Leu Leu Val Ser Leu Ser Asn Ser Leu Glu Thr Ile
                 85                  90                  95

ATG ATC GTG GTT ATC AAC AGC GAC TCC CTG ACC TTG GAG GAC CAA TTC       633
Met Ile Val Val Ile Asn Ser Asp Ser Leu Thr Leu Glu Asp Gln Phe
            100                 105                 110

ATC CAG CAC ATG GAC AAC ATC TTC GAC TCT ATG ATC TGC ATC TCC CTG       681
Ile Gln His Met Asp Asn Ile Phe Asp Ser Met Ile Cys Ile Ser Leu
        115                 120                 125

GTG GCC TCC ATC TGC AAC CTC CTG GCC ATC GCC GTG GAC AGG TAC GTC       729
Val Ala Ser Ile Cys Asn Leu Leu Ala Ile Ala Val Asp Arg Tyr Val
    130                 135                 140

ACC ATC TTC TAT GCC CTC CGT TAC CAC AGC ATC ATG ACG GTT AGG AAA       777
Thr Ile Phe Tyr Ala Leu Arg Tyr His Ser Ile Met Thr Val Arg Lys
145                 150                 155                 160

GCC CTC TCC TTG ATC GTG GCC ATC TGG GTC TGC TGT GGC ATC TGC GGC       825
Ala Leu Ser Leu Ile Val Ala Ile Trp Val Cys Cys Gly Ile Cys Gly
                165                 170                 175

GTG ATG TTC ATC GTC TAC TCC GAG AGC AAG ATG GTC ATC GTG TGC CTC       873
Val Met Phe Ile Val Tyr Ser Glu Ser Lys Met Val Ile Val Cys Leu
            180                 185                 190

ATC ACC ATG TTC TTC GCC ATG GTG CTC CTC ATG GGC ACC CTG TAC ATC       921
Ile Thr Met Phe Phe Ala Met Val Leu Leu Met Gly Thr Leu Tyr Ile
        195                 200                 205

CAC ATG TTC CTC TTC GCC AGG CTG CAC GTC CAG CGC ATC GCG GCA CTG       969
His Met Phe Leu Phe Ala Arg Leu His Val Gln Arg Ile Ala Ala Leu
    210                 215                 220

CCA CCT GCT GAC GGG CTA GCC CCG CAG CAG CAC TCG TGC ATG AAG GGG      1017
Pro Pro Ala Asp Gly Leu Ala Pro Gln Gln His Ser Cys Met Lys Gly
225                 230                 235                 240

GCC GTC ACC ATC ACC ATC CTG CTG GGG GTT TTC ATC TTC TGC TGG GCG      1065
Ala Val Thr Ile Thr Ile Leu Leu Gly Val Phe Ile Phe Cys Trp Ala
                245                 250                 255

CCT TTC TTC CTC CAC CTG GTC CTC ATC ATC ACC TGC CCC ACC AAC CCC      1113
Pro Phe Phe Leu His Leu Val Leu Ile Ile Thr Cys Pro Thr Asn Pro
            260                 265                 270

TAC TGC ATC TGC TAC ACG GCG CAC TTC AAC ACC TAC CTG GTT CTC ATC      1161
Tyr Cys Ile Cys Tyr Thr Ala His Phe Asn Thr Tyr Leu Val Leu Ile
        275                 280                 285

ATG TGC AAC TCT GTC ATC GAC CCC CTC ATC TAC GCC TTC CGC AGC CTG      1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG      1257
Glu Leu Arg Asn Thr Phe Lys Glu Ile Leu Cys Gly Cys Asn Gly Met
305                 310                 315                 320

AAC GTG GGC TAG GAACCCCCGA GGAGGTGTTC CACGGCTAGC CAAGAGAGAA          1309
Asn Val Gly  *

AAGCAATGCT CAGGTGAGAC ACAGAAGGG                                      1338
```

(2) INFORMATION FOR SEQ ID NO: 12:

(i) SEQUENCE CHARACTERISTICS:
(A) LENGTH: 323 amino acids
(B) TYPE: amino acid
(D) TOPOLOGY: linear (ii) MOLECULE TYPE: protein (xi) SEQUENCE DESCRIPTION: SEQ ID NO: 12:

```
Met Asn Ser Ser Cys Cys Pro Ser Ser Ser Tyr Pro Thr Leu Pro Asn
  1               5                  10                  15
```

-continued

```
Leu Ser Gln His Pro Ala Ala Pro Ser Ala Ser Asn Arg Ser Gly Ser
            20                  25                  30

Gly Phe Cys Glu Gln Val Phe Ile Lys Pro Glu Val Phe Leu Ala Leu
        35                  40                  45

Gly Ile Val Ser Leu Met Glu Asn Ile Leu Val Ile Leu Ala Val Val
    50                  55                  60

Arg Asn Gly Asn Leu His Ser Pro Met Tyr Phe Phe Leu Leu Ser Leu
65                  70                  75                  80

Leu Gln Ala Asp Leu Leu Val Ser Leu Ser Asn Ser Leu Glu Thr Ile
                85                  90                  95

Met Ile Val Val Ile Asn Ser Asp Ser Leu Thr Leu Glu Asp Gln Phe
            100                 105                 110

Ile Gln His Met Asp Asn Ile Phe Asp Ser Met Ile Cys Ile Ser Leu
        115                 120                 125

Val Ala Ser Ile Cys Asn Leu Leu Ala Ile Ala Val Asp Arg Tyr Val
    130                 135                 140

Thr Ile Phe Tyr Ala Leu Arg Tyr His Ser Ile Met Thr Val Arg Lys
145                 150                 155                 160

Ala Leu Ser Leu Ile Val Ala Ile Trp Val Cys Cys Gly Ile Cys Gly
                165                 170                 175

Val Met Phe Ile Val Tyr Ser Glu Ser Lys Met Val Ile Val Cys Leu
            180                 185                 190

Ile Thr Met Phe Phe Ala Met Val Leu Leu Met Gly Thr Leu Tyr Ile
        195                 200                 205

His Met Phe Leu Phe Ala Arg Leu His Val Gln Arg Ile Ala Ala Leu
    210                 215                 220

Pro Pro Ala Asp Gly Leu Ala Pro Gln Gln His Ser Cys Met Lys Gly
225                 230                 235                 240

Ala Val Thr Ile Thr Ile Leu Leu Gly Val Phe Ile Phe Cys Trp Ala
                245                 250                 255

Pro Phe Phe Leu His Leu Val Leu Ile Ile Thr Cys Pro Thr Asn Pro
            260                 265                 270

Tyr Cys Ile Cys Tyr Thr Ala His Phe Asn Thr Tyr Leu Val Leu Ile
        275                 280                 285

Met Cys Asn Ser Val Ile Asp Pro Leu Ile Tyr Ala Phe Arg Ser Leu
    290                 295                 300

Glu Leu Arg Asn Thr Phe Lys Glu Ile Leu Cys Gly Cys Asn Gly Met
305                 310                 315                 320

Asn Val Gly
```

(2) INFORMATION FOR SEQ ID NO: 13:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_feature
(B) LOCATION: 1..30
(D) OTHER INFORMATION: /function = "Degenerate oligonucleotide primer (sense)"

(xi) SEQUENCE DESCRIPTION: SEQ ID NO: 13:

-continued

```
GAGTCGACCR CCCATGTAYT DYTTCATCTG                                       30


(2) INFORMATION FOR SEQ ID NO: 14:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: misc_feature
          (B) LOCATION: 1..30
          (D) OTHER INFORMATION: /function = "Degenerate
               oligonucleotide primer (sense)"

    (xi) SEQUENCE DESCRIPTION: SEQ ID NO: 14:

CAGAATTCGG AARGCRTAKA TGARGGGGTC                                       30


(2) INFORMATION FOR SEQ ID NO: 15:

     (i) SEQUENCE CHARACTERISTICS:
          (A) LENGTH: 1671 base pairs
          (B) TYPE: nucleic acid
          (C) STRANDEDNESS: single
          (D) TOPOLOGY: linear

    (ii) MOLECULE TYPE: cDNA to mRNA

    (ix) FEATURE:
          (A) NAME/KEY: 5'UTR
          (B) LOCATION: 1..393

    (ix) FEATURE:
          (A) NAME/KEY: CDS
          (B) LOCATION: 394..1389

    (ix) FEATURE:
          (A) NAME/KEY: 3'UTR
          (B) LOCATION: 1390..1671

    (xi) SEQUENCE DESCRIPTION: SEQ ID NO: 15:

AGCTTCCGAG AGGCAGCCGA TGTGAGCATG TGCGCACAGA TTCGTCTCCC AATGGCATGG      60

CAGCTTCAAG GAAAATTATT TTGAACAGAC TTGAATGCAT AAGATTAAAG TTAAAGCAGA     120

AGTGAGAACA AGAAAGCAAA GAGCAGACTC TTTCAACTGA GAATGAATAT TTTGAAGCCC     180

AAGATTTTAA CGTGATGATG ATTAGAGTCG TACCTAAAAG AGACTAAAAA CTCCATGTCA     240

AGCTCTGGAC TTGTGACATT TACTCACAGC AGGCATGGCA ATTTTAGCCT CACAACTTTC     300

AGACAGATAA AGACTTGGAG GAAATAACTG AGACGACTCC CTGACCCAGG AGGTTAAATC     360

AATTCAGGGG GACACTGGAA TTCTCCTGCC AGC ATG GTG AAC TCC ACC CAC CGT      414
                                      Met Val Asn Ser Thr His Arg
                                        1               5

GGG ATG CAC ACT TCT CTG CAC CTC TGG AAC CGC AGC AGT TAC AGA CTG      462
Gly Met His Thr Ser Leu His Leu Trp Asn Arg Ser Ser Tyr Arg Leu
         10                  15                  20

CAC AGC AAT GCC AGT GAG TCC CTT GGA AAA GGC TAC TCT GAT GGA GGG      510
His Ser Asn Ala Ser Glu Ser Leu Gly Lys Gly Tyr Ser Asp Gly Gly
     25                  30                  35

TGC TAC GCG CAA CTT TTT GTC TCT CCT GAG GTG TTT GTG ACT CTG GGT      558
Cys Tyr Ala Gln Leu Phe Val Ser Pro Glu Val Phe Val Thr Leu Gly
 40                  45                  50                  55

GTG ATC AGC TTG TTG GAG AAT ATC TTA GAG ATT GTG GCA ATA GCC AAG      606
Val Ile Ser Leu Leu Glu Asn Ile Leu Glu Ile Val Ala Ile Ala Lys
                 60                  65                  70
```

-continued

```
AAC AAG AAT CTG CAT TCA CCC ATG TAC TTT TTC ATC TGC AGC TTG GCT      654
Asn Lys Asn Leu His Ser Pro Met Tyr Phe Phe Ile Cys Ser Leu Ala
            75                  80                  85

GTG GCT GAT ATG CTG GTG AGC GTT TCA AAT GGA TCA GAA ACC ATT ATC      702
Val Ala Asp Met Leu Val Ser Val Ser Asn Gly Ser Glu Thr Ile Ile
        90                  95                 100

ATC ACC CTA TTA AAC CGT ACA GAT ACG GAT GCA CAG AGT TTC ACA GTG      750
Ile Thr Leu Leu Asn Arg Thr Asp Thr Asp Ala Gln Ser Phe Thr Val
    105                 110                 115

AAT ATT GAT AAT GTC ATT GAC TCG GTG ATC TGT AGC TCC TTG CTT GCA      798
Asn Ile Asp Asn Val Ile Asp Ser Val Ile Cys Ser Ser Leu Leu Ala
120                 125                 130                 135

TCC ATT TGC AGC CTG CTT TCA ATT GCA GTG GAC AGG TAC TTT ACT ATC      846
Ser Ile Cys Ser Leu Leu Ser Ile Ala Val Asp Arg Tyr Phe Thr Ile
                140                 145                 150

TTC TAT GCT CTC CAG TAC CAT AAC ATT ATG ACA GTT AAG CGG GTT GGG      894
Phe Tyr Ala Leu Gln Tyr His Asn Ile Met Thr Val Lys Arg Val Gly
            155                 160                 165

ATC AGC ATA AGT TGT ATC TGG GCA GCT TGC ACG GTT TCA GGT ATT TTG      942
Ile Ser Ile Ser Cys Ile Trp Ala Ala Cys Thr Val Ser Gly Ile Leu
        170                 175                 180

TTC ATC ATT TAC TCA GAT AGT AGT GCT GTC ATC ATC TGC CTC ATC ACC      990
Phe Ile Ile Tyr Ser Asp Ser Ser Ala Val Ile Ile Cys Leu Ile Thr
    185                 190                 195

ATG TTC TTC ACC ATG CTG GCT CTC ATG GCT TCT CTC TAT GTC CAC CTG     1038
Met Phe Phe Thr Met Leu Ala Leu Met Ala Ser Leu Tyr Val His Leu
200                 205                 210                 215

TTC CTG ATG GCC AGG CTT CAC ATT AAG AGG ATT GCT GTC CTC CCC GGC     1086
Phe Leu Met Ala Arg Leu His Ile Lys Arg Ile Ala Val Leu Pro Gly
                220                 225                 230

ACT GGT GCC ATC CGC CAA GGT GCC AAT ATG AAG GGA GCG ATT ACC TTG     1134
Thr Gly Ala Ile Arg Gln Gly Ala Asn Met Lys Gly Ala Ile Thr Leu
            235                 240                 245

ACC ATC CTG ATT GGC GTC TTT GTT GTC TGC TGG GCC CCA TTC TTC CTC     1182
Thr Ile Leu Ile Gly Val Phe Val Val Cys Trp Ala Pro Phe Phe Leu
        250                 255                 260

CAC TTA ATA TTC TAC ATC TCT TGT CCT CAG AAT CCA TAT TGT GTG TGC     1230
His Leu Ile Phe Tyr Ile Ser Cys Pro Gln Asn Pro Tyr Cys Val Cys
    265                 270                 275

TTC ATG TCT CAC TTT AAC TTG TAT CTC ATA CTG ATC ATG TGT AAT TCA     1278
Phe Met Ser His Phe Asn Leu Tyr Leu Ile Leu Ile Met Cys Asn Ser
280                 285                 290                 295

ATC ATC GAT CCT CTG ATT TAT GCA CTC CGG AGT CAA GAA CTG AGG AAA     1326
Ile Ile Asp Pro Leu Ile Tyr Ala Leu Arg Ser Gln Glu Leu Arg Lys
                300                 305                 310

ACC TTC AAA GAG ATC ATC TCT TCC TAT CCC CTG GGA GGC CTT TGT GAC     1374
Thr Phe Lys Glu Ile Ile Ser Ser Tyr Pro Leu Gly Gly Leu Cys Asp
            315                 320                 325

TTG TCT AGC AGA TAT TAAATGGGGA CAGAGCACGC AATATAGGAA CATCCATAAG     1429
Leu Ser Ser Arg Tyr
        330

AGACTTTTTC ACTCTTACCC TACCTGAATA TTCTACTTCT GCAACAGCTT TCTCTTCCGT   1489

GTAGGGTACT GGTTGAGATA TCCATTGTGT AAATTTAAGC CTATGATTTT TAATGAGAAA   1549

AAATGCCCAG TCTCTGTATT ATTTCCAATC TCATGCTACT TTTTTGGCCA TAAAATATGA   1609

ATCTATGTTA TAGGTTGTAG GCACTGTGGA TTTACAAAAA GAAAAGTCCT TATTAAAAGC   1669

TT                                                                  1671
```

-continued (2) INFORMATION FOR SEQ ID NO: 16:

(i) SEQUENCE CHARACTERISTICS:
(A) LENGTH: 332 amino acids
(B) TYPE: amino acid
(D) TOPOLOGY: linear (ii) MOLECULE TYPE: protein (xi) SEQUENCE DESCRIPTION: SEQ ID NO: 16:

```
Met Val Asn Ser Thr His Arg Gly Met His Thr Ser Leu His Leu Trp
  1               5                  10                  15

Asn Arg Ser Ser Tyr Arg Leu His Ser Asn Ala Ser Glu Ser Leu Gly
             20                  25                  30

Lys Gly Tyr Ser Asp Gly Gly Cys Tyr Ala Gln Leu Phe Val Ser Pro
         35                  40                  45

Glu Val Phe Val Thr Leu Gly Val Ile Ser Leu Leu Glu Asn Ile Leu
     50                  55                  60

Glu Ile Val Ala Ile Ala Lys Asn Lys Asn Leu His Ser Pro Met Tyr
 65                  70                  75                  80

Phe Phe Ile Cys Ser Leu Ala Val Ala Asp Met Leu Val Ser Val Ser
                 85                  90                  95

Asn Gly Ser Glu Thr Ile Ile Ile Thr Leu Leu Asn Arg Thr Asp Thr
            100                 105                 110

Asp Ala Gln Ser Phe Thr Val Asn Ile Asp Asn Val Ile Asp Ser Val
        115                 120                 125

Ile Cys Ser Ser Leu Leu Ala Ser Ile Cys Ser Leu Leu Ser Ile Ala
    130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ser Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Leu Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
    290                 295                 300

Arg Ser Gln Glu Leu Arg Lys Thr Phe Lys Glu Ile Ile Ser Ser Tyr
305                 310                 315                 320

Pro Leu Gly Gly Leu Cys Asp Leu Ser Ser Arg Tyr
                325                 330
```

(2) INFORMATION FOR SEQ ID NO: 17:

(i) SEQUENCE CHARACTERISTICS:

-continued

```
          (A) LENGTH: 978 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 1..975

    (xi) SEQUENCE DESCRIPTION: SEQ ID NO: 17:

ATG AAC TCC TCC TCC ACC CTG ACT GTA TTG AAT CTT ACC CTG AAC GCC       48
Met Asn Ser Ser Ser Thr Leu Thr Val Leu Asn Leu Thr Leu Asn Ala
  1               5                  10                  15

TCA GAG GAT GGC ATT TTA GGA TCA AAT GTC AAG AAC AAG TCT TTG GCC       96
Ser Glu Asp Gly Ile Leu Gly Ser Asn Val Lys Asn Lys Ser Leu Ala
             20                  25                  30

TGT GAA GAA ATG GGC ATT GCC GTG GAG GTG TTC CTG ACC CTG GGT CTC      144
Cys Glu Glu Met Gly Ile Ala Val Glu Val Phe Leu Thr Leu Gly Leu
         35                  40                  45

GTC AGC CTC TTA GAG AAC ATC CTG GTC ATT GGG GCC ATA GTA AAG AAC      192
Val Ser Leu Leu Glu Asn Ile Leu Val Ile Gly Ala Ile Val Lys Asn
     50                  55                  60

AAA AAC CTG CAC TCA CCC ATG TAC TTC TTT GTG GGC AGC TTA GCC GTG      240
Lys Asn Leu His Ser Pro Met Tyr Phe Phe Val Gly Ser Leu Ala Val
 65                  70                  75                  80

GCC GAC ATG CTG GTG AGC ATG TCC AAT GCC TGG GAG ACT GTC ACC ATA      288
Ala Asp Met Leu Val Ser Met Ser Asn Ala Trp Glu Thr Val Thr Ile
                 85                  90                  95

TAC TTG CTA AAT AAT AAA CAC CTG GTG ATA GCC GAC ACC TTT GTG CGA      336
Tyr Leu Leu Asn Asn Lys His Leu Val Ile Ala Asp Thr Phe Val Arg
            100                 105                 110

CAC ATC GAC AAC GTG TTC GAC TCC ATG ATC TGC ATC TCT GTG GTG GCC      384
His Ile Asp Asn Val Phe Asp Ser Met Ile Cys Ile Ser Val Val Ala
        115                 120                 125

TCG ATG TGC AGT TTG CTG GCC ATT GCG GTG GAT AGG TAC ATC ACC ATC      432
Ser Met Cys Ser Leu Leu Ala Ile Ala Val Asp Arg Tyr Ile Thr Ile
    130                 135                 140

TTC TAT GCC TTG CGC TAC CAC CAC ATC ATG ACC GCG AGG CGC TCG GGG      480
Phe Tyr Ala Leu Arg Tyr His His Ile Met Thr Ala Arg Arg Ser Gly
145                 150                 155                 160

GTG ATC ATC GCC TGC ATT TGG ACC TTC TGC ATA AGC TGC GGC ATT GTT      528
Val Ile Ile Ala Cys Ile Trp Thr Phe Cys Ile Ser Cys Gly Ile Val
                165                 170                 175

TTC ATC ATC TAC TAT GAG TCC AAG TAT GTG ATC ATT TGC CTC ATC TCC      576
Phe Ile Ile Tyr Tyr Glu Ser Lys Tyr Val Ile Ile Cys Leu Ile Ser
            180                 185                 190

ATG TTC TTC ACC ATG CTG TTC TTC ATG GTG TCT CTG TAT ATA CAC ATG      624
Met Phe Phe Thr Met Leu Phe Phe Met Val Ser Leu Tyr Ile His Met
        195                 200                 205

TTC CTC CTG GCC CGG AAC CAT GTC AAG CGG ATA GCA GCT TCC CCC AGA      672
Phe Leu Leu Ala Arg Asn His Val Lys Arg Ile Ala Ala Ser Pro Arg
    210                 215                 220

TAC AAC TCC GTG AGG CAA AGG ACC AGC ATG AAG GGG GCT ATT ACC CTC      720
Tyr Asn Ser Val Arg Gln Arg Thr Ser Met Lys Gly Ala Ile Thr Leu
225                 230                 235                 240

ACC ATG CTA CTG GGG ATT TTC ATT GTC TGC TGG TCT CCC TTC TTT CTT      768
Thr Met Leu Leu Gly Ile Phe Ile Val Cys Trp Ser Pro Phe Phe Leu
                245                 250                 255

CAC CTT ATC TTA ATG ATC TCC TGC CCT CAG AAC GTC TAC TGC TCT TGC      816
His Leu Ile Leu Met Ile Ser Cys Pro Gln Asn Val Tyr Cys Ser Cys
```

-continued

```
            260                 265                 270

TTT ATG TCT TAC TTC AAC ATG TAC CTT ATA CTC ATC ATG TGC AAC TCC       864
Phe Met Ser Tyr Phe Asn Met Tyr Leu Ile Leu Ile Met Cys Asn Ser
        275                 280                 285

GTG ATC GAT CCT CTC ATC TAC GCC CTC CGC AGC CAA GAG ATG CGG AGG       912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG       960
Thr Phe Lys Glu Ile Val Cys Cys His Gly Phe Arg Arg Pro Cys Arg
305                 310                 315                 320

CTC CTT GGC GGG TAT TAA                                               978
Leu Leu Gly Gly Tyr
                325
```

(2) INFORMATION FOR SEQ ID NO: 18:

(i) SEQUENCE CHARACTERISTICS:
(A) LENGTH: 325 amino acids
(B) TYPE: amino acid
(D) TOPOLOGY: linear (ii) MOLECULE TYPE: protein (xi) SEQUENCE DESCRIPTION: SEQ ID NO: 18:

```
Met Asn Ser Ser Ser Thr Leu Thr Val Leu Asn Leu Thr Leu Asn Ala
  1               5                  10                  15

Ser Glu Asp Gly Ile Leu Gly Ser Asn Val Lys Asn Lys Ser Leu Ala
             20                  25                  30

Cys Glu Glu Met Gly Ile Ala Val Glu Val Phe Leu Thr Leu Gly Leu
        35                  40                  45

Val Ser Leu Leu Glu Asn Ile Leu Val Ile Gly Ala Ile Val Lys Asn
     50                  55                  60

Lys Asn Leu His Ser Pro Met Tyr Phe Phe Val Gly Ser Leu Ala Val
 65                  70                  75                  80

Ala Asp Met Leu Val Ser Met Ser Asn Ala Trp Glu Thr Val Thr Ile
                 85                  90                  95

Tyr Leu Leu Asn Asn Lys His Leu Val Ile Ala Asp Thr Phe Val Arg
            100                 105                 110

His Ile Asp Asn Val Phe Asp Ser Met Ile Cys Ile Ser Val Val Ala
        115                 120                 125

Ser Met Cys Ser Leu Leu Ala Ile Ala Val Asp Arg Tyr Ile Thr Ile
    130                 135                 140

Phe Tyr Ala Leu Arg Tyr His His Ile Met Thr Ala Arg Arg Ser Gly
145                 150                 155                 160

Val Ile Ile Ala Cys Ile Trp Thr Phe Cys Ile Ser Cys Gly Ile Val
                165                 170                 175

Phe Ile Ile Tyr Tyr Glu Ser Lys Tyr Val Ile Ile Cys Leu Ile Ser
            180                 185                 190

Met Phe Phe Thr Met Leu Phe Phe Met Val Ser Leu Tyr Ile His Met
        195                 200                 205

Phe Leu Leu Ala Arg Asn His Val Lys Arg Ile Ala Ala Ser Pro Arg
    210                 215                 220

Tyr Asn Ser Val Arg Gln Arg Thr Ser Met Lys Gly Ala Ile Thr Leu
225                 230                 235                 240

Thr Met Leu Leu Gly Ile Phe Ile Val Cys Trp Ser Pro Phe Phe Leu
                245                 250                 255

His Leu Ile Leu Met Ile Ser Cys Pro Gln Asn Val Tyr Cys Ser Cys
```

-continued

```
            260                 265                 270

Phe Met Ser Tyr Phe Asn Met Tyr Leu Ile Leu Ile Met Cys Asn Ser
        275                 280                 285

Val Ile Asp Pro Leu Ile Tyr Ala Leu Arg Ser Gln Glu Met Arg Arg
    290                 295                 300

Thr Phe Lys Glu Ile Val Cys Cys His Gly Phe Arg Arg Pro Cys Arg
305                 310                 315                 320

Leu Leu Gly Gly Tyr
                325


(2) INFORMATION FOR SEQ ID NO: 19:

     (i) SEQUENCE CHARACTERISTICS:
          (A) LENGTH: 30 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: misc_feature
          (B) LOCATION: 1..32
          (D) OTHER INFORMATION: /function = "Degenerate
               oligonucleotide primer (antisense)"

    (xi) SEQUENCE DESCRIPTION: SEQ ID NO: 19:

GAATTCGACG TCACAGTATG ACGGCCATGG                                      30
```